(12) United States Patent
Blömker et al.

(10) Patent No.: US 8,915,736 B2
(45) Date of Patent: Dec. 23, 2014

(54) COMPOSITION COMPRISING A MONOMER WITH A POLYALICYCLIC STRUCTURE ELEMENT FOR FILLING AND/OR SEALING A ROOT CANAL

(75) Inventors: Tobias Blömker, Cuxhaven (DE); Manfred Stepputtis, Kutenholz (DE); Reinhard Maletz, Cuxhaven (DE); Manfred Thomas Plaumann, Cuxhaven (DE); Nils Fontein, Cuxhaven (DE)

(73) Assignee: Voco GmbH, Cuxhaven (DE)

( * ) Notice: Subject to any disclaimer, the term of this patent is extended or adjusted under 35 U.S.C. 154(b) by 98 days.

(21) Appl. No.: 13/248,951

(22) Filed: Sep. 29, 2011

(65) Prior Publication Data

US 2012/0082954 A1 Apr. 5, 2012

(30) Foreign Application Priority Data

Sep. 30, 2010 (DE) .................. 10 2010 041 815
Sep. 29, 2011 (EP) ..................... 11183338

(51) Int. Cl.
*A61C 5/04* (2006.01)
*A61C 5/00* (2006.01)
*A61K 6/083* (2006.01)
*A61K 6/00* (2006.01)

(52) U.S. Cl.
CPC .................. *A61K 6/0038* (2013.01)
USPC ........... 433/228.1; 433/89; 433/224; 523/117

(58) Field of Classification Search
USPC ................... 523/117; 433/89, 228.1
See application file for complete search history.

(56) References Cited

U.S. PATENT DOCUMENTS

| | | | |
|---|---|---|---|
| 3,082,526 A | 3/1963 | Nitszche et al. | |
| 3,925,895 A | 12/1975 | Kliment et al. | |
| 4,002,669 A | 1/1977 | Gross et al. | |
| 4,160,080 A | 7/1979 | Koenig et al. | |
| 4,323,348 A | 4/1982 | Schmitz-Josten et al. | |
| 4,323,696 A | 4/1982 | Schmitz-Josten et al. | |
| 4,379,695 A * | 4/1983 | Orlowski et al. .......... | 433/217.1 |
| 4,447,520 A | 5/1984 | Henne et al. | |
| 4,449,938 A | 5/1984 | Pollak | |
| 4,490,497 A | 12/1984 | Evrard et al. | |
| 4,744,828 A | 5/1988 | Winkel et al. | |
| 4,772,530 A | 9/1988 | Gottschalk et al. | |
| 4,874,450 A | 10/1989 | Gottschalk | |
| 4,925,982 A | 5/1990 | Urano et al. | |
| 4,954,414 A | 9/1990 | Adair et al. | |
| 5,055,372 A | 10/1991 | Shanklin et al. | |
| 5,057,393 A | 10/1991 | Shanklin et al. | |
| 5,646,197 A | 7/1997 | Martin | |
| 5,708,051 A | 1/1998 | Erdrich et al. | |
| 5,761,169 A | 6/1998 | Mine et al. | |
| 5,883,153 A * | 3/1999 | Roberts et al. ............. | 523/116 |
| 6,020,528 A | 2/2000 | Leppard et al. | |
| 6,235,851 B1 * | 5/2001 | Ishii et al. ................ | 525/127 |
| 6,500,004 B2 | 12/2002 | Jensen et al. | |
| 6,652,282 B2 | 11/2003 | Jensen et al. | |
| 6,670,499 B1 * | 12/2003 | Inoue et al. ............... | 560/117 |
| 6,734,223 B2 | 5/2004 | Walz et al. | |
| 6,811,400 B2 | 11/2004 | Jensen et al. | |
| 7,081,485 B2 | 7/2006 | Suh et al. | |
| 7,148,382 B2 | 12/2006 | Wolf et al. | |
| 7,320,598 B2 | 1/2008 | Jensen et al. | |
| 7,381,785 B2 | 6/2008 | Detrembleur et al. | |
| 7,601,767 B2 * | 10/2009 | Ruppert et al. ............. | 523/116 |
| 8,044,113 B2 * | 10/2011 | Klee ........................... | 523/116 |
| 2007/0027229 A1 | 2/2007 | Moszner et al. | |
| 2008/0200586 A1 | 8/2008 | Holden et al. | |
| 2008/0206716 A1 | 8/2008 | Asgary | |
| 2008/0234404 A1 * | 9/2008 | Klee ........................... | 523/116 |
| 2008/0287566 A1 | 11/2008 | Musikant et al. | |
| 2008/0299093 A1 | 12/2008 | Yang et al. | |
| 2009/0036565 A1 * | 2/2009 | Utterodt et al. ............ | 523/116 |
| 2009/0131552 A1 | 5/2009 | Hsieh et al. | |
| 2010/0004416 A1 * | 1/2010 | Neffgen et al. ............ | 526/328.5 |
| 2010/0076115 A1 * | 3/2010 | Utterodt et al. ............ | 523/116 |
| 2011/0053117 A1 | 3/2011 | Engelbrecht et al. | |
| 2012/0093741 A1 * | 4/2012 | Maletz et al. .............. | 424/49 |

FOREIGN PATENT DOCUMENTS

| | | |
|---|---|---|
| DE | 3236026 A1 | 3/1984 |
| DE | 3338077 A1 | 5/1985 |
| DE | 4231579 A1 | 3/1993 |
| DE | 4416857 C1 | 6/1995 |
| DE | 19903177 A1 | 7/2000 |
| DE | 10119831 A1 | 10/2002 |
| DE | 10352260 B3 | 4/2005 |
| DE | 102004060285 A1 | 6/2006 |
| DE | 60116142 T2 | 7/2006 |
| DE | 102006019092 A1 | 3/2007 |
| DE | 60029481 T2 | 7/2007 |
| DE | 102006050153 A1 | 5/2008 |
| EP | 0057474 A2 | 7/1979 |
| EP | 0007508 A2 | 2/1980 |
| EP | 0047902 A2 | 8/1981 |
| EP | 0049631 A1 | 10/1981 |
| EP | 0059451 A1 | 2/1982 |
| EP | 0173567 A2 | 8/1985 |
| EP | 0184095 A2 | 11/1985 |
| EP | 0209700 A2 | 6/1986 |
| EP | 0264551 A2 | 7/1987 |
| EP | 3703120 A1 | 1/1988 |
| EP | 0254950 A2 | 2/1988 |

(Continued)

*Primary Examiner* — Tae H Yoon

(74) *Attorney, Agent, or Firm* — Duane Morris LLP; J. Rodman Steele, Jr.; Gregory M. Lefkowitz

(57) ABSTRACT

A curable dental composition comprising a monomer with a polyalicyclic structure element that can be used for filling and/or sealing of a root canal is described. Also described is a composition useful as a dental material and a method for preparing such a composition. New polymerizable monomers comprising at least one polyalicyclic structure element and certain ethylenic structure elements, which are particularly suitable for use in a dental composition, and the use of the new monomers in a dental composition are also described.

19 Claims, No Drawings

(56) References Cited

FOREIGN PATENT DOCUMENTS

| | | |
|---|---|---|
| EP | 0325266 A2 | 7/1989 |
| EP | 0262629 A2 | 9/1989 |
| EP | 0366977 A2 | 10/1989 |
| EP | 0682012 A1 | 11/1995 |
| EP | 0712840 A1 | 5/1996 |
| EP | 0783880 B1 | 7/1997 |
| EP | 0948955 A1 | 6/1998 |
| EP | 0864312 A2 | 9/1998 |
| EP | 0867457 A1 | 9/1998 |
| EP | 0980682 A1 | 8/1999 |
| EP | 1112995 B1 | 9/1999 |
| EP | 69518030 T2 | 12/2000 |
| EP | 1563821 A1 | 1/2001 |
| EP | 1236459 B1 | 7/2001 |
| EP | 1238993 A1 | 9/2002 |
| EP | 1547571 A1 | 6/2005 |
| EP | 1645582 A1 | 4/2006 |
| EP | 1839640 A2 | 3/2007 |
| EP | 60125374 T2 | 4/2007 |
| EP | 102005053775 A1 | 5/2007 |
| EP | 102006060983 A1 | 6/2008 |
| EP | 2016931 A2 | 1/2009 |
| EP | 2031003 A1 | 3/2009 |
| EP | 2031005 A2 | 3/2009 |
| FR | 2640503 A1 | 12/1989 |
| GB | 1110673 | 4/1968 |
| GB | 1576080 | 10/1980 |
| JP | 07206740 | 8/1995 |
| WO | 02092021 A1 | 11/2002 |
| WO | 02092023 A1 | 11/2002 |
| WO | 03035013 A1 | 5/2003 |
| WO | 2005084611 A1 | 9/2005 |
| WO | 2006026065 A2 | 3/2006 |
| WO | 2006063891 A1 | 6/2006 |
| WO | 2008100451 A2 | 8/2008 |
| WO | 2008100452 A2 | 8/2008 |
| WO | 2009065873 A2 | 5/2009 |

\* cited by examiner

COMPOSITION COMPRISING A MONOMER WITH A POLYALICYCLIC STRUCTURE ELEMENT FOR FILLING AND/OR SEALING A ROOT CANAL

CROSS-REFERENCE TO RELATED APPLICATIONS

This application claims priority to German Application No. DE 10 2010 041 815.3 filed Sep. 30, 2010, and European Application No. EP 11 183 338 filed Sep. 29, 2011, the entireties of which are incorporated herein by reference.

FIELD OF THE INVENTION

The present invention relates to a curable dental composition comprising a monomer with a polyalicyclic structure element, which can be used for filling and/or sealing a root canal. The invention also relates to a composition according to the invention as a dental material and a method for preparing a composition according to the invention. The invention further relates to new polymerizable monomers comprising at least one polyalicyclic structure element and certain ethylenic structure elements, which are particularly suitable for use in a composition according to the invention, and the use of the new monomers in a composition according to the invention.

BACKGROUND OF THE INVENTION

The aim of a definitive root canal filling is a durable, three-dimensional, bacteria-proof and hermetically sealed obturation of the prepared and cleaned pulp cavity to protect the periodontium and the anatomically bordering structures. By completely sealing the root canal any transport of fluids is inhibited, so that any bacteria remaining in the canal have no further opportunity to breed.

Generally a root canal filling is undertaken with a semi-plastic filling material in combination with a sealing material. The object of the sealing material is to
- smooth out unevenness and incongruities along the canal wall,
- seal the lateral canals and the exposed dentin tubuli, and
- create a tight seal between the filler material and the root canal wall.

The requirements to be met by a root canal sealing material here are extremely varied and very different from those of a conventional restoration material for filling of tooth cavities.

The material should be easy to introduce into the root canal, it should penetrate the entire cavity including the fine gaps and adjacent channels and fill these, it should have precise and slow curing kinetics and should demonstrate volume stability and insolubility in respect of tissue fluids. The sealing capability is a decisive criterion for the suitability of the sealing material, since with the main filling mass a bacteria-proof sealing of the root canal is not possible. The material should also be radiopaque and biocompatible, tissue-compatible and durable. It should shrink only slightly, not cause discoloration of the tooth and, if necessary, be able to be removed in the course of revision. In addition it should demonstrate a good parietal strength and good adaptation to the dentin walls. If the root canal and/or sealing material exists as two separate components (for example as two pastes), which cure after mixing with one another, both pastes must be easily miscible with each other.

The slow curing is necessary in order that the dentist has sufficient time available to take an X-ray to check the root canal filling and optionally undertake additional root canal treatment.

Full sealing of the root canal is complicated by the fact that the root canal system consists of not only the main canal, but also branches, small ramifications and side canals in the most varied of forms. So for example decomposition products of the diseased pulpa and degradation products and metabolites of the bacteria involved in the disease can reach both the periapical region, via the main canal, and the desmodontal via the side canals. In this way an inflammation that has already started to subside can be reverted to the acute phase. Since in addition to the side canals bacteria and their metabolites can also populate the smallest of ramifications and even penetrate deep into the dentin canals, despite thorough mechanical preparation and careful chemical disinfection by flushing, sterilization of the canal cannot be achieved.

The infiltration of contaminated fluid does not only take place from the canal system outwards, but can also occur from the outside to the inside of the canal. On top of this, microorganisms, liquid food residues and saliva can reach the canal via the oral cavity through the coronal access of an inadequately filled root canal and infect this.

Only a tightly-sealed root canal filling can prevent the penetration of pathogens and isolate the species remaining in the canal from the environment thereby denying these a substrate. In this connection it has been established on numerous occasions that in a tightly sealed root canal, bacteria can even die off.

The material currently chosen according to the prior art for use in bacteria-proof sealing of the root canal system is gutta-percha in combination with a sealing material (sealer). Gutta-percha is introduced into the root canal in the form of standardized points. The gutta-percha points consist of polyisoprene. The point and the canal wall are coated with the sealer and the point is then introduced into the canal. Remaining cavities can be filled with further points or further quantities of sealer. The preformed point and the sealing material are adapted to the canal wall with suitable instruments.

In the past various sealing/filling materials have been proposed.

DE 24 20 351 C3 describes the use of a composition as a root canal filling component, containing a hydrophilic, polymerizable material in hydroxy-lower-alkyl acrylate and/or hydroxy-lower-alkyl methacrylate forming a homopolymer or a mixed polymer with a content of 1 through 50% alkyl acrylates or methacrylates and an active filler as well as optionally a fine-particle radiopaque material. In the examples of the patent specification in one component of the chemically-curing composition as the hydroxy-lower-alkyl methacrylate, hydroxyethyl methacrylate (HEMA) is used, while the second component, containing peroxide, comprises a large quantity of non-reactive diluent such as for example glycerin diacetate.

During radical cross-linking of methacrylate/acrylate compositions a three-dimensionally linked network results. Because of the very low size of the water molecule water can diffuse into the mesh of the polymer, where it accumulates at certain points in the network and there forms hydrogen bonds or other weak polar bonds. The more polar components that are present in the polymer matrix, the easier it is for further water absorption to take place. As a result of water absorption the polymer expands and a structural reorganization of the polymer chains can occur. The resultant compressive stress can cause lasting damage to the tooth structure. On top of this water molecules can attack sensitive structure elements of the polymer such as for example ester groups, hydrolytically splitting these. This decomposition can lead to total disintegration of the network.

It can be expected that compositions, as described in DE 24 20 351 C3, because of the relatively large quantity of both HEMA and non-reactive thinning monomers will absorb a lot of water. In the patent document itself reference is made to the highly hydrophilic nature of the composition. The high level of water absorption, which is claimed to take place via the root tip, is claimed to increase the volume of the polymer and thus seal the entire cavity of the canal. As explained above, however, the resultant compressive stress can instead damage the tooth structure and it is very likely that through the presence of a large quantity of water the polymer will be irreversibly hydrolytically cracked and decomposed.

Unlike the compositions of DE 24 20 351 C3, which comprise low-molecular methacrylates, DE 10 2007 029 640 A1 discloses polymerizable root canal filling and sealing materials containing high-molecular dimethacrylates, curing agents and radiopacifying additives. The high-molecular long-chained dimethacrylates used are claimed to have an average molecular weight of more than 600 and are contained in the compositions in quantities of 2 through 90 wt. %, particularly preferably in quantities of 15 through 30 wt. %. Preference is for dimethacrylate compounds with hydrophilic properties such as for example —$CH_2$—O— or —$CH_2$—$CH_2$—O— and/or OH—, $NH_2$— groups. Particularly preferred are —$CH_2$—$CH_2$—O— units. High-molecular dimethacrylates with polyalicyclic structure elements are not disclosed in DE 10 2007 029 640 A1.

Preferably in DE 10 2007 029 640 A1 dimethacrylate compounds with a plurality of hydrophilic units are used. Preference is for compounds with 10 hydrophilic units, particularly preferably with 20 hydrophilic units, quite particularly preferably those with 30 hydrophilic units. By way of example the application mentions ethoxylated bisphenol A dimethacrylate E (30) with a molecular weight of 1678, ethoxylated bisphenol A dimethacrylate E (10) with a molecular weight of 804, polyalkylene glycol dimethacrylate EP 100 with a molecular weight of 1114 or polyethylene glycol 600 dimethacrylate with a molecular weight of 754.

Common to all these compounds is the fact that they have highly-flexible molecular chains since for example the ethoxy groups are able to rotate unhindered around their ether bond. This fact means that the packing and arrangement of the molecular chains in the polymer is not homogenous and rigid, but movable and open. It can thus be expected that the compositions from DE 10 2007 029 640 A1 as well as those from DE 24 20 351 C3 will also absorb large quantities of water. This will likewise lead to a damaging compressive strain on the tooth structure. In addition, the quantity of water absorbed by the polymer will hydrolytically split and irreversibly degrade the network.

US 2009/0131552 discloses a root canal sealing material comprising a photocurable urethane-monoacrylate oligomer with an acrylate and a hydroxyl group at both ends, at least one di- or multifunctional acrylate/methacrylate thinning monomer and at least one initiator. The oligomer is the product of isophorone diisocyanate and an acrylate, having a hydroxyl group, in a first reaction stage. Here for example 1 mol HEMA reacts with one mol isophorone diisocyanate in an isocyanate-alcohol polyaddition. In a second step the isocyanate group still remaining on the alicyclic radical is reacted in a second reaction stage, for example with a polyester polyol such as polybutylene adipate glycol. The result is a urethane monomethacrylate with a polyalicyclic radical. Compared with the structures from DE 10 2007 029 640 A1 and DE 24 20 351 C3, therefore, on the one hand this structural framework contains polyurethane groups, which are highly suited to forming stable superstructures through intermolecular interactions ensuring a relatively fixed molecular chain bond in the polymer, and on the other this structure type has an alicyclic radical that provides the polymer with hydrophobic characteristics. A disadvantage of this system is the fact that the urethane monomethacrylate can only form molecular chains and is not cross-linkable. Since despite steric hindrance it can be expected that the alicyclic ring will constantly change its conformation, this system also has flexible structure elements that make the infiltration of water molecules into the polymer likely. This system will thus also absorb not insignificant amounts of water, exert a damaging compressive stress on the dental substance and in a short space of time will be hydrolytically decomposed.

DE 10 2005 041 115 A1 describes a root canal sealing material, which claims to compensate to some extent or eliminate the volume shrinkage of the cured dental mass caused by the radical polymerization. This is claimed to take place with a component that releases a gas during curing, so that the volume of the composition through the formation of small gas bubbles expands and compensates for the volume shrinkage. The gas-releasing component used is for example an acid/alkaline pairing, such as citric acid/sodium bicarbonate. The acid/alkaline pairing is formulated separately in two pastes. When the pastes are mixed the bicarbonate is protonated by the acid with the formation of carbon dioxide, which then decomposes with the formation of $CO_2$ and water. Further gas-releasing components are, for example, azobisisobutyronitrile, a compound that is able to give off nitrogen, or the combination of isocyanate and water, which react to produce an amine and $CO_2$ with the amine reacting with further isocyanate to form urea derivatives. The problem with this concept is the uncontrolled release of gas and the possibility of the gas bubbles not constituting sealed cells that are isolated from one another but ones which join together or are open thereby providing a route into the tooth tissue for bacteria and other contaminants.

DE 695 18 030 T2 proposes a tooth filling composition for sealing the root canal with an epoxy/amine basis. The reaction of a diepoxy monomer with a primary monoamine and/or disecondary diamine is claimed to produce a thermoplastically linear polymer that is suitable for sealing the root canal. Apart from the strong exotherm of the epoxy/amine polyaddition and the associated high shrinkage behavior both epoxies and amines, which are present in stoichiometric quantities, in particular because of their toxic profile, are considered to be rather problematical materials for being in direct contact with human tissue.

In U.S. Pat. No. 6,734,223 B2 dental compounds are proposed which preferably can be used as root canal filling materials and having a polymerizable monomer, a polyaminoether with a particular structure, pigments, organic and/or inorganic fillers, initiators and stabilizers. Instead of the primary monoamines and secondary diamines used in DE 69518030 T2 as reaction partners in the polyaddition, here polyaminoesters, prepared from mono-, di- or polyamines and bis- or polyacrylates are used, which are then cured in a gradual polymerization preferably with di- or polyepoxies or polyisocyanates. In U.S. Pat. No. 6,734,223 B2 inter alia 3,(4),8,(9)-dimethacryloyl(oxymethyl)tricyclo[$5.2.1.0.^{2,6}$] decane is indicated as a polymerizable monomer.

A similar approach to DE 695 18 030 T2 and U.S. Pat. No. 6,734,223 B2 can be found in US 2008/0287566 A1. As the root canal sealing material the reaction product from a diepoxy oligomer, comprising a mixture of bisphenol A diepoxy oligomers and/or bisphenol F diepoxy oligomers, with polyamine/amide monomers is described. Here the polyamine monomers have two polyamine regions, which are structurally linked together via a carbon region. The hydrocarbon region, which can be substituted, comprises at least 28 hydrocarbon atoms. In the published document it is proposed that this material is also used for pre-coating of the gutta-percha points, in order to improve the bond between the points and the sealing material. Since gutta-percha consists of polyisoprene, the more hydrophobic hydrocarbon regions in the epoxy polymer are claimed to ensure a better compatibility between point and sealing material.

EP 1 547 571 B1 describes dental root canal filling composition comprising amino-terminated prepolymers.

DE 60 125 374 T2 discloses dental compounds based on bisacrylamides, which preferably can be used as dental root canal filling materials and are claimed to have an improved hydrolytic stability.

In printed publications U.S. Pat. No. 7,320,598 B2, U.S. Pat. No. 6,811,400 B2, U.S. Pat. No. 6,500,004 B2 and U.S. Pat. No. 6,652,282 B2 root canal sealing materials are claimed having a high adhesion to the tooth structure. The compositions contain so-called adhesive monomers, in particular oxyphosphoralkyl methacrylates. Particular preference is claimed for the use of bis-glycerol dimethacrylate phosphate. Further suitable adhesive monomers for use in compositions for the root canal are claimed as bis-2-hydroxyethyl methacrylate phosphate, phosphate esters of 3-hydroxypropyl methacrylate and phosphate esters of 4-hydroxypropyl methacrylate.

In US 2008/0200586 sealing materials are described, inter alia for root canals, which are claimed to expand or contract and be able to change shape. Such behavior is claimed to be triggered preferably by polymer particles which are first pre-stressed and then relaxed.

A composition containing such particles is claimed to bring about a seal even in an unevenly formed root canal.

In U.S. Pat. No. 5,646,197 an anti-microbial root canal filling material based on zinc oxide and hydrogenated rosin ester is disclosed.

U.S. Pat. No. 4,449,938 concerns an endodontic filling and sealing composition based on polysiloxanes.

From EP 0 864 312 a kit is known, comprising two components which following mixing with each other cure and are suitable as a root canal filling material. The material cures in an addition reaction of the two components to form a polysiloxane, wherein one component comprises one or a plurality of silicon oils, which have at least two SiH groups and the other component comprises one or a plurality of silicon oils having at least two vinyl groups and one of the two components furthermore contains a catalyst.

DE 11 39 940 A is aimed at a combination of primary products for the preparation of dental root filling compositions, consisting of hydroxyl end-blocked linear diorganopolysiloxanes and organotriacylsiloxanes.

US 2008/0206716 A1, WO 2008/100451 A2 and WO 2008/100452 A2 describe water-based systems for filling the root canal.

From US 2008/0299093 A1 a hydraulic cement for filling of a root canal can be inferred.

Although many different systems exist for filling and sealing a root canal, the requirements to be met by such a material are so varied and complex that to date no material has been created that satisfactorily meets all requirements.

An extremely important characteristic of sealing materials for the root canal is the lowest possible water absorption of the material. During radical cross-linking of methacrylate/acrylate compositions a three-dimensionally linked network results. Because of the very low size of the water molecule water can diffuse into the mesh of the polymer, where it accumulates at certain points in the network and there forms hydrogen bonds or other weak polar bonds. The more polar components that are present in the polymer matrix, the easier it is for further water absorption to take place. As a result of water absorption the polymer expands and a structural reorganization of the polymer chains can occur. The resultant compressive stress can cause lasting damage to the tooth structure. On top of this water molecules can attack sensitive structure elements of the polymer such as for example ester groups, hydrolytically splitting these. This decomposition can lead to total disintegration of the network.

On the other hand, a certain polarity of the sealing materials is also desirable, however, since the tooth structure is hydrophilic and a polar composition guarantees a good adaptation of the material to the tooth substrate. Through the preparation of the root canal and the removal of the endodontium the tooth is nevertheless dead so that the hydrophilic environment in the root canal is reduced. A good wettability of the substrate should thus also be achievable with moderately hydrophilic structures.

Root canal sealing materials should have the lowest possible shrinkage during curing. The change in density or volume reduction of the reaction resin mass is what is referred to as shrinkage. This is primarily dependent upon the number of functional groups that have reacted. The shrinkage takes place both in the fluid state, thus at the very start of the polymerization, as well as during and after gelling. Overall shrinkage is subdivided into a physical and chemical component. Whereas physical shrinkage is directionally determined and, spatially, from the outer areas of the polymer, operates in a similar fashion to and in accordance with the drop in temperature that takes place, towards the central point of the molding material as it cures, the chemical component is not directionally determined, takes place solely as a result of the polymer formation and is highly dependent upon the geometrical conformation and configuration parameters of the newly constructed macromolecule. Here, during the polymerization, it is a case of the approximation of the monomeric building blocks of a van der Waals gap to the gap of a covalent bond. Furthermore, the packing density of the polymer chains is higher than the packing density of the monomers.

The shrinkage can thus lead to the formation of marginal gaps between the cured composite and the tooth wall. Such a circumstance can lead to the infiltration of bacteria and contaminated fluids into the root canal. A new inflammation focus is then generated, since a bacteria-proof seal of the root canal is not achieved.

The shrinkage is generally counteracted by a high filler content in the composite formulation, since conventional dental fillers do not change their volume. A high filler content is, however, an obstacle to the requirement of extremely good flow behavior of the root canal filling and sealing material, since the root canal to be filled with the material is on the one hand very narrow and on the other has a highly-complex forked structure.

Cross-linkable monomers, having a polyalicyclic structure element, in particular a tricyclo[$5.2.1.0^{2,6}$]decane (TCD) structure element, are already known as components of dental compositions.

Thus for example in DE 29 31 926 the acrylic or methacrylic acid esters of oxyalkylated bis(hydroxymethyl)tricyclo[$5.2.1.0^{2,6}$]decane are proposed as binding agents for dental compositions. Starting with the reaction product of the commercially available bis(hydroxymethyl)tricyclo[$5.2.1.0^{2,6}$]decane and alkylene oxides and subsequent esterification with acrylic or methacrylic acid, monomers having a tricyclic hydrocarbon structure element can be prepared in a simple manner. These compounds are claimed for use preferably in the area of dentistry, for example for the preparation of dental fillers, tooth repair materials, coating compounds, sealing compounds for cavities, crowns, bridges and veneering materials, prosthesis materials, artificial teeth and orthodontic devices. In the example section of DE 29 31 926 numerous examples of the preparation of dental pastes are provided. Root canal materials are not mentioned in the description and neither are examples given of compositions that would be suitable for use as a root canal material.

In DE 28 16 823 the bismethacrylic acid esters of the dihydroxymethyltricyclo[5.2.1.0.$^{2,6}$]decane [=bis(hydroxymethyl)tricyclo[5.2.1.0.$^{2,6}$]decane] are described as particularly suitable polymerizable components for dental materials, since they result in particularly dimensionally stable and hard polymers. They are by way of example used as dental fillers, for preparations for building up missing parts of teeth, as coating and sealing compositions, as primers for cavities, as crown, bridge and veneering materials, as compositions for the preparation of artificial teeth, as prosthesis materials and for orthodontic devices. Root canal materials are not mentioned in this document. The numerous embodiments describe dental materials which are unsuited to use in the root canal.

In DE 24 06 557 the bis-glycidyl ether of the dihydroxymethyltricyclo[5.2.1.0.$^{2,6}$]decane is reacted with 2-hydroxyethyl methacrylate to form the corresponding dimethacrylate. Together with amorphous silica the compounds described here are claimed to be suitable dental filling materials. The patent specification focuses on the highly increased water absorption of the tricyclodecane derivates compared with conventional monomers. Such a characteristic is claimed to lead to a better marginal sealing behavior of the filler material. Root canal materials are not indicated.

In DE 35 22 006 A1 and DE 35 22 005 A1 methacrylic acid derivates of tricyclo[5.2.1.0.$^{2,6}$]decanes are claimed for use in tooth filling compositions and in tooth coatings. The monomer mixtures can be used without the addition of fillers as coatings (dental lacquers). When used as a tooth filling composition the monomer mixtures should generally have fillers added. In order to be able to achieve a high filler loading, monomer mixtures having a viscosity in the range 60 through 10,000 mPas are claimed to be particularly advantageous. Root canal materials are not described. The compositions of the exemplary embodiments are unsuited to use in the root canal.

In DE 37 03 080 A1 inter alia methacrylic acid esters are described having a spatially centrally arranged tricyclo[5.2.1.0.$^{2,6}$]decane structure element and can be used as monomers for dental materials, for example as filling materials for teeth, coatings for teeth and components for the production of dentures, preferably synthetic teeth. Materials for the root canal or compositions which can be used in the root canal are not indicated.

In DE 37 03 130 A1 and DE 37 03 120 A1 urethane groups containing methacrylic acid derivatives of tricyclo[5.2.1.0.$^{2,6}$]decanes or bicyclo[2.2.1]heptanes are proposed as monomers for tooth coatings, tooth filling compositions and for preparation of synthetic teeth. Root canal materials are not described. The exemplary embodiments relate to compositions that are unsuited to use in the root canal.

In DE 10 2005 053 775 A1 a fine-flowing composite material is described that is claimed to bring about a reduction in the shrink force and is used as a cavity liner. The preferred monomers used are bis(methacryloyloxymethyl)tricyclo[5.2.1.0.$^{2,6}$]decane and bis(acryloyloxymethyl)tricyclo[5.2.1.0.$^{2,6}$]decane. Root canal materials are not described. The compositions of the exemplary embodiments are unsuited to use in the root canal.

DE 10 2007 034 457 A1 relates to dental materials with low shrink force and high flexural strength, which can contain as monomer constituent bis(methacryloyloxymethyl)tricyclo[5.2.1.0.$^{2,6}$]decane and bis(acryloyloxymethyl)tricyclo[5.2.1.0.$^{2,6}$]decane and can be used as filling materials. The dental compositions have a very high filler content which is responsible for the high flexural strength values. Such compositions are unsuited to applications in the root canal, since firstly, because of their high filler content, they cannot be introduced into the canal, and secondly they are so solid that in the course of a revision they are not easy to remove from the canal.

In DE 10 2006 060 983 A1 the use of urethane groups containing acrylic acid esters of tricyclo[5.2.1.0.$^{2,6}$]decane in dental composites is described. The presence of the acrylic acid ester is claimed to lower the cytotoxicity of the mixture of monomers compared with a mixture of conventional monomers.

WO 03/035013 A1 and DE 602 16 951 T2 relate to dental adhesive compositions for binding of dental restoration means to dentin and/or tooth enamel. In these documents inter alia the preparation of 3,(4),8,(9)-bis(2-propenamidomethyl)tricyclo[5.2.1.0]$^{2,6}$-decane is described.

From the prior art, the use of monomers with a polyalicyclic structure element for materials for sealing and/or filling the root canal can be inferred.

A distinction is made between materials for root canal sealing based on methacrylates and/or acrylates, for example according their type of curing, which can be either by photo- and/or autopolymerization. Preferably they are set to be dual-curing, since the light quanta from the polymerization lamp cannot penetrate deeply enough into the root canal. Furthermore, with this application the most complete possible reaction level is necessary in order that no unreacted and thus free monomers, which as it will be known can have toxic characteristics, penetrate the live tissue via the tip of the root and are able to cause inflammation there. Redox-induced autopolymerizable systems have post-curing and their reaction rate is higher than the reaction rate of purely photo-cross-linkable compositions. Dual-curing systems are thus clinically preferred for root canal sealing.

When using a combination of photocuring and chemical autopolymerization the network density of the polymer on the side turned towards the polymerization lamp, thus towards the oral cavity, is greater than on the opposing side, towards the root canal tip, since the effect of the dual-curing method is at its greatest at the coronal inlet of the root canal. This effect is extremely important, since the seal of the root canal against the oral cavity is the most critical.

Also of relevance here are the selection of the components of the composition and kinetics during curing, i.e. the kinetic setting of the redox system. It must be ensured that both a processing time for the material that is acceptable to the dentist, i.e. sufficiently long, can be ensured, and that the most complete reaction of the reactants in the bottom of the root canal is ensured. The redox system must thus be fashioned so that the polymer generates sufficient internal strength and a tight seal of the canal, but the strength should not be too high for in the event of a revision or when used as a temporary material it must be easily removable from the canal with dental instruments.

DESCRIPTION OF THE INVENTION

The primary object of the invention was to provide a dental composition suitable for the filling and/or sealing of a root canal and having as many as possible of the following characteristics:

a high resistance to water (low water absorption) and low solubility, good radiopacity, good adaptation to the cavity walls of the tooth, very good mechanical characteristics (in particular flexural strength and modulus of elasticity) ensuring that the root canal retains a tight seal, but that the composition in the cured state is also easy to remove in the event of a revision, sufficient flow, in order to completely fill the complicated geometries of the root canals.

Here the composition should demonstrate a shrinkage behavior such that the formation of marginal gaps (due to the bacterial penetration to be avoided) is avoided and a sufficiently tight seal of the canal is ensured.

The composition should also have a sufficiently long processing time (approximately 30 through 120 minutes from preparation of the composition, i.e. directly after mixing of the components).

The primary object is achieved according to the invention by the use of a curable dental composition consisting of or comprising:

(a) a monomer component comprising or consisting of
  (a1) one, two or a plurality of polymerizable monomers with a molar mass of less than 4,000 g/mol selected from the group consisting of compounds (monomers) with the structure $Q(YZ_e)_b$, wherein the following applies:
    Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups,
    b is an integer selected from the group of integers 1, 2, 3 and 4,
    each Z represents a structure element, which independently of any further structure elements Z is selected from the group consisting of
    —O—(C=O)—CH=CH$_2$, —O—(C=O)—C(CH$_3$)=CH$_2$,
    —(C=O)—CH=CH$_2$, —(C=O)—C(CH$_3$)=CH$_2$,
    —CH=CH$_2$, —C(CH$_3$)=CH$_2$ and —O—CH=CH$_2$
    each index e is an integer, which independently of any other indices e is selected from the group of integers 1, 2, 3 and 4,
    each Y represents a structure element, which in the structure $Q(YZ_e)_b$ bonds the polyalicyclic structure element Q with e structure elements Z, wherein each Y is selected independently of any further structure elements Y or is omitted,
  (a2) optionally one, two or a plurality of further polymerizable monomers from the group consisting of acrylates and methacrylates, preferably from the group of methacrylates,
(b) one or a plurality of initiators and/or catalysts, and
(c) a filler component consisting of or comprising
  (c1) one, two or a plurality of radiopaque fillers,
and optionally one or a plurality of further additives.

In other words the present invention relates to a curable dental composition, consisting of or comprising:

(a) a monomer component comprising or consisting of
  (a1) one, two or more polymerizable monomers with a molar mass of less than 4,000 g/mol selected from the group consisting of compounds (monomers) with the structure $Q(Y_xZ_e)_b$, wherein the following applies:
    Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups (here preferably C1-C4-alkyl), alkoxy groups (here preferably C1-C4-alkoxy), halogen atoms (here preferably F) or trifluormethyl groups,
    b is an integer selected from the group of integers 1, 2, 3 and 4,
    each Z represents a structure element, which independently of any other structure elements Z is selected from the group consisting of
    —O—(C=O)—CH=CH$_2$, —O—(C=O)—C(CH$_3$)=CH$_2$,
    —(C=O)—CH=CH$_2$, —(C=O)—C(CH$_3$)=CH$_2$,
    —CH=CH$_2$, —C(CH$_3$)=CH$_2$ and —O—CH=CH$_2$,
    each index e is an integer, which independently of any further indices e is selected from the group of integers 1, 2, 3 and 4,
    each index x independently of any further indices x represents 0 or 1,
    each Y in the structure $Q(Y_xZ_e)_b$ where x=1 represents a structure element, which bonds the polyalicyclic structure element Q with e structure elements Z, wherein each Y is selected independently of any further structure elements Y,
(b) one or a plurality of initiators and/or catalysts, and
(c) a filler component comprising or consisting of
  (c1) one, two or a plurality of radiopaque fillers,
and optionally one or a plurality of other additives.

All the statements below relating to the compounds of structure $Q(YZ_e)_b$ (wherein each Y is selected independently of any further structure elements Y or is omitted) and the preferred or particularly preferred configurations of the present invention indicated in connection with these compounds apply accordingly to the compounds of structure $Q(Y_xZ_e)_b$ (wherein each index x independently of any further indices x represents 0 and 1), and vice versa.

A compound according to the invention or to be used according to the invention of structure $Q(Y_xZ_e)_b$ comprises a polyalicyclic structure element Q, which is derived from a corresponding polyalicyclic hydrocarbon. In the context of the present text, this means that b hydrogen atoms of the hydrocarbon are replaced by substituents $Y_xZ_e$ (as described above), and optionally one, two or a plurality of the hydrogen atoms not substituted by $Y_xZ_e$ are substituted by alkyl groups, alkoxy groups, halogen atoms or trifluoromethyl groups. The polyalicyclic structure element Q is constituted by carbon ring atoms. Carbon atoms outside the rings are a constituent of substituents.

The "polyalicyclic" structure element Q is a bicyclic, tricyclic, tetracyclic, pentacyclic or hexacyclic hydrocarbon radical as defined above. The designations "bicyclic", "tricyclic", "tetracyclic", "pentacyclic" and "hexacyclic" here correspond to the IUPAC nomenclature.

Preferably each Y represents a structure element, which in the structure $Q(Y_xZ_e)_b$ with x=1, bonds the polyalicyclic structure element Q with e structure elements Z, wherein each Y is selected independently of any further structure elements Y.

The compositions according to the invention, because of their exceedingly low water absorption and their exceedingly low solubility and their processing characteristics are quite exceptionally suitable as root canal sealing and filling materials.

In addition, the adaptation of the compositions according to the invention to the canal walls and the flow characteristics are exceptional.

The composition according to the invention is preferably photocurable, preferably dual-curing.

The total of the numerical values of the index b and the index e is preferably 3, 4, 5, 6, 7 or 8.

Within the context of the present text (meth)acrylic means both acrylic and methacrylic.

Preferably the polymerizable monomers of structure $Q(YZ_e)_b$, (as defined above and wherein each Y is selected independently of any further structure elements Y or is omitted) of component (a1) have a molar mass of less than 3,000 g/mol, preferably of less than 2,000 g/mol, more preferably of less than 1,500 g/mol.

In a preferred composition according to the invention monomer component (a) comprises or monomer component (a) consists of (a1) one, two or a plurality of polymerizable monomers as defined above and (a2) one, two or a plurality of further polymerizable monomers from the group consisting of acrylates and methacrylates, preferably acrylates and methacrylates with a polyether structure element, preferably with a polyetherpolyol structure element, wherein the ratio of the weight of component (a1) to the weight of component (a2) is preferably in the range 3:1 through 1:3, preferably in the range 2:1 through 1:2, more preferably in the range 3:2 through 2:3.

Similarly preferred is a composition according to the invention (as defined above), wherein the monomer component contains (a1) one, two or a plurality of polymerizable monomers as defined above under (a1), and (a2) one, two or a plurality of further polymerizable monomers from the group consisting of acrylates and methacrylates with a polyether structure element, wherein none of these further polymerizable monomers is one of those with a structure $Q(Y_xZ_e)_b$ according to the above definition under (a1), wherein the ratio of the total weight of the (a1) polymerizable monomers according to the above definition under (a1) to the total weight of the (a2) one, two or a plurality of further polymerizable monomers from the group consisting of acrylates and methacrylates with a polyether structure element, wherein none of the further polymerizable monomers is one of those with a structure $Q(Y_xZ_e)_b$ according to the above definition under (a1), is preferably in the range 3:1 through 1:3, preferably in the range 2:1 through 1:2, more preferably in the range 3:2 through 2:3.

For the purposes of quantitative considerations, each compound falling under the definition of component (a1) or (a2) must be attributed to component (a1) or (a2) respectively.

In a preferred composition according to the invention the monomer component (a) comprises component (a1) in a total quantity of 5 through 48.5 wt. %, preferably 8 through 30 wt. %, preferably 10 through 20 wt. %, and/or component (a2) in a total quantity of 5 through 48.5 wt. %, preferably 8 through 30 wt. %, preferably 10 through 20 wt. %, in each case in relation to the total weight of the composition.

Put another way, preference is for a composition according to the invention (as defined above), wherein the monomer component (a) comprises as component (a1) a total quantity in the range 5 through 48.5 wt. %, preferably 8 through 30 wt. %, preferably 10 through 20 wt. % of polymerizable monomers with a molar mass of less than 4,000 g/mol, selected from the group consisting of compounds (monomers) of structure $Q(Y_xZ_e)_b$ according to the above definition under (a1), and/or as component (a2) a total quantity in the range 5 through 48.5 wt. %, preferably 8 through 30 wt. %, preferably 10 through 20 wt. % of one, two or a plurality of further polymerizable monomers, selected from the group consisting of acrylates and methacrylates with a polyether structure element, preferably the group of methacrylates with a polyether structure element, wherein none of the further polymerizable monomers is one of those of structure $Q(Y_xZ_e)_b$ according to the above definition under (a1).

in each case in relation to the total weight of the composition.

Greater preference as monomers of the component (a2) are polyethylene glycol di(meth)acrylates with 4 through 10 ethylene oxide units.

Compositions according to the invention, in particular in one of the configurations identified above or below as preferred or particularly preferred, have a good flow and in the cured state a low shrinkage, a good adhesion, a high resistance to hydrolysis, low water absorption, low solubility and suitable mechanical strength (in particular flexural strength and modulus of elasticity). The stated characteristics are in particular important in the area of dental engineering, especially for the filling and/or sealing of a root canal.

Preference is for a composition according to the invention comprising or consisting of:

(a) a monomer component comprising or consisting of
  (a1) in a total quantity of 8 through 30 wt. %, preferably 10 through 20 wt. %,
  (a2) in a total quantity of 8 through 30 wt. %, preferably 10 through 20 wt. %,
(b) one or plurality of initiators and/or catalysts,
(c) a filler component consisting of or comprising
  (c1) one or a plurality of radiopaque fillers in a total quantity in the range 30 through 75 wt. %, preferably in the range 40 through 670 wt. %, more preferably in the range 50 through 70 wt. %, particularly preferably in the range 55 through 65 wt. %,
and optionally one or a plurality of further additives,
wherein the weight percentages given in each case relate to the total weight of the composition.

Further preference is for a composition according to the invention comprising or consisting of:

(a) a monomer component comprising or consisting of
  (a1) in a total quantity of 10 through 20 wt. %, wherein the polymerizable monomers of structure $Q(YZ_e)_b$ (as defined above and wherein each Y is selected independently of any further structure elements Y or is omitted) have a molar mass of less than 2,000 g/mol, (a2) in a total quantity of 10 through 20 wt. %, wherein component (a2) comprises or consists of polyethylene glycol di(meth)acrylates with 4-10 ethylene oxide units,
(b) one or a plurality of initiators and/or catalysts, preferably selected from the group consisting of photoinitiators, hydroperoxides and/or thiourea derivatives,
(c) a filler component consisting of or comprising
   (c1) one or a plurality of radiopaque fillers in a total quantity in the range 40 through 70 wt. %, preferably in the range 50 through 70 wt. %,
and optionally one or a plurality of further additives,
wherein the weight percentages given in each case relate to the total weight of the composition.

Particularly preferred is a composition according to the invention comprising or consisting of:
(a) a monomer component comprising or consisting of
   (a1) in a total quantity of 10 through 20 wt. %, wherein the polymerizable monomers of structure $Q(YZ_e)_b$ (as defined above and wherein each Y is selected independently of any further structure elements Y or is omitted) have a molar mass of less than 1,500 g/mol,
   (a2) in a total quantity of 10 through 20 wt. %, wherein component (a2) comprises or consists of polyethylene glycol di(meth)acrylates with 4 through 10 ethylene oxide units,
(b) one or a plurality of initiators and/or catalysts, preferably selected from the group consisting of photoinitiators, hydroperoxides and/or thiourea derivatives,
(c) a filler component consisting of or comprising
   (c1) one or a plurality of radiopaque fillers in a total quantity in the range 50 through 70 wt. %, preferably in the range 55 through 65 wt. %,
   (c2) one or a plurality of non-radiopaque fillers,
and preferably one, two or a plurality of further additive selected from components (d), (e) and (f)
(d) one or a plurality of molecular weight regulators, preferably selected from the group consisting of α-terpinene, β-terpinene, γ-terpinene, α-phellandrene, β-phellandrene and terpinols, linolenic acid, linoleic acid and substituted or non-substituted cyclohexadienes, preferably in a total quantity in the range 0.025 through 0.75 wt. %,
(e) one or a plurality of active substances selected from the group consisting of remineralizing, therapeutic, devitalizing, disinfecting, inflammation-inhibiting, antibacterial and/or cariostatic active substances,
(f) one or a plurality of adhesion-promoting additives, preferably in a total quantity in the range 0.5 through 2.5 wt. %,
and optionally one or a plurality of further additives,
wherein the weight percentages given in each case relate to the total weight of the composition.

Naturally, for substances which because of their structure at the same time fall under the definition of various components of a composition according to the invention it is the case that for quantitative considerations these substances must be assigned in each case to all these components. For example, where a composition according to the invention contains one or a plurality of further additives of component (f), and this additive at the same time falls under the definition of component (a1) or (a2), for the purpose of quantitative considerations this additive must be assigned to both component (a1) or (a2) and component (f).

Compositions according to the invention comprising a molecular weight regulator (component (d)) have further improved mechanical properties, in particular if the compositions also comprise one or a plurality of non-radiopaque, non-agglomerated nanoscale fillers (component (C2-a), see below). In addition the level of solubility and/r or water absorption can be set very low as a result with simultaneously good flow behavior.

It has further become apparent that a composition according to the invention, in particular a composition according to the invention suitable for filling and/or sealing a root canal, in the cured state has a very low water absorption, preferably less than 50 μg/mm³, preferably less than 40 μg/mm³, and preferably less than 35 μg/mm³, particularly preferably less than 30 μg/mm³. Here the water absorption was determined according to ISO 4049.

Following storage in water of a composition according to the invention under microscopic examination no marginal gaps between the root canal filling and the root canal wall were observed.

In addition it has become apparent that a composition according to the invention, in particular a composition according to the invention suitable for filling and/or sealing a root canal, has a good flow, preferably a flow in the range 20 through 40 mm, in the range 25 through 35 mm. Here the flow was determined according to ISO 6876.

Through the addition of the radiopaque filler(s) as a constituent of component (c1) a composition according to the invention achieves a sufficient radiopacity. The radiopacity is normally measured in aluminum equivalents and given in mm (Al) (see also examples).

The radiopacity of a composition according to the invention is preferably at least 3 mm (Al), preferably it is in the range 3 through 20 mm (Al), preferably in the range 4 through 12 mm (Al). The measurement of the radiopacity takes place according to ISO 4049.

Although root canal sealing and/or filling materials should be easy to remove again from the root canal, it is desirable that the adhesion of the material to the dentin provides the tightest possible seal.

In addition it has become apparent that a composition according to the invention, in particular a composition according to the invention suitable for filling and/or sealing a root canal, routinely has coefficients of adhesion in the range 1 through 4 MPa, preferably in the range 2 through 4 MPa, particularly preferred in the range 2 through 3.8 MPa.

A coefficient of adhesion in the range 1 through 4 MPa is regularly sufficient for the application in the root canal, i.e. as a root canal filling and/or sealing material.

It has become apparent that a preferred composition according to the invention, in particular a composition according to the invention suitable for filling and/or sealing a root canal, has a flexural strength in the range 5 through 30 MPa, preferably a flexural strength in the range 5 through 15 MPa.

It has further become apparent that a preferred composition according to the invention, in particular a composition according to the invention suitable for filling and/or sealing a root canal, has a modulus of elasticity in the range 50 through 800 MPa, preferably in the range 75 through 300 MPa, preferably a modulus of elasticity in the range 80 through 125 MPa.

For a root canal sealing and/or filling material a flexural strength in the range 5 through 20 MPa and a modulus of elasticity of approximately 100 MPa is considered ideal.

The compositions according to the invention must preferably be fashioned in such a way that they can be easily removed from tooth structures and are thus particularly suited to the filling and/or sealing of the root canal.

A curable dental composition according to the invention is therefore preferably suited to used as a root canal filler and/or sealing material.

Constituent (a): Monomer Component

In a composition according to the invention the function of the monomer component (a) is to form a matrix. This matrix is formed by polymerization, in particular radical polymerization of one, two or a plurality of monomers of structure $Q(YZ_e)_b$ (as defined above and wherein each Y is selected independently of any further structure elements Y or is omitted) of component (a1), preferably together with one or a plurality of further monomers of component (a2). The monomer component (a) is preferably a mixture of monomers, which comprises or consists of component (a1) and component (a2).

The polyalicyclic structure element Q of component (a1) here ensures a sterically rigid and hydrophobic spine, while the monomer(s) of components (a2) ensure a specific weakening of the mechanical characteristics (in particular flexural strength and modulus of elasticity).

A combination of component (a1) and component (a2) allows fine adjustment of the characteristics of a composition according to the invention. An intentionally induced weakening of the mechanical characteristics (in particular the flexural strength and modulus of elasticity) of a composition according to the invention (in the cured state) is primarily achieved through the selection and quantity of the constituents used and their components, so that a composition in accordance with the invention in the cured state, in the event of a revision can also be easily removed again from the root canal. This weakening can in particular be achieved by the preferred monomers of the component (a2) and/or by incorporation of one or a plurality of molecular weight regulators of component (f) (see below).

Component (a1): One, Two or a Plurality of Monomers of Structure $Q(YZ_e)_b$ with at Least One Polyalicyclic Structure Element Component (a1) comprises one, two or a plurality of monomers of structure $Q(YZ_e)_b$ defined above (as defined above and wherein each Y is selected independently of any further structure elements Y or is omitted), wherein Z preferably represents a structure element that independently of any further structure elements Z is selected from the group consisting of —O—(C=O)—CH=CH$_2$, —O—(C=O)—C(CH$_3$)=CH$_2$, —(C=O)—CH=CH$_2$ or —(C=O)—C(CH$_3$)=CH$_2$. Preference is for compounds of structure $Q(YZ_e)_b$ (as defined above and wherein each Y is selected independently of any further structure elements Y or is omitted), wherein Z is selected from the group consisting of —O—(C=O)—CH=CH$_2$, —O—(C=O)—C(CH$_3$)=CH$_2$, that is to say those compounds of structure $Q(YZ_e)_b$ (as defined above and wherein each Y is selected independently of any further structure elements Y or is omitted), which have one, two or a plurality of acrylate and/or methacrylate groups, preferably two or a plurality of acrylate and/or methacrylate groups.

The polymers and products obtainable with the monomers of component (a1) according to the invention or to be used according to the invention have a pronounced hydrophobia which inter alia manifests itself in very low water absorption of the polymers and products. Additionally, the polymers obtainable by using the monomers of component (a1) according to the invention or to be used according to the invention are characterized by a suitable mechanical stability which inter alia manifests itself in a suitable flexural strength of the polymers. The monomers of component (a1) according to the invention or to be used according to the invention, in particular according to the particularly preferred configurations and embodiments, lend themselves to processing into polymers which in the cured state have both a low water absorption and a suitable flexural strength.

The monomers of component (a1) are copolymerizable with the further monomers of component (a2), wherein the cured polymers or molding materials have low shrinkage, good adhesion to various substrates, high resistance to hydrolysis, a low water absorption and a suitable mechanical strength. The stated characteristics are particularly important in the area of dental engineering.

The preferred and particularly preferred compounds of component (a1) according to the invention or to be used according to the invention, in particular, allow a high degree of cross-linking and are also preferably radically cross-linkable. Due to their highly functionalized structure they have a high probability of cross-linking and polymerization.

Preferred compounds according to the invention or to be used according to the invention are those wherein Q represents a polyalicyclic structure element, preferably a saturated polyalicyclic structure element, selected from the group consisting of bicyclic and tricyclic hydrocarbon radicals, wherein preferably none of the hydrogen atoms of this polyalicyclic structure element Q not substituted by substituents $YZ_e$ (as defined above and wherein each Y is selected independently of any further structure elements Y or is omitted) is substituted.

Insofar as a compound according to the invention comprises two or a plurality of polyalicyclic structure elements, these may be identical or different.

Particular preference is for monomers $Q(YZ_e)_b$ according to the invention or to be used according to the invention (as defined above and wherein each Y is selected independently of any other structure elements Y or is omitted), the polyalicyclic structure element Q of which is derived from the following tricyclic hydrocarbons: tricyclo[5.2.1.0$^{2,6}$]decane (TCD), tricyclo[5.2.1.0$^{2,6}$]dec-3-ene or tricyclo[3.3.1.1$^{3,7}$]decane (adamantane), i.e. preference is for compounds according to the invention, which have a TCD structure, a tricyclo[5.2.1.0$^{2,6}$]dec-3-ene structure or an adamantane structure.

The stated particularly preferred compounds according to the invention or to be used according to the invention, in which the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical are preferably those with a tricyclo[5.2.1.0$^{2,6}$]decane structure, a tricyclo[5.2.1.0$^{2,6}$]dec-3-ene structure, a tricyclo[3.3.1.1$^{3,7}$]decane structure or a bicyclo[2.2.1]heptane structure, in which in each case none of the hydrogen atoms of this polyalicyclic structure element Q not substituted by substituents $YZ_e$ (wherein each Y is selected independently of any other structure elements Y or is omitted) is substituted.

Particularly preferred compounds according to the invention or to be used according to the invention are those wherein the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical, and particularly preferred the structure element Q represents a tricyclo[5.2.1.0$^{2,6}$]decane radical or a tricyclo[5.2.1.0$^{2,6}$]dec-3-ene radical.

Preference is for the use of methacrylic acid or acrylic acid esters with a tricyclo[5.2.1.0$^{2,6}$]-decane or tricyclo[5.2.1.0$^{2,6}$]-decene structure element, selected from the group consisting of
8,9-bis(acryloxymethyl)tricyclo[5.2.1.0$^{2,6}$]decane
8,9-bis(methacryloyloxymethyl)tricyclo[5.2.1.0$^{2,6}$]decane
8,9-[bis(2-vinyloxyethyl)oxymethyl]tricyclo[5.2.1.0$^{2,6}$]dec-3-ene 8,9-[bis(2-vinyloxyethyl)oxymethyl]tricyclo[5.2.1.0$^{2,6}$]decane
8-hydroxymethyl-9-(2-vinyloxyethyl)oxymethyl]tricyclo [5.2.1.0$^{2,6}$]dec-3-ene
9-hydroxymethyl-8-(2-vinyloxyethyl)oxymethyl]tricyclo [5.2.1.0$^{2,6}$]dec-3-ene
8,9-bis(acryloyloxymethyl)tricyclo[5.2.1.0$^{2,6}$]dec-3-ene
8,9-bis(methacryloyloxymethyl)tricyclo[5.2.1.0$^{2,6}$]dec-3-ene
diacrylic acid esters or dimethacrylic acid esters of compounds selected from the group consisting of:
3,8-dihydroxymethyl-tricyclo[5.2.1.0$^{2,6}$]decane
3,9-dihydroxymethyltricyclo-[5.2.1.0$^{2,6}$]decane
4,8-dihydroxymethyltricyclo[5.2.1.0$^{2,6}$]decane
3,8-dihydroxytricyclo[5.2.1.0$^{2,6}$]decane
3,9-dihydroxytricyclo-[5.2.1.0$^{2,6}$]decane
4,8-dihydroxytricyclo[5.2.1.0$^{2,6}$]decane
methacrylic acid or acrylic acid esters of compounds from the group consisting of:
poly(hydroxymethyl)tricyclo[5.2.1.0$^{2,6}$]decanyl-siloxanes
oxyalkylated bis(hydroxymethyl)tricyclo[5.2.1.0$^{2,6}$]decane
oxyalkylated bishydroxytricyclo[5.2.1.0$^{2,6}$]decane
urethane- or urea groups-containing methacrylic acid or acrylic acid esters of compounds selected from the group consisting of:
3,8-dihydroxymethyl-tricyclo[5.2.1.0$^{2,6}$]decane
4,8-dihydroxymethyl-tricyclo[5.2.1.0$^{2,6}$]decane
3,9-dihydroxymethyl-tricyclo[5.2.1.0$^{2,6}$]decane
4,9-dihydroxymethyl-tricyclo[5.2.1.0$^{2,6}$]decane Here in the stated compounds hydrogen in the tricyclo [5.2.1.0$^{2,6}$]-decane- or tricyclo[5.2.1.0$^{2,6}$]-decene radical can be substituted by alkyl groups (here preferably C1-C4-alkyl), alkoxy groups (here preferably C1-C4-alkoxy), halogen atoms (here preferably F) or trifluoromethyl groups.

A preferred composition according to the invention comprises one, two or a plurality of compounds of structure $Q(YZ_e)_b$ (as defined above and wherein each Y is selected independently of any further structure elements Y or is omitted), having a tricyclo[5.2.1.0$^{2,6}$]-decane radical or a tricyclo [3.3.1.1$^{3,7}$]decane radical, wherein Z is preferably selected from the group consisting of —O—(C=O)—CH=CH$_2$ and —O—(C=O)—C(CH$_3$)=CH$_2$, and particularly Z represents the group —O—(C=O)—C(CH$_3$)=CH$_2$.

Many of the radically polymerizable methacrylic acid or acrylic acid esters listed above with a TCD structure element are known from the prior art.

Our own research has also shown that in particular with the monomers $Q(YZ_e)_b$ (as defined above and wherein each Y is selected independently of any further structure elements Y or is omitted) of component (a1) with a tricyclo[5.2.1.0$^{2,6}$]-decane structure element of component (a1) mentioned above and below compositions with good surface affinity to the root canal wall and low water absorption (preferably less than 40 µg/mm$^3$, preferably less than 35 µg/mm$^3$) can be obtained.

Y is preferably a structure element which in the structure $Q(Y_xZ_e)_b$ links the polyalicyclic structure element Q with e structure elements Z and contains or consists of a structure element that is selected from the group consisting of

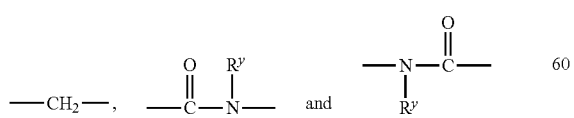

wherein R$^y$ represents another radical of the compound and wherein in each case the bond arranged to the left of the graphic formula is closer to the structure element Q and the bond arranged on the right is closer to the structure element Z.

The other radical R$^y$ of a compound according to the invention or to be used according to the invention is preferably selected from the group consisting of hydrogen, linear, branched or ring-comprising structure elements with 1 through 50 C atoms and 0 through 12 heteroatoms, wherein the heteroatoms that are optionally present optionally are preferably selected from the group consisting of N and O.

The other radical R$^y$ here is preferably selected from the group consisting of hydrogen, linear, branched or ring-comprising structure elements with 1 through 40 C atoms and 0 through 10 heteroatoms, wherein the heteroatoms that are optionally present are preferably selected from the group consisting of N and O.

The other radical R$^y$ here is particularly preferably selected from the group consisting of hydrogen, linear, branched or ring-comprising structure elements with 1 through 35 C atoms and 1 through 10 heteroatoms, wherein the heteroatoms that are optionally present are preferably selected from the group consisting of N and O.

Here Y is preferably a structure element containing or consisting of a structure element selected from the group consisting of

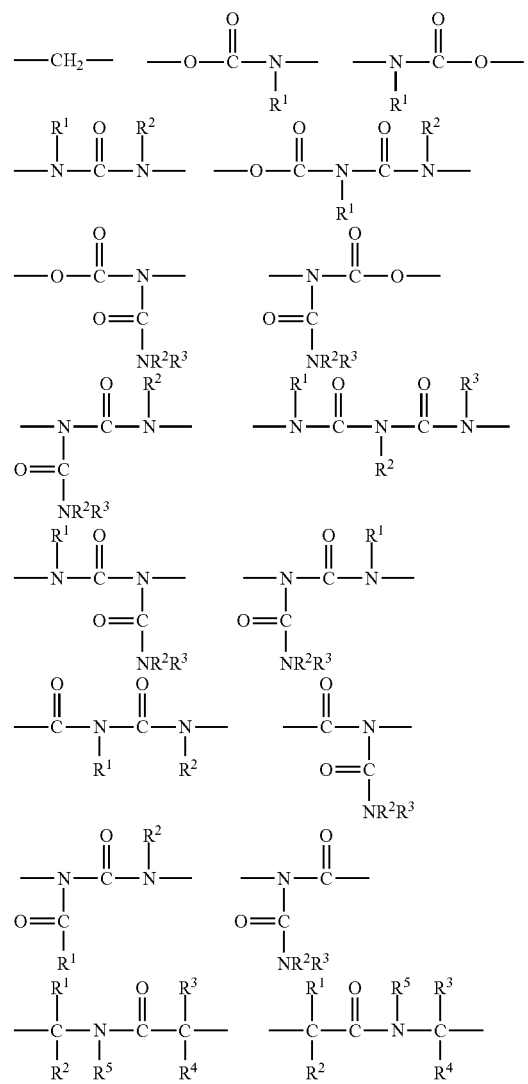

wherein R$^1$, R$^2$, R$^3$R$^4$ and R$^5$ represent other radicals of the compound, wherein in each case the bond arranged to the left of the graphic formula is closer to the structure element Q and the bond arranged on the right is closer to the structure element Z.

The above-mentioned radicals $R^1$, $R^2$, $R^3$, $R^4$ or $R^5$ of a compound according to the invention or a compound to be used according to the invention of structure $Q(Y_xZ_e)_b$ are, in each case independently of one another, preferably selected from the group consisting of hydrogen, linear, branched or ring-comprising structure elements with 1 through 30 C atoms and 0 through 10 heteroatoms, wherein the heteroatoms that are optionally present are preferably selected from the group consisting of N and O.

Here the other radicals $R^1$, $R^2$, $R^3$, $R^4$ or $R^5$, in each case independently of one another, are preferably selected from the group consisting of hydrogen, linear, branched or ring-comprising structure elements with 1 through 25 C atoms and 0 through 8 heteroatoms, wherein the heteroatoms that are optionally present are preferably selected from the group consisting of N and O.

Here the other radicals $R^1$, $R^2$, $R^3$, $R^4$ or $R^5$, in each case independently of one another, are particularly preferably selected from the group consisting of hydrogen, linear, branched or ring-comprising structure elements with 1 through 20 C atoms and 0 through 5 heteroatoms, wherein the heteroatoms that are optionally present are selected from the group consisting of N and O.

In compounds of structure $Q(Y_xZ_e)_b$ according to the invention or to be used according to the invention that can be synthesized with comparatively low effort Y is a structure element, containing a structure element or consisting of this, which is selected from the group consisting of

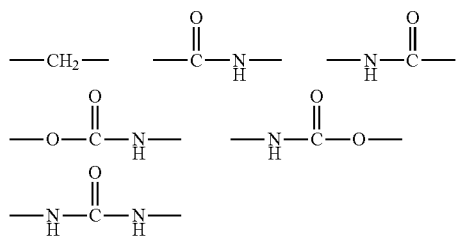

wherein in each case the bond arranged to the left of the graphic formula is closer to the structure element Q and the bond arranged on the right is closer to the structure element Z.

The compounds of structure $Q(Y_xZ_e)_b$ according to the invention or to be used according to the invention can be obtained by the preparation methods known to a person skilled in the art.

Compounds according to the invention or to be used according to the invention of structure $Q(Y_xZ_e)_b$ with an amide structure element can for example be obtained by reacting (i) an educt compound with an isocyanate group and (ii) an educt compound with a carboxylic acid group.

Compounds according to the invention or to be used according to the invention of structure $Q(Y_xZ_e)_b$ with a urethane structure element can for example be obtained by reacting (i) an educt compound with an isocyanate group and (ii) an educt compound with an alcohol group.

Compounds according to the invention or to be used according to the invention of structure $Q(Y_xZ_e)_b$ with a urea structure element can for example be obtained by reacting (i) an educt compound with an isocyanate group and (ii) an educt compound with an amino group.

Compounds according to the invention or to be used according to the invention of structure $Q(Y_xZ_e)_b$ with an allophanate structure element can for example be obtained by reacting (i) an educt compound with a urethane group and (ii) an educt compound with an isocyanate group.

Compounds according to the invention or to be used according to the invention of structure $Q(Y_xZ_e)_b$ with a biuret structure element can for example be obtained by reacting (i) an educt compound with a urea group and (ii) an educt compound with an isocyanate group.

Compounds according to the invention or to be used according to the invention of structure $Q(Y_xZ_e)_b$ with an N-acyl urea structure element can for example be obtained by reacting (i) an educt compound with an amide group and (ii) an educt compound with an isocyanate group.

In a preferred configuration of a composition according to the invention component (b1) is selected so that this comprises or consists of bis(methacryloyloxymethyl)tricyclo[5.2.1.0$^{2,6}$]decane and/or bis(acryloyloxymethyl)tricyclo[5.2.1.0$^{2,6}$]decane.

In compositions according to the invention the methacrylic acid esters, because of their greater biocompatibility are preferred to the corresponding acrylic acid esters, i.e. the Z in compounds of structure $Q(YZ_e)_b$ (as defined above and wherein each Y is selected independently of any further structure elements Y or is omitted) preferably represents —O—(C=O)—C(CH$_3$)=CH$_2$.

Further preferred compounds (monomers) of structure $Q(YZ_e)_b$, (as defined above and wherein each Y is selected independently of any further structure elements Y or is omitted) of component (a1) are those with one, two, three, four or a plurality of functional groups selected from the group consisting of urethane, urea, N-acyl urea, allophanate, biuret and amide, wherein the amide function is not directly linked with an N atom, an O atom or a carbonyl group.

EP 1 238 993 describes a process for the preparation of polyisocyanates containing acyl urea groups and mixtures of these and their use as starting components for the preparation of polyurethane synthetic materials.

EP 0 209 700 A2 and DE 35 22 005 describe (meth)acrylic acid derivatives of certain tricyclodecenes with divalent bridge members from the group of urethanes or ureas, which can be used in the area of dentistry.

EP 0 000 194 A1 (corresponding to U.S. Pat. No. 4,160,080) describes polyisocyanates, containing allophanate groups. These allophanate polyisocyanates may be used for the preparation of polyurethane foams, elastomers, duromers, coatings, adhesives and lacquers.

EP 0 682 012 B1 relates to a process for the preparation of dark-colored, light stable (cyclo-aliphatic) polyisocyanates containing allophanate groups, by reacting organic compounds having urethane groups with organic polyisocyanates with (cyclo)aliphatically bonded isocyanate groups in the presence of tin(II) salts. The polyisocyanates described in EP 0 682 012 B1 can be used as synthesis components in the preparation of polyurethane synthetic materials.

EP1727846 B1 discloses a process for preparation of binding agents containing allophanate groups, comprising groups reacting with ethylenically unsaturated compounds under polymerization under the effects of actinic radiation.

EP 0 712 840 B1 relates to a process for the preparation of certain polyisocyanates comprising allophanate groups through the reaction of compounds comprising urethane groups with the formation of allophanate. The compounds according to EP 0 712 840 B1 can be used as binding agents or binding agent components in coating media.

EP 0 867 457 B1 discloses an ethylenically unsaturated polyurethane, which is essentially free from isocyanate groups, which is the reaction product of an ethylenically unsaturated polyisocyanate, containing allophanate groups and β,γ-ethylenically unsaturated ether groups, with a hydroxyfunctional, ethylenically unsaturated compound, wherein the ethylenically unsaturated polyisocyanate is prepared by allophantization of the urethane groups-containing reaction products of an organic diisocyanate with a β,γ-ethylenically unsaturated ether alcohol, which is selected from the group consisting of glycerin diallyl ether, trimethylolpropane diallyl ether and pentaerythritriallyl ether. Ethylenically unsaturated polyurethanes with allophanate groups disclosed in EP 0 867 457 B1 can be used as binding agents in single component coating compositions.

DE 10 2007 040 240 A1 and EP 1 645 582 A1 in each case describe a process for preparation of radiation-curing allophanates through the reaction of compounds containing isocyanate groups and hydroxyfunctional compounds, wherein the ratio of NCO groups to OH groups is 1.45:1.0 through 1.1:1.0. According to DE 10 2007 040 239 A1 with the use of certain mixtures containing hydroxyethylacrylate and hydroxypropylacrylate as the hydroxyfunctional compounds corresponding radiation-curing allophanates are obtained. The radiation-curing allophanates according to these three documents can be used for the preparation of coatings and lacquers, as well as adhesives, inks, casting resins, dental compounds, release agents, photoresists, stereolithography systems, resins for composites and sealants.

DE 10 2004 060 285 A1 relates to radiation-curable compounds based on a dicidol mixture (containing two or three isomers 3,8-, 4,8- and/or 5,8-bis(hydroxymethyl)tricyclo[5.2.1.0$^{2,6}$]decane) with at least one compound, having at least one ethylenically unsaturated grouping with simultaneously at least one reactive grouping in relation to dicidol, wherein this compound may be a reaction product of hydroxyalkyl(meth)acrylate and diisocyanate. The compositions according to DE 10 2004 060 285 A1 can be used as radiation-induced-curing coating materials, adhesives, laminations, printing and inks, polishes, varnishes, pigment pastes, fillers, cosmetic materials, packaging materials and/or sealing and/or insulating materials.

WO 2006/063891 A1 discloses radically polymerizable compounds, substantially containing the reaction product of a dicidol mixture and at least one compound, which has at least one ethylenically unsaturated grouping with simultaneously at least one reactive grouping in relation to dicidol. The areas of application correspond to those mentioned in DE 10 2004 060 285 A1.

U.S. Pat. No. 6,670,499 B1 describes diurethanes derived from adamantane. The compounds described in U.S. Pat. No. 6,670,499 are suitable as intermediate products for use in dentistry or for producing optical materials (such as lenses, for example).

In the area of dental engineering there is a constant need for more low-shrinkage radically polymerizable monomers. Thus a further problem for the present invention was to provide novel, radically polymerizable monomers, which in a composition according to the invention, in particular in a dental composition according to the invention, can be used as a constituent of component (a1).

This further object is achieved by a compound of structure $Q(YZ_e)_b$ (as defined above and wherein each Y is selected independently of any further structure elements Y) with one, two, three, four or a plurality of functional groups selected from the group consisting of N-acyl urea, allophanate, biuret and amide, wherein the amide function is not directly linked with an N atom, an O atom or a carbonyl group, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups;

b is an integer selected from the group of integers 2, 3, 4;

each Z represents a structure element, which independently of any other structure elements Z is selected from the group consisting of
—O—(C=O)—CH=CH$_2$, —O—(C=O)—C(CH$_3$)=CH$_2$,
—(C=O)—CH=CH$_2$ and —(C=O)—C(CH$_3$)=CH$_2$,
—CH=CH$_2$, —C(CH$_3$)=CH$_2$ and —O—CH=CH$_2$, each index e is an integer, which independently of any other indices e is selected from the group of integers 1, 2, 3 and 4;

each Y represents a structure element, which in the structure $Q(YZ_e)_b$ bonds the polyalicyclic structure element Q with e structure elements Z;

wherein the compound is a first reaction product of a first reaction of

A) a compound of structure $QG_b$, in which each G represents a reactive group, which independently of other groups G is selected from the group consisting of (—CH$_2$)$_n$—NH$_2$, (—CH$_2$)$_n$—(OCH$_2$—CHR)$_m$—OH, (—CH$_2$)$_n$—NCO and (—CH$_2$)$_n$—COOH with B) two or a plurality of identical or different compounds MZ$_e$, wherein M represents a structure element which in each case has one or a plurality of grouping(s) that react with the groups G selected from the group consisting of —NH, —NH$_2$, —OH, —NCO and —COOH, wherein the following applies:

R, in each case independently of any other R, represents a hydrogen atom or an alkyl radical; preferably R represents a hydrogen atom or a linear or branched alkyl radical with 1 through 6 C atoms; more preferably R represents a hydrogen atom or a methyl radical;

m is an integer selected from the group of integers from 0 through 10, each index n is an integer, which independently of any other indices n is selected from the group consisting of 0 and 1, or the compound is a second reaction product from a reaction of the above first reaction product with C) a further compound as claimed in A) or B), wherein each further compound as claimed in A) or B) has the above meaning, independently of what A) and/or B) represent in the first reaction, or the compound is a third reaction product from a reaction of the above second reaction product with D) a further compound as claimed in A) or B), wherein each further compound as claimed in A) or B) has the above meaning, independently of what A) and/or B) represent in the second reaction.

From that stated above it can be inferred that for compounds according to the invention, containing an amide group (as defined) this amide group is not a constituent of the urethane group.

Also preferred are compounds according to the invention of structure $Q(YZ_e)_b$ (as defined above and wherein each Y is selected independently of any further structure elements Y) of component (a1) with one, two, three, four or a plurality of functional groups selected from the group consisting of N-acyl urea, allophanate, biuret and amide, wherein the amide function is not directly linked with an N atom, an O atom or a carbonyl group, wherein the amide in turn preferably represents (meth)acrylamide.

In preferred compounds according to the invention of structure $Q(YZ_e)_b$ (as defined above and wherein each Y is selected independently of any further structure elements Y), the link between Q and at least one structure element takes place via a bridge which contains or consists of a divalent bridge member, selected from the group consisting of

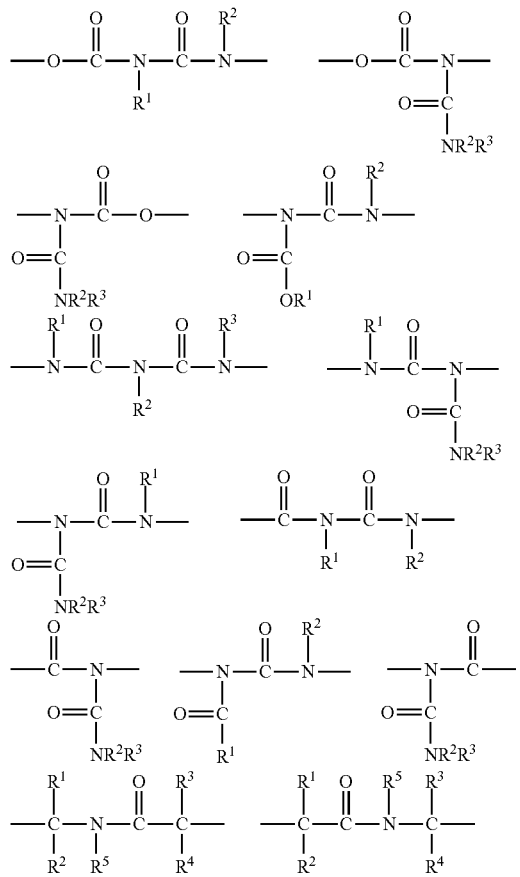

wherein $R^1$, $R^2$, $R^3R^4$, $R^5$ represent other radicals of the compound, wherein in each case the bond arranged to the left of the graphic formula is closer to the structure element Q and the bond arranged on the right is closer to the structure element Z.

The further object is likewise achieved by novel compounds of structure $Q(Y_xZ_e)_b$ with x=1 with one, two, three, four or a plurality of functional groups that are selected from the group consisting of N-acyl urea, allophanate and biuret, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element Q not substituted by substituents $YZ_e$ is or are substituted by alkyl groups, alkoxy groups, halogen atoms or trifluoromethyl groups;

b is an integer selected from the group of integers 2, 3, 4;

each Z represents a structure element, which independently of any further structure elements Z is selected from the group consisting of

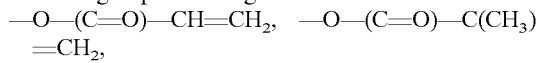
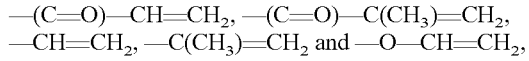

each index e is an integer, which independently of any further indices e is selected from the group of integers 1, 2, 3 and 4;

each Y represents a structure element that in the structure $Q(Y_xZ_e)_e$ with x=1 links the polyalicyclic structure element Q with e structure elements Z and contains or consists of a structure element selected from the group consisting of

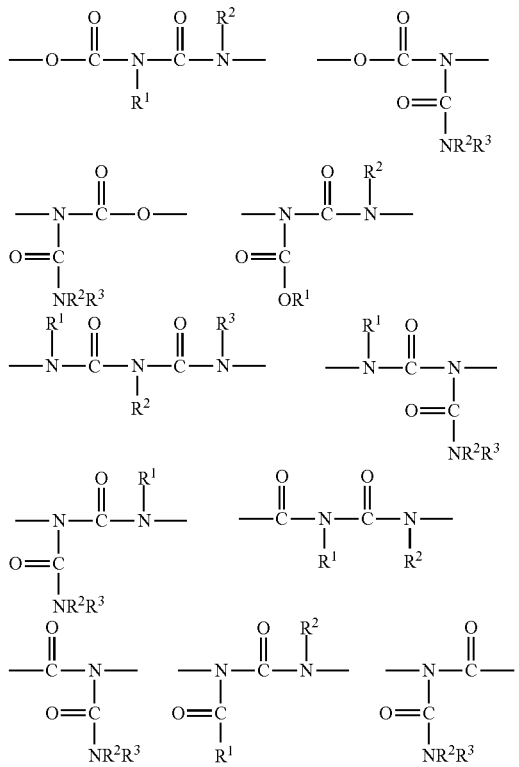

wherein $R^1$, $R^2$, and $R^3$ represent other radicals of the compound, wherein in each case the bond arranged to the left of the graphic formula is closer to the structure element Q and the bond arranged on the right is closer to the structure element Z.

These compounds according to the invention are eminently suitable as monomers for use in compositions according to the invention.

Preferably such a compound according to the invention of structure $Q(Y_xZ_e)_b$ with x=1 comprises two, three, four or a plurality of functional groups selected from the group consisting of N-acyl urea, allophanate and biuret.

In a preferred configuration each index e represents an integer, which independently of any further indices e is selected from the group of integers 2, 3 and 4.

The above-mentioned radicals $R^1$, $R^2$ or $R^3$ of a novel compound according to the invention are, in each case independently of one another, preferably selected from the group consisting of hydrogen, linear, branched or ring-comprising structure elements with 1 through 30 C atoms and 0 through 10 heteroatoms, wherein the heteroatoms that are optionally present are preferably selected from the group consisting of N and O.

The other radicals $R^1$, $R^2$ or $R^3$ of a novel compound according to the invention are, in each case independently of one another, preferably selected from the group consisting of hydrogen, linear, branched or ring-comprising structure elements with 1 through 25 C atoms and 0 through 8 heteroatoms, wherein the heteroatoms that are optionally present are preferably selected from the group consisting of N and O.

The other radicals $R^1$, $R^2$ or $R^3$ of a novel compound according to the invention are, in each case independently of one another, preferably selected from the group consisting of hydrogen, linear, branched or ring-comprising structure elements with 1 through 20 C atoms and 0 through 5 heteroatoms, wherein the heteroatoms that are optionally present are selected from the group consisting of N and O.

A novel compound according to the invention $Q(Y_xZ_e)_b$ with $x=1$, preferably a compound according to the invention $Q(Y_xZ_e)_b$ with $x=1$ as identified above as preferred, can preferably be prepared by reacting a first reaction product, which is the reaction product of a first reaction of A) a compound of structure $QG_b$, in which each G represents a reactive group, which independently of other groups G is selected from the group consisting of $(-CH_2)_n-NH_2$, $(-CH_2)_n-(OCH_2-CHR)_m-OH$, $(-CH_2)_n-NCO$ and $(-CH_2)_n-COOH$ with B) two or more identical or different compounds $MZ_e$, wherein M represents a structure element which in each case has one or more grouping(s) that react with the groups G selected from the group consisting of —NH, —NH$_2$, —OH, —NCO and —COOH, wherein the following applies:

R in each case independently of any further R represents a hydrogen atom or an alkyl radical;

m is an integer selected from the group of integers from 0 through 10, each index n is an integer, which independently of any other indices n is selected from the group consisting of 0 and 1, wherein the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the first and/or second reaction.

A compound according to the invention in a preferred configuration is a second reaction product from a reaction of the above first reaction product with C) a further compound according to A) or B), wherein each further compound according to A) or B) has the same meaning as in the first reaction, and/or wherein the compound is a third reaction product from a reaction of the above second reaction product with D) a further compound according to A) or B), wherein each further compound according to A) or B) has the same meaning as in the first and/or the second reaction, preferably as in the first and the second reaction.

In a first preferred embodiment $m=0$. This applies to all aspects of the present invention.

In preferred compounds according to the invention the link between Q and at least one structure element Z takes place via a bridge which contains or consists of a divalent bridge member, selected from the group consisting of

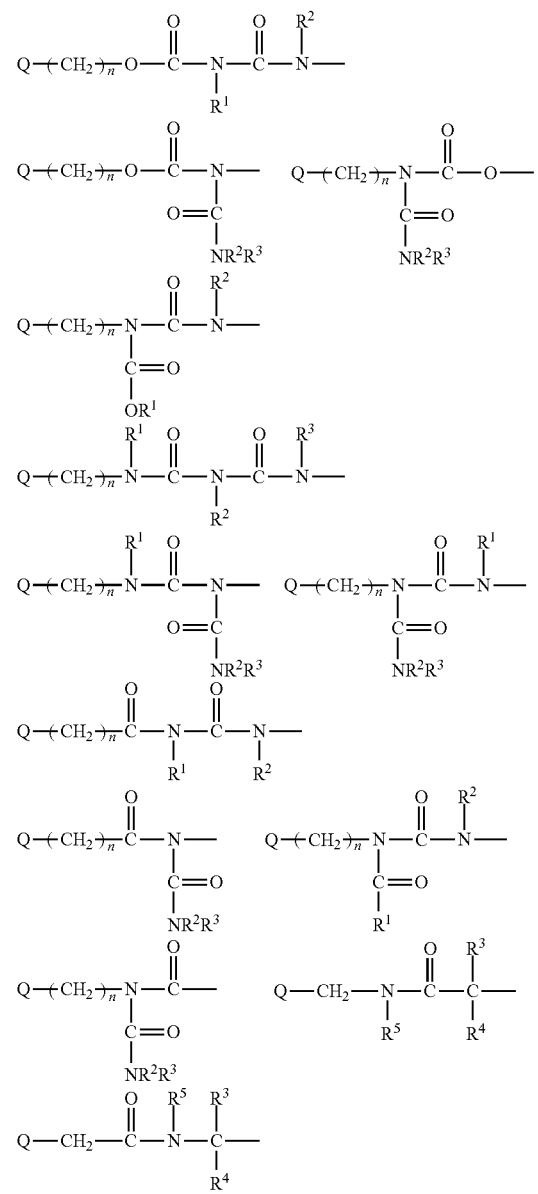

wherein $R^1$, $R^2$, $R^3$, $R^4$, $R^5$ represent other radicals of the compound and Q and the index n have the meaning indicated above.

The bond shown on the right of each graphic formula is nearest to the structure element Z.

In a preferred configuration a novel compound according to the invention $Q(Y_xZ_e)_b$ with x=1, preferably a compound according to the invention $Q(Y_xZ_e)_b$ with x=1 as identified above or below as preferred, comprises one or a plurality of structure elements selected from the group consisting of

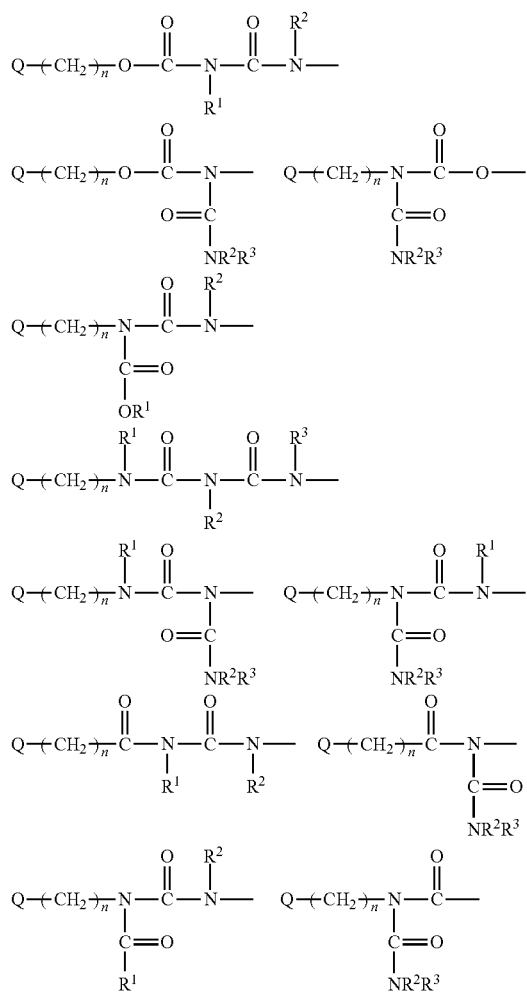

wherein $R^1$, $R^2$ and $R^3$ represent other radicals of the compound (and preferably have the above-mentioned preferred meaning) and Q has the above-mentioned meaning and the index n is selected from the group consisting of 0 and 1.

As already mentioned above preferred novel compounds according to the invention are those wherein Q represents a saturated polyalicyclic structure element, selected from the group consisting of bicyclic and tricyclic hydrocarbon radicals, wherein preferably none of the hydrogen atoms of this polyalicyclic structure element Q not substituted by $YZ_e$ (wherein each Y is selected independently of any further structure elements Y) substituents is substituted.

Particularly preferred novel compounds according to the invention are those wherein the structure element Q represents a tricyclo[$5.2.1.0^{2,6}$]decane radical, a tricyclo [$5.2.1.0^{2,6}$]dec-3-ene radical, a tricyclo[$3.3.1.1^{3,7}$]decane radical or a bicyclo[2.2.1]heptane radical.

Preference is for novel compounds according to the invention in which
(i) the structure element Z represents —O—(C=O)—C (CH$_3$)=CH$_2$, wherein the functional groups are allophanate, biuret or acyl urea groups, since with these compounds particularly good results have been obtained,
and/or
(ii) the structure element Q represents a tricyclo[$5.2.1.0^{2,6}$] decane radical.

Further preference is for novel compounds according to the invention, in which the structure element Z represents —O— (C=O)—C(CH$_3$)=CH$_2$, wherein the functional groups are allophanate, biuret or acyl urea groups and the structure element Q represents a tricyclo[$5.2.1.0^{2,6}$]decane radical.

Preference is for novel compounds according to the invention in which all photocurable groups present correspond to the structure element Z.

Preference is for novel compounds according to the invention in which all terminal polymerizable groups present correspond to the structure element Z.

A novel compound according to the invention, apart from photocurable groups of the structure element Z, can also comprise further polymerizable, preferably terminal polymerizable groups, which are not photocurable, particularly not under the normal conditions that exist in dentistry. This is generally not preferred, however, since such groups do not contribute towards the desired characteristics of the product that exists following polymerization.

Further preferred novel compounds according to the invention are those in which at least one structure element $YZ_e$ is selected independently of the further structure elements $YZ_e$, and preferably all structure elements $YZ_e$ are selected from the group consisting of

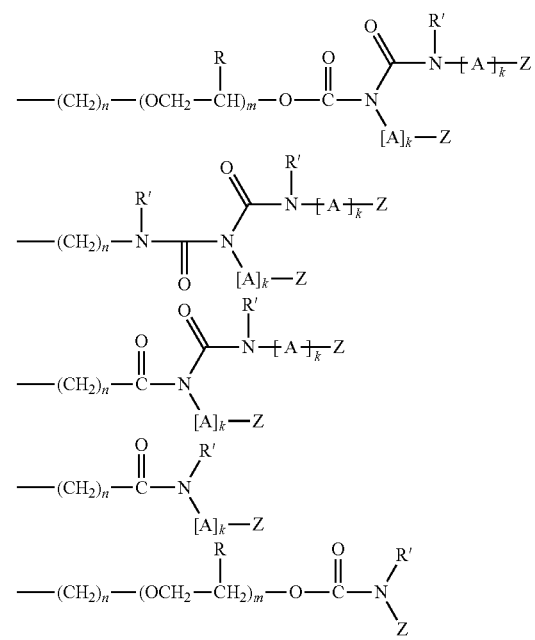

wherein Z, R, m and n have the meaning given above and wherein the following also applies:
each A represents a divalent organic bridge member,
each index k is an integer, which independently of any further indices k is selected from the group consisting of 0 and 1;

each R' represents a structure element which independently of any further structure elements R' is selected from the group consisting of H and a structure element (C=O)—NH-(A)$_k$-Z, wherein A, Z and k in turn have the meanings given above.

In a preferred embodiment m=0.

Similarly preferred compounds according to the invention are those in which at least one structure element YZ$_e$ is selected independently of the further structure elements YZ$_e$, and preferably all structure elements YZ$_e$ are selected from the group consisting of

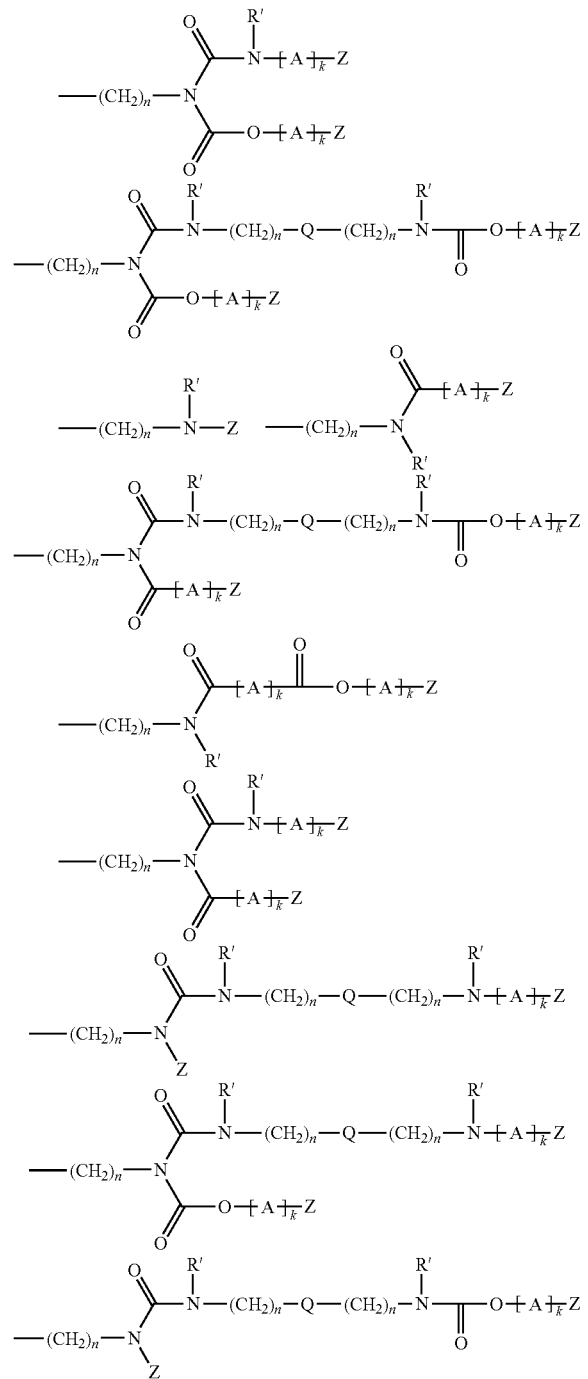

wherein each Q independently of any other structure elements Q has the above meaning and wherein Z, A, k and R', as well as n, have the above meaning.

In a preferred configuration the present invention relates to a compound according to the invention Q(Y$_x$Z$_e$)$_b$ with x=1, preferably a compound according to the invention Q(Y$_x$Z$_e$)$_b$ with x=1 as identified above or below as preferred, wherein at least one structure element YZ$_e$ is selected independently of the further structure element(s) YZ$_e$, and preferably all structure elements YZ$_e$ are selected from the group consisting of

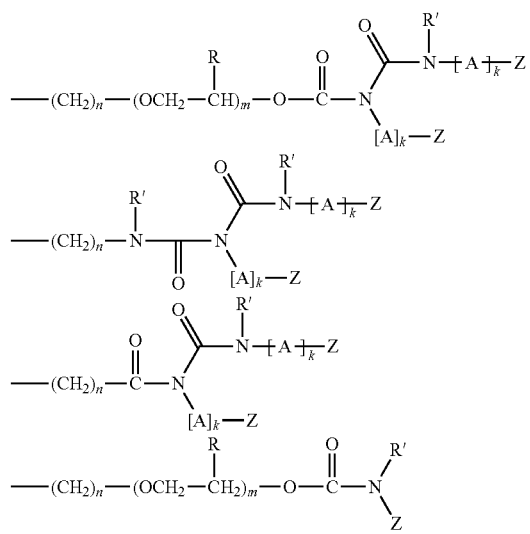

wherein Z, R, m and n have the meaning given above and wherein the following also applies:

each A represents an organic structure element, each index k is an integer, which independently of any further indices k is selected from the group consisting of 0 and 1;

each R' represents a structure element which independently of any further structure elements R' is selected from the group consisting of H and a structure element (C=O)—NH-(A)$_k$-Z, wherein A, Z and k in turn have the meanings given above.

In a preferred configuration the present invention relates to a novel compound according to the invention Q(Y$_x$Z$_e$)$_b$ with x=1, preferably a compound according to the invention Q(Y$_x$-Z$_e$)$_b$ with x=1 as identified above or below as preferred, wherein at least one structure element YZ$_e$ is selected independently of the further structure element(s) YZ$_e$, and preferably all structure elements YZ$_e$ are selected from the group consisting of

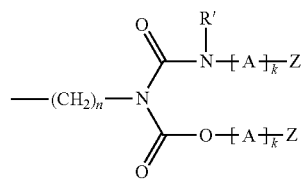

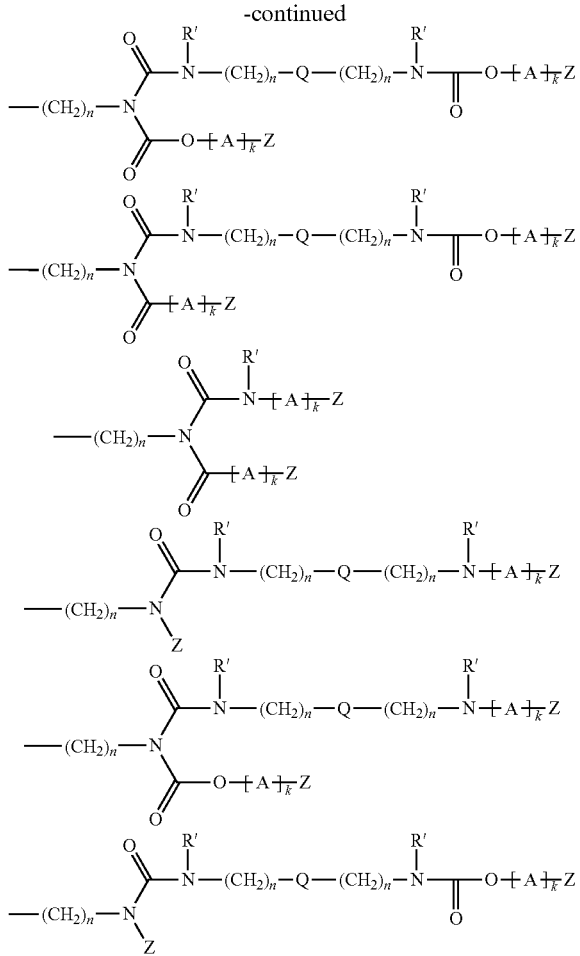

wherein each Q independently of any further structure elements Q has the above meaning, and
wherein Z and n have the above-mentioned meaning and wherein the following also applies:
- each A represents an organic structure element,
- each index k is an integer, which independently of any further indices k is selected from the group consisting of 0 and 1;
- each R' represents a structure element which independently of any further structure elements R' is selected from the group consisting of H and a structure element (C=O)—NH-(A)$_k$-Z, wherein A, Z and k in turn have the meanings given above.

Here in turn preference is for compounds to be used according to the invention in which each structure element A independently of any further structure elements A is selected from the group consisting of all linear, branched or ring-comprising divalent organic bridge members with 1 through 25 C atoms and optionally 1 through 10, preferably 1 through 5 heteroatoms, wherein the heteroatoms that are optionally present are preferably selected from the group consisting of N and O.

Here in turn preference is for a compound according to the invention in which each structure element A independently of any further structure elements A is selected from the group consisting of linear, branched or ring-comprising structure elements with 1 through 25 C atoms and 0 through 10 heteroatoms, preferably with 1 through 5 heteroatoms, wherein the heteroatoms that are optionally present are preferably selected from the group consisting of N and O.

Further preference is for compounds in which each structure element A independently of any further structure elements A is selected from the group consisting of ($C_1$-$C_{20}$) alkylene, ($C_1$-$C_{20}$) heteroalkylene, ($C_3$-$C_{20}$) cycloalkylene, ($C_4$-$C_{20}$) cycloalkylalkylene, ($C_2$-$C_{20}$) alkenylene, ($C_3$-$C_{20}$) cycloalkenylene, ($C_4$-$C_{20}$) cycloalkenylalkylene, ($C_4$-$C_{20}$) cycloalkenylenalkylene, ($C_3$-$C_{25}$) arylene, ($C_2$-$C_{25}$) heteroarylene, ($C_4$-$C_{25}$) arylalkylene, ($C_4$-$C_{25}$) arylenalkylene, ($C_4$-$C_{25}$) arylheteroalkylene, and ($C_4$-$C_{25}$) arylenheteroalkylene.

In preferred configurations structure element A comprises one or a plurality of the following atoms or groups of atoms:
—O—, —O—Ar$^1$—CR$^6$R$^7$—Ar$^2$—O—, —NR$^8$—, —N—(C=O)—, —NH—(C=O)—O—, —NH—C(=O)—NH—
wherein the following applies:
Ar$^1$ and Ar$^2$ independently of each other represent an aromatic ring which is optionally substituted, here preferably once or a plurality of times substituted with C1-C4 alkyl radicals, here in turn preferably a phenyl ring,
R$^6$, R$^7$ and R$^8$ independently of one another represent hydrogen or a C1-C8 radical, here preferably a C1-C4 alkyl radical, here in turn preferably methyl or ethyl.

The present invention further relates to a process for the preparation of compound Q(YZ$_e$)$_b$ according to the invention (wherein each Y is selected independently of any further structure elements Y) or a mixture, comprising at least one such compound Q(YZ$_e$)$_b$ according to the invention, with the following steps:

In a first reaction, reacting
A) a compound of structure QG$_b$, in which each G represents a reactive group, which is selected independently of other G groups from the group consisting of (—CH$_2$)$_n$—NH$_2$, (—CH$_2$)$_n$—(OCH$_2$—CHR)$_m$—OH, (—CH$_2$)$_n$—NCO and (—CH$_2$)$_n$—COOH, preferably a compound of structure QG$_b$, in which each G represents a reactive group, which is selected independently of further G groups from the group consisting of —NH$_2$, —CH$_2$NH$_2$, —OH, —CH$_2$OH, —NCO, —CH$_2$NCO, and —COOH,
with
B) two or according to the invention identical or different compounds MZ$_e$, wherein M represents a structure element which in each case has one or according to the invention grouping(s) that react with the groups G selected from the group consisting of —NH, —NH$_2$, —OH, —NCO and —COOH to form a first reaction product,
optionally in a second reaction, reacting the first reaction product with
C) a further compound according to A) or B), wherein each further compound according to A) or B) has the above meaning, independently of what A) and/or B) represent in the first reaction,
to form a second reaction product,
and optionally in a third reaction, reacting the second reaction product with
D) a further compound according to A) or B), wherein each further compound according to A) or B) has the above meaning, independently of what A) and/or B) represent in the second reaction.
wherein Q, b, Y, Z, and e in each case have the above meanings, and wherein the following applies:
R, in each case independently of any further R, represents a hydrogen atom or an alkyl radical; preferably R represents a hydrogen atom or a linear or branched alkyl radical with 1 through 6 C atoms; more preferably R represents a hydrogen atom or a methyl radical;

m is an integer selected from the group of integers from 0 through 10, each index n is an integer, which independently of any other indices n is selected from the group consisting of 0 and 1, wherein the ratio of the total number of NCO groups to the total number of —$NH_2$, —OH and —COOH in the total number of compounds according to A) and B) in the first, optional second and optional third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

A preferred method according to the invention for preparing a compound according to the invention $Q(Y_xZ_e)_b$ with x=1, preferably a compound according to the invention $Q(Y_x-Z_e)_b$ with x=1 identified above or below as preferred, or a mixture comprising at least one such compound $Q(Y_xZ_e)_b$ is a method with the following steps:

In a first reaction, reacting

A) a compound of structure $QG_b$, in which each G represents a reactive group, which independently of further groups G is selected from the group consisting of (—$CH_2)_n$—$NH_2$, (—$CH_2)_n$—($OCH_2$—$CHR)_m$—OH, (—$CH_2)_n$—NCO and (—$CH_2)_n$—COOH with B) two or a plurality of identical or different compounds $MZ_e$, wherein M represents a structure element which in each case has one or a plurality of grouping(s) that react with the groups G selected from the group consisting of —NH, —$NH_2$, —OH, —NCO and —COOH to form a first reaction product, in a second reaction, reacting the first reaction product with C) a further compound according to A) or B), wherein each further compound according to A) or B) has the above meaning, independently of what A) and/or B) represent in the first reaction, to form a second reaction product, and optionally in a third reaction, reacting the second reaction product with D) a further compound according to A) or B), wherein each further compound according to A) or B) has the above meaning, independently of what A) and/or B) represent in the second reaction.

wherein Q, b, Y, Z, e, M, R, m and n in each case have the above meanings, and wherein the ratio of the total number of NCO groups to the total number of —$NH_2$, —OH and —COOH in the total number of compounds according to A) and B) in the first, the second and optional third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

In a method according to the invention for preparation of a compound according to the invention $Q(Y_xZ_e)_b$ with x=1, preferably a compound according to the invention $Q(Y_xZ_e)_b$ with x=1 identified above or below as preferred, or a mixture comprising at least one such compound $Q(Y_xZ_e)_b$, the ratio of the total number of NCO groups reacted to the total number of —$NH_2$, —OH and —COOH reacted in the total number of compounds according to A) and B) in the first, second and optional third reaction is preferably in the range 1.1:1 through 5:1, more preferably in the range 1.25:1 through 4:1, particularly preferably in the range 1.5:1 through 3:1, and most preferably in the range 2:1 through 2.5:1.

Preferably the reaction to the first reaction product, to the second reaction product and/or to the third reaction product takes place in the presence of a catalyst.

Preferred catalysts here are tertiary amines or Lewis acids, here in turn preference is for metal salts of higher fatty acids, in particular dibutyltin dilaurate or tin (II) octoate.

The quantity of catalyst here is preferably in the range 0.01 through 2 wt. %, preferably 0.08 through 1 wt. %, in relation to the total quantity of reactants according to A) and B) and optionally C) and optionally D).

The reaction to the first reaction product, to the second reaction product and/or the third reaction product preferably takes place in a temperature range of 0 through 160° C., preferably in the range 30 through 140° C. and particularly preferably in the range 60 through 120° C. The reaction is preferably carried out at normal pressure (1013 mbar).

In a further aspect the present invention relates to a mixture comprising one, two or a plurality of different compounds according to the invention preparable using a method according to the invention.

In a further aspect the present invention relates to the use of a compound according to the invention, preferably in one of the configurations identified as preferred or particularly preferred, for the preparation of a dental composition, preferably for preparation of a composition according to the invention.

In a further aspect the present invention relates to the use of a compound according to the invention, preferably in one of the configurations identified as preferred or particularly preferred, in a dental composition.

In a further aspect the present invention relates to the use of a compound according to the invention, preferably in one of the configurations identified as preferred or particularly preferred, in a composition suitable for filling and/or sealing a root canal, preferably in one of the configurations identified as preferred or particularly preferred.

For the preparation of the compounds according to the invention preferably hydroxyl compounds of (meth)acrylates can be used, wherein mixtures of acrylates and methacrylates can also be used. Preference (for use as reaction partners according to components B), C) and/or D)) is for:

alkylene oxide mono(meth)acrylates such as for example ethylene glycol mono(meth)acrylate, diethylene glycol mono (meth)acrylate, triethylene glycol mono(meth)acrylate, tetraethylene glycol mono(meth)acrylate, etc., polyalkylene oxide mono(meth)acrylates such as for example polyethylene glycol mono(meth)acrylate, polypropylene glycol mono (meth)acrylate, polybutylene glycol mono(meth)acrylate, etc., hydroxyalkyl mono(meth)acrylates such as for example hydroxyethyl(meth)acrylate, hydroxypropyl(meth)acrylate, 2-hydroxypropyl(meth)acrylate, hydroxybutyl(meth)acrylate, 4-hydroxybutyl(meth)acrylate, hydroxypentyl(meth) acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate, hydroxydodecyl(meth)acrylate, etc., poly(ε-caprolactone)mono(meth)acrylate, poly(γ-caprolactone)mono(meth) acrylate, etc., the mono-, di-, tetra-, or penta(meth)acrylates of polyhydric alcohols, such as glycerin, such as for example glycerin di(meth)acrylate (2-hydroxypropyl-1,3-di(meth) acrylate, 3-hydroxypropyl-1,2-di(meth)acrylate), such as trimethylolpropane, such as for example trimethylolpropane di(meth)acrylate, such as pentaerythritol, such as for example pentaerythritoltri(meth)acrylate, such as dipentaerythritol, such as for example dipentaerythritolpenta(meth)acrylate, such as ditrimethylolpropantri(meth)acrylate, such as neopentyl glycol(meth)acrylate, the (meth)acrylates of alkoxylated or phenoxylated glycerin, here preferably the (meth)acrylates of ethoxylated, propoxylated, etc. glycerin, trimethylolpropane, pentaerythritol, dipentaerythritol, ditrimethylolpropane, etc. and the technical mixtures thereof, bisphenol-A-glycidyl-(meth)acrylate (Bis-GMA), bisphenol-B-glycidyl-(meth)acrylate, bisphenol-C-glycidyl-(meth)acrylate, bisphenol-F-glycidyl-(meth)acrylate, alkoxylated bisphenol-A-glycidyl-(meth)acrylate (e.g. ethoxylated bisphenol-A-glycidyl-(meth)acrylate), etc.

For the preparation of the compounds according to the invention as component B) isocyanates can also be used. Preference here is for mono- and diisocyanates.

Preferred diisocyanates are selected from the group consisting of cyclohexane diisocyanate, methylcyclohexane diisocyanate, ethylcyclohexane diisocyanate, propylcyclohexane diisocyanate, methyldiethylcyclohexane diisocyanate, phenylene diisocyanate, toluoylene diisocyanate, bis(isocyanatophenyl)methane, propane diisocyanate, butane diisocyanate, pentane diisocyanate, hexane diisocyanate, such as hexamethylene diisocyanate or 1,5-diisocyanato-2-methyl pentane, heptane diisocyanate, octane diisocyanate, nonane diisocyanate, such as 1,6-diisocyanato-2,4,4-trimethylhexane or 1,6-diisocyanato-2,2,4-trimethylhexane, nonane triisocyanate, such as 4-isocyanatomethyl-1,8-octane diisocyanate, decane di- and triisocyanate, undecane di- and -triisocyanate, dodecandi- and -triisocyanates, isophorone diisocyanate, dicyclohexylmethane-4,4'-diisocyanate, isocyanatomethylmethylcyclohexyl isocyanate, 1,3-bis(isocyanatomethyl)cyclohexane or 1,4-bis(isocyanatomethyl)cyclohexane.

Preferred monoisocyanates are (meth)acryloyl isocyanate and (meth)acryl-C2-C8-alkyl isocyanates (e.g. (meth)acrylalkyl isocyanates with alkyl spacers, having 2 through 8, particularly preferably 2 through 6 carbon atoms), here in turn preference is for (meth)acryl ethyl isocyanate (2-isocyanatoethyl(meth)acrylate).

Furthermore, as component B) monoisocyanates have proven to be an advantage that are the reaction products of amino- or hydroxyalkyl(meth)acrylates, the alkyl spacers of which have 1 through 12, preferably 2 through 8, particularly preferred 2 through 6 carbon atoms, and diisocyanates.

Preferably to this end a diisocyanate mentioned above is reacted in equimolar proportions with an amino- or hydroxylalkyl compound (indicated above as preferred) of a (meth)acrylate, wherein the hydroxylalkyl compounds in turn are preferably selected from the group consisting of hydroxyethyl(meth)acrylate, hydroxypropyl(meth)acrylate, hydroxybutyl(meth)acrylate, hydroxypentyl(meth)acrylate and hydroxyhexyl(meth)acrylate.

Quoted examples are the reaction products in the molar ratio of 1:1 of hydroxyethylmethacrylate and isophorone diisocyanate, dicyclohexylmethane-4,4'-diisocyanate or hexamethylene diisocyanate.

In the following the invention is initially explained in detail for monomers comprising tricyclic structure elements Q using the example of tricyclo[5.2.1.0$^{2,6}$]decane (TCD)-derivatives.

1.) Starting with the bis(hydroxymethyl)tricyclo[5.2.1.0$^{2,6}$]decane (TCD-diol)

bis(hydroxymethyl)tricyclo[5.2.1.0$^{2,6}$]decane is commercially available, for example as a dicidol mixture of the isomeric compounds 3,8-bis(hydroxymethyl)tricyclo[5.2.1.0$^{2,6}$]decane and 4,8-bis(hydroxymethyl)tricyclo[5.2.1.0$^{2,6}$]decane as well as 3,9-bis(hydroxymethyl)tricyclo[5.2.1.0$^{2,6}$]decane and 4,9-bis(hydroxymethyl)tricyclo[5.2.1.0$^{2,6}$]decane.

The bis(hydroxymethyl)tricyclo[5.2.1.0$^{2,6}$]decanes can, starting with dicyclopentadiene (tricyclo[5.2.1.0$^{2,6}$]deca-3,8-diene), be synthesized. Dicyclopentadiene is easily accessible in a Diels-Alder reaction by dimerization of cyclopentadiene. Hydroformylation of dicyclopentadiene then produces the bis(hydroxymethyl)tricyclo[5.2.1.0$^{2,6}$]decane. According to the synthesis route taken bis(hydroxymethyl)tricyclo[5.2.1.0$^{2,6}$]decanes specifically substituted at different positions can be obtained. Thus in published documents JP 7-206740, EP 1112995 B1 or EP 0049631 B1 specifications are provided on how, for example, the 8,9-bis(hydroxymethyl)tricyclo[5.2.1.0$^{2,6}$]decane is prepareable. DE 10352260 B3 on the other hand describes a method for preparing 3(4),8(9)-bis(hydroxymethyl)tricyclo[5.2.1.0$^{2,6}$]decane. The notation of the positions of the hydroxymethyl groups 3(4), 8(9) means 3 or 4, 8 or 9.

The commercially available starting compound that can be used for the preparation of monomers according to the invention, bis(hydroxymethyl)tricyclo[5.2.1.0$^{2,6}$]decane, thus contains hydroxymethyl groups both at positions 3 or 4 and in positions 8 or 9. It is now possible by addition of alkylene oxides, in general in quantities of 1 through 10 mol, particularly of ethylene oxide, propylene oxide, butylene oxide, etc. in the presence of basic catalysts and according to known methods to synthesize the corresponding polyether polyols. EP0023686 B1 contains more detailed preparation specifications in this connection.

The reaction of the 3(4),8(9)-bis(hydroxymethyl)tricyclo[5.2.1.0$^{2,6}$]decanes with isocyanates to form the corresponding urethanes is likewise known. Thus DE 3522006 A1 describes the reaction of the 3(4),8(9)-bis(hydroxymethyl)tricyclo[5.2.1.0$^{2,6}$]decane with 2-isocyanatoethyl methacrylate. 2-isocyanatoethyl methacrylate is commercially available or can be synthesized according to the preparation specification from DE 3338077 A1 by phosgenation of dihydrooxazines.

The reaction product obtained (Formula (1)) of 2-isocyanatoethyl methacrylate with 3(4),8(9)-bis(hydroxymethyl)tricyclo[5.2.1.0$^{2,6}$]decane in a formulation following curing has a lower reaction shrinkage.

Formula (1)

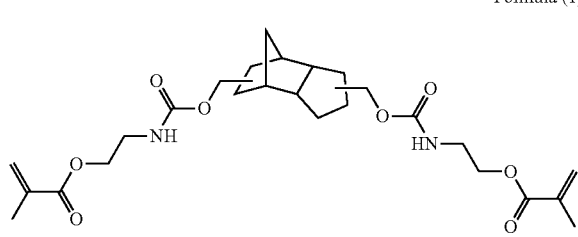

The urethane of Formula (1) still has two hydrogen atoms capable of reacting with nitrogen, which now in a second reaction stage are further reacted with excess isocyanate to form a compound according to the invention. In the process the allophanate of Formula (2) initially forms as a tetrafunctionalized radically cross-linkable compound. In turn this monomer also still has hydrogen atoms capable of reacting with nitrogen, which according to the invention when reacting with further isocyanate form the hexafunctionalized, radically curable allophanate of Formula (3).

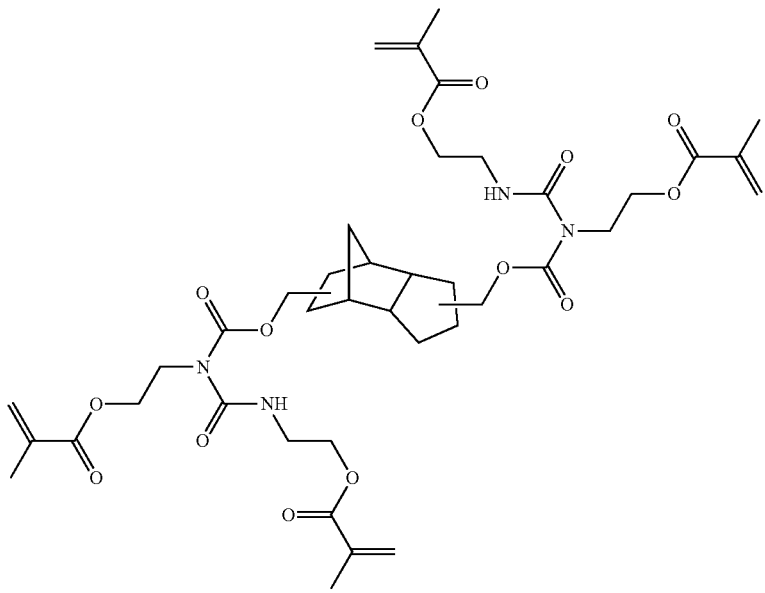

Formula (2)

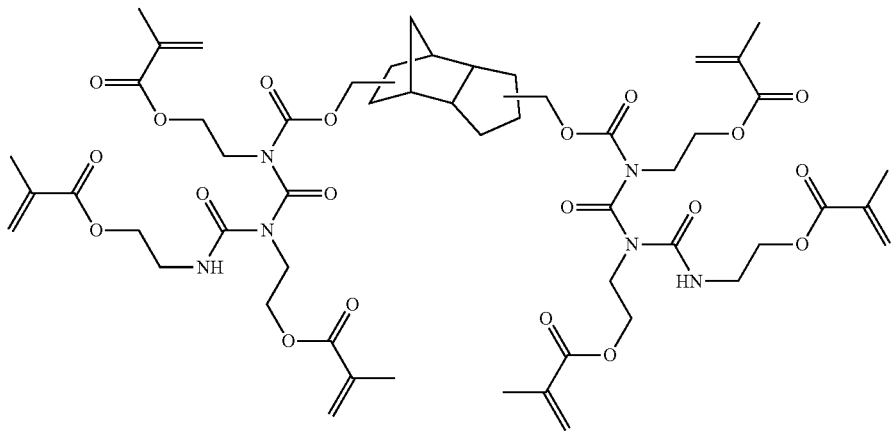

Formula (3)

Alternatively the 3(4),8(9)-bis(hydroxymethyl)tricyclo[5.2.1.0$^{2,6}$]decane can also be brought into a reaction with methacryloyl isocyanate. Methacryloyl isocyanate is commercially available or can be obtained by reacting methacrylamide with oxalyl chloride, as described in EP 0143613 B1. Through the reaction of 3(4),8(9)-bis(hydroxymethyl)tricyclo[5.2.1.0$^{2,6}$]decane with methacryloyl isocyanate a compound of Formula (4) is obtained:

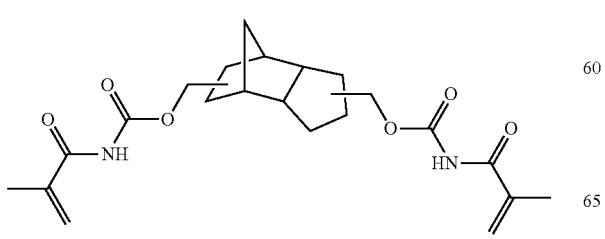

Formula (4)

The remaining hydrogen atoms able to react with nitrogen of the compound of Formula (4) can then in turn be reacted in isocyanate reactions to form allophanates. The reaction product with 2-isocyanatoethyl methacrylate (Formula (5)) is shown here as an example.

Formula (5)

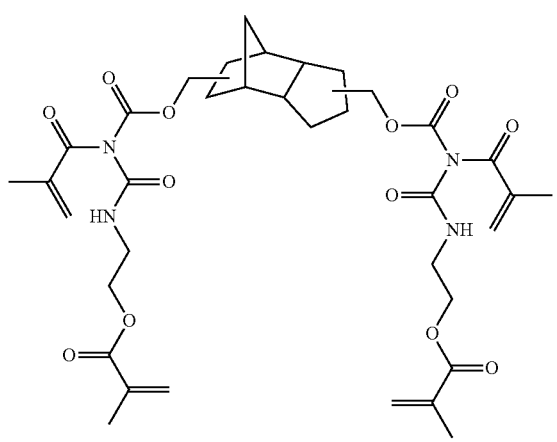

2.) Starting with 3(4),8(9)-bis(carboxylic acid)tricyclo[5.2.1.0$^{2,6}$]decane

The 3(4),8(9)-bis(carboxylic acid)tricyclo[5.2.1.0$^{2,6}$]decane is prepareable by simple oxidation of the commercially available 3(4),8(9)-bis(formyl)tricyclo[5.2.1.0$^{2,6}$]decane. Reaction of the dicarboxylic acid with 2-isocyanatoethyl methacrylate produces the amide of Formula (8):

Formula (8)

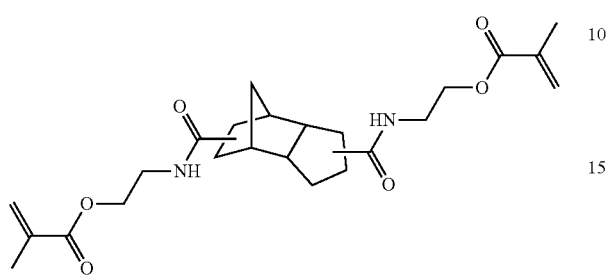

Further reaction of the two amide-hydrogen atoms of the amide of Formula (8) capable of reacting with 2-isocyanatoethyl methacrylate produces the acyl urea of Formula (9).

Formula (9)

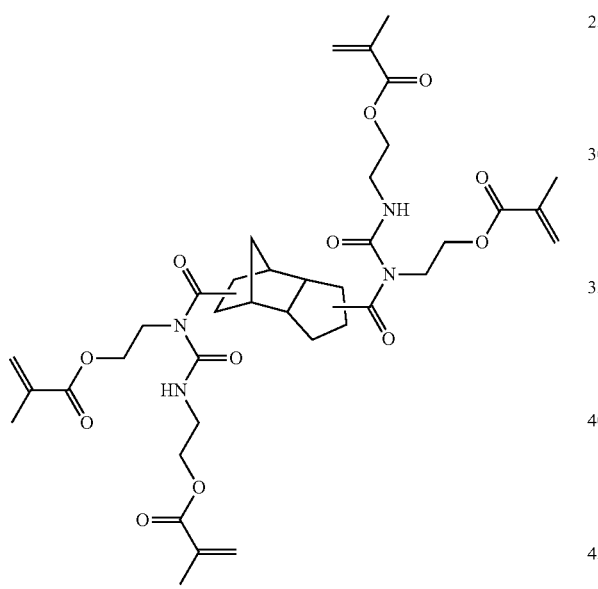

If 3(4),8(9)-bis(carboxylic acid)tricyclo[5.2.1.0$^{2,6}$]decane is reacted with methacryloyl isocyanate, the imide of Formula (10) results. The hydrogen atoms that react with nitrogen can here also be further reacted in isocyanate reactions.

Formula (10)

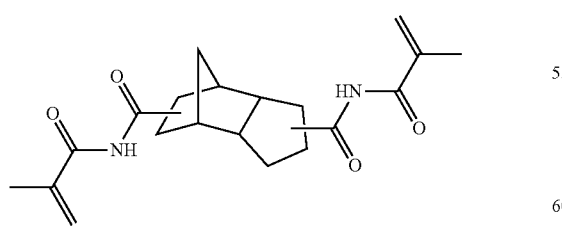

3.) Starting with 3(4),8(9)-bis(isocyanatomethyl)tricyclo[5.2.1.0$^{2,6}$]decane The 3(4),8(9)-bis(isocyanatomethyl)tricyclo[5.2.1.0$^{2,6}$]decane is in itself known and is one of the diisocyanate compounds commonly used in industrial applications (see DE 3703120 A1 and WO 2009/065873 A2). The conducting according to the invention of the second reaction stage of the isocyanate-alcohol reaction can be initiated not only starting with tricyclodecandiol and the isocyanatoethyl methacrylate, but also starting with the tricyclodecane diisocyanate and hydroxyethyl methacrylate. Through stoichiometric reaction of the two reactants the urethane of Formula (11) is obtained.

(Formula 11)

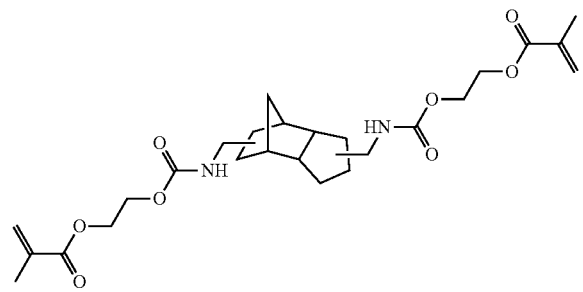

This carbamate (Formula (11)) also has two hydrogen atoms capable of reacting with nitrogen, which can be further reacted with an excess of bis(isocyanatomethyl)tricyclo[5.2.1.0$^{2,6}$]decane to form the diisocyanate of Formula (12).

Formula (12)

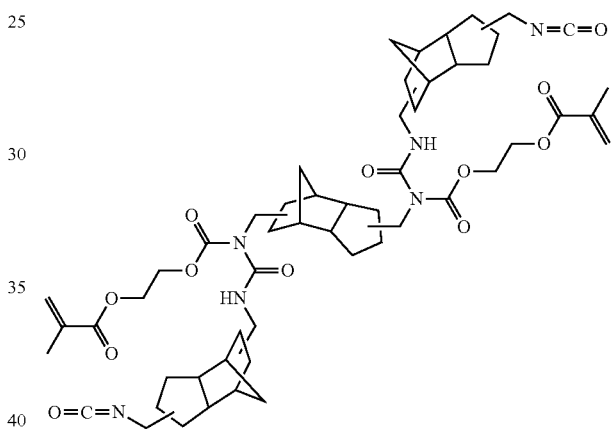

Reaction of the allophanate diisocyanate (Formula 12) with methacrylic acid produces the compound of Formula (13).

Formula (13)

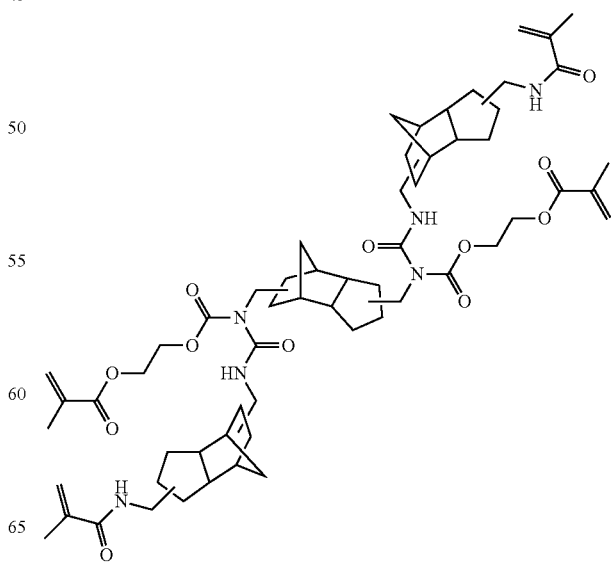

Instead of hydroxyethyl methacrylate in the reactions described by way of example above other hydroxyl compounds of (meth)acrylates can be used, wherein mixtures of acrylates and methacrylates can also be used. So—analogously to the above example—3(4),8(9)-bis(isocyanatomethyl)tricyclo[5.2.1.0$^{2,6}$]decane can be reacted. Here, preferred hydroxyl compounds of (meth)acrylates are those expressly mentioned above.

These compounds have both (meth)acrylate groups and hydroxy groups. The latter can react with isocyanate groups in the manner described above for the reaction between hydroxyethyl methacrylate and 3(4),8(9)-bis(isocyanatomethyl)-tricyclo[5.2.1.0$^{2,6}$]decane. Thus in a single reaction step a high degree of functionalization can be achieved.

3(4),8(9)-bis(isocyanatomethyl)tricyclo[5.2.1.0$^{2,6}$]decane can be reacted with 2-carboxylic acid-methacrylate to form the corresponding amide of Formula (16).

Formula (16)

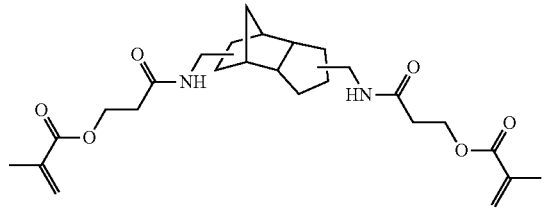

Reacting of the amide of Formula (16) with 2-isocyanatoethyl methacrylate produces the acyl urea of Formula (17).

Formula (17)

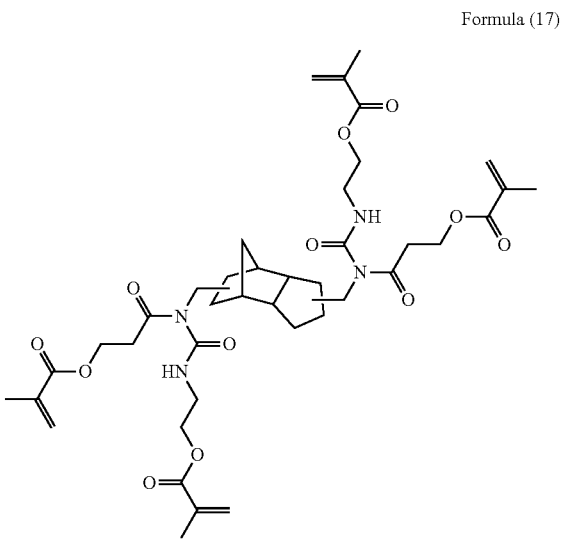

The amide of Formula (16) can also be reacted with an excess of 3(4),8(9)-bis(isocyanatomethyl)tricyclo[5.2.1.0$^{2,6}$]decane to form the corresponding isocyanate, wherein the isocyanate so formed is further reacted with hydroxyethyl methacrylate to form the cross-linkable monomer of Formula (18).

Formula (18)

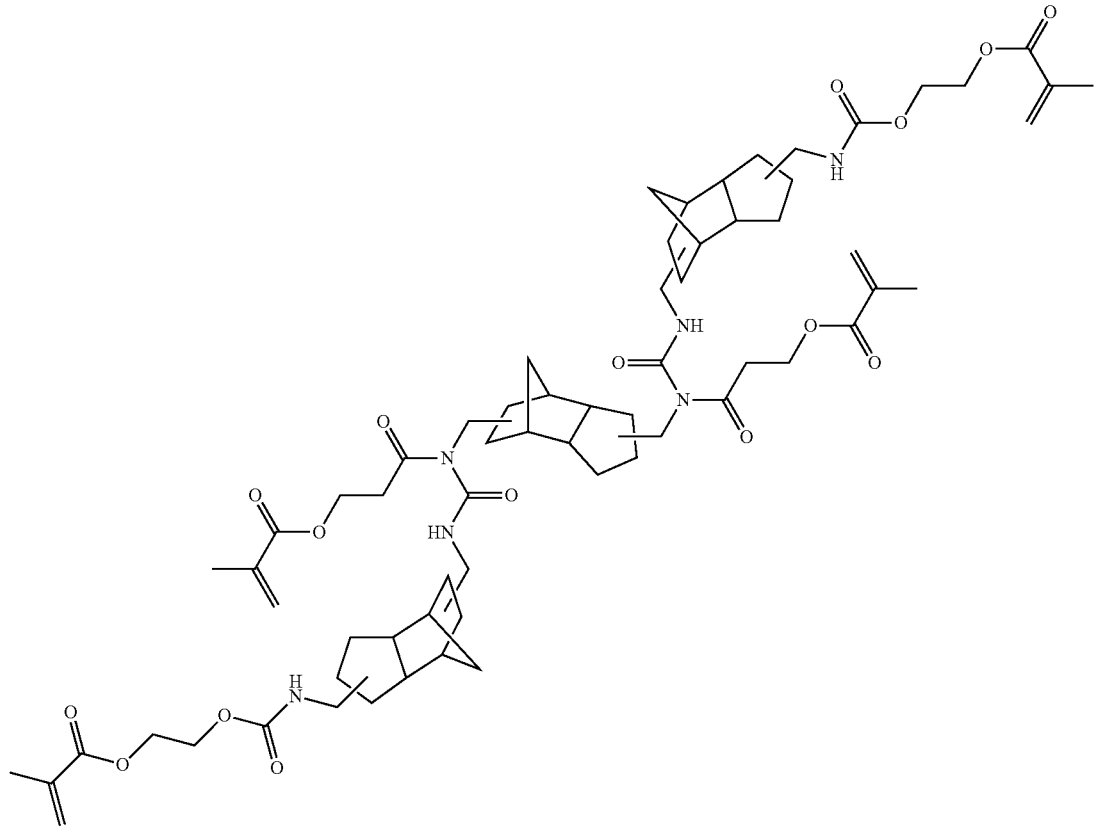

If 3(4),8(9)-bis(isocyanatomethyl)tricyclo[5.2.1.0$^{2,6}$]decane is reacted with 2-methacryloyloxy ethyl hydrogen succinate, then the amide of Formula (19) is obtained, which is further reacted with 2-isocyanatoethyl methacrylate to form the acyl urea of Formula (20).

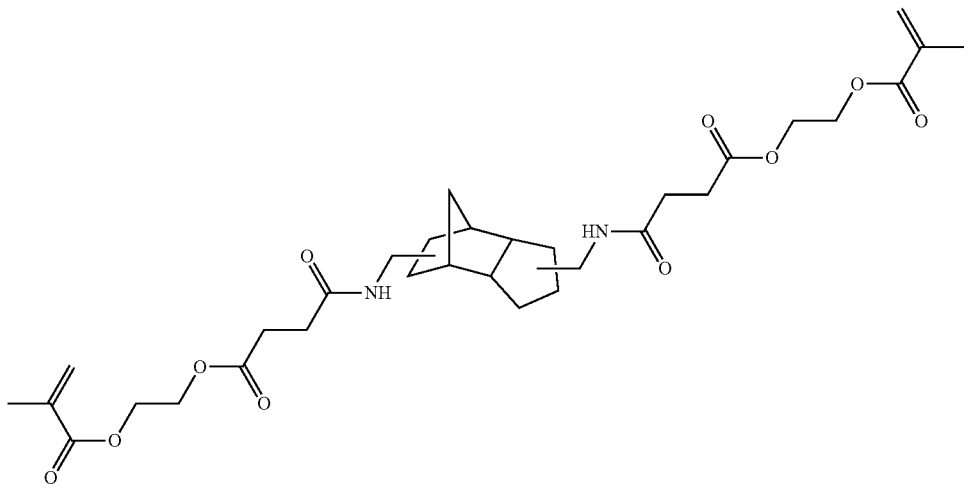

Formula (19)

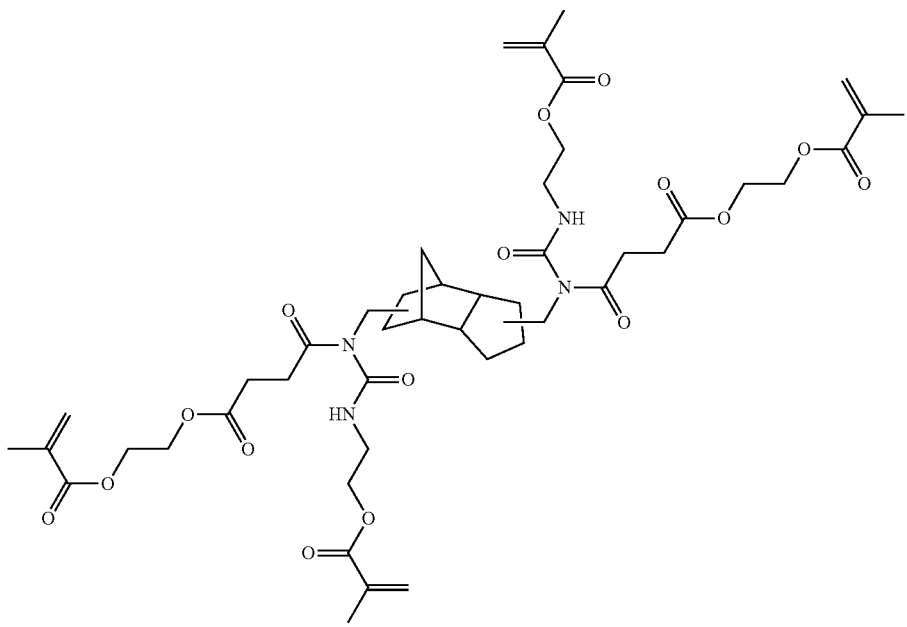

Formula (20)

Further suitable carboxylic acid methacrylates can be obtained from reactions between di- or tetracarboxylic acid mono- or dianhydride with suitable OH-functionalized, curable compounds such as for example 2-hydroxyethyl methacrylate.

4.) Starting with 3(4),8(9)-bis(aminomethyl)tricyclo[5.2.1.0$^{2,6}$]decane

The 3(4),8(9)-bis(aminomethyl)tricyclo[5.2.1.0$^{2,6}$]decane is in itself known or can be prepared for example by reaction of the corresponding tosylates with ammonia. Reaction of the 3(4),8(9)-bis(aminomethyl)tricyclo[5.2.1.0$^{2,6}$]decane with 2-isocyanatoethyl methacrylate results in the urea compound of Formula (26) known from EP 0209700 A2.

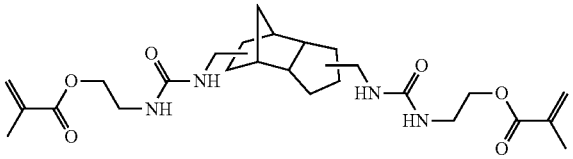

Formula (26)

Here again, there are still active hydrogen atoms capable of reacting with nitrogen which for example with an excess of isocyanate react to form the biuret of Formula (27).

Formula (27)

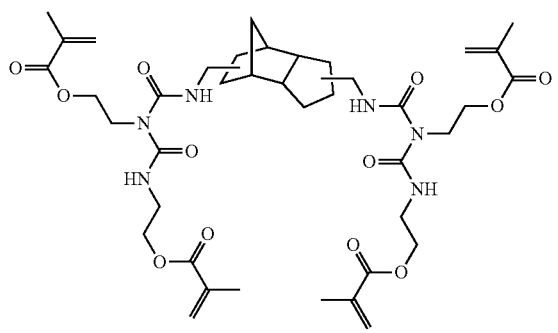

The 3(4),8(9)-bis(aminomethyl)tricyclo[5.2.1.0$^{2,6}$]decane can also be brought into a reaction with methacryloyl isocyanate to form the corresponding acyl urea. The further reaction of the remaining hydrogen atoms reactive to nitrogen with methacryloyl isocyanate provides the biuret of Formula (28).

Formula (28)

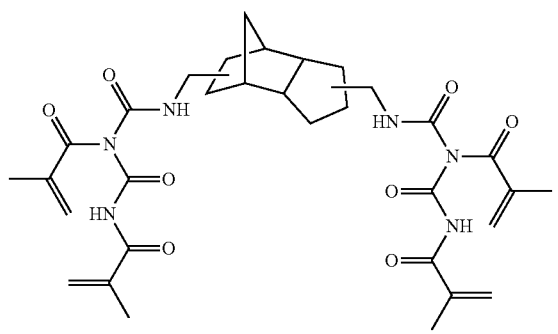

By analogy to the monomers described above, which comprise a polyalicyclic structure element Q derived from the tricyclo[5.2.1.0$^{2,6}$]decane, monomers can also be prepared, which comprise a polyalicyclic structure element Q derived from a tricyclo[3.3.1.1$^{3,7}$]decane (adamantane). The following reaction products are shown by way of examples:

Formula (29)

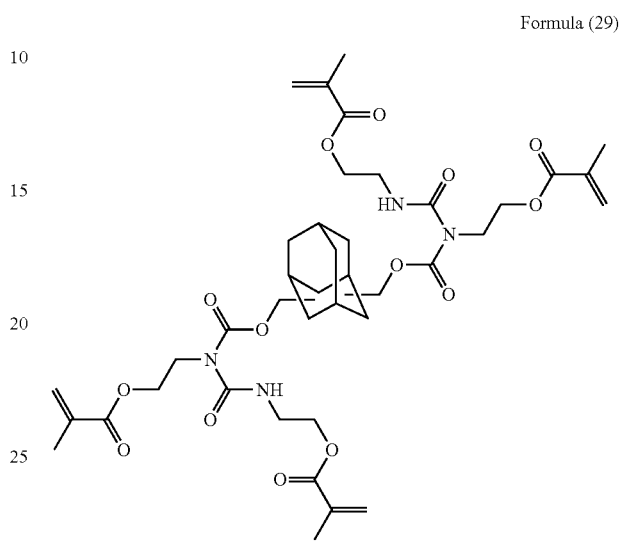

The reaction of the compound of Formula (11) with diisocyanatoadamantane [(bis(isocyanatomethyl)tricyclo[3.3.1.1$^{3,7}$]decane] provides a monomer according to the invention, the molecule of which comprises two polyalicyclic structure elements that differ from one another, as shown in the following graphic formula of the compound of Formula (69).

Formula (69)

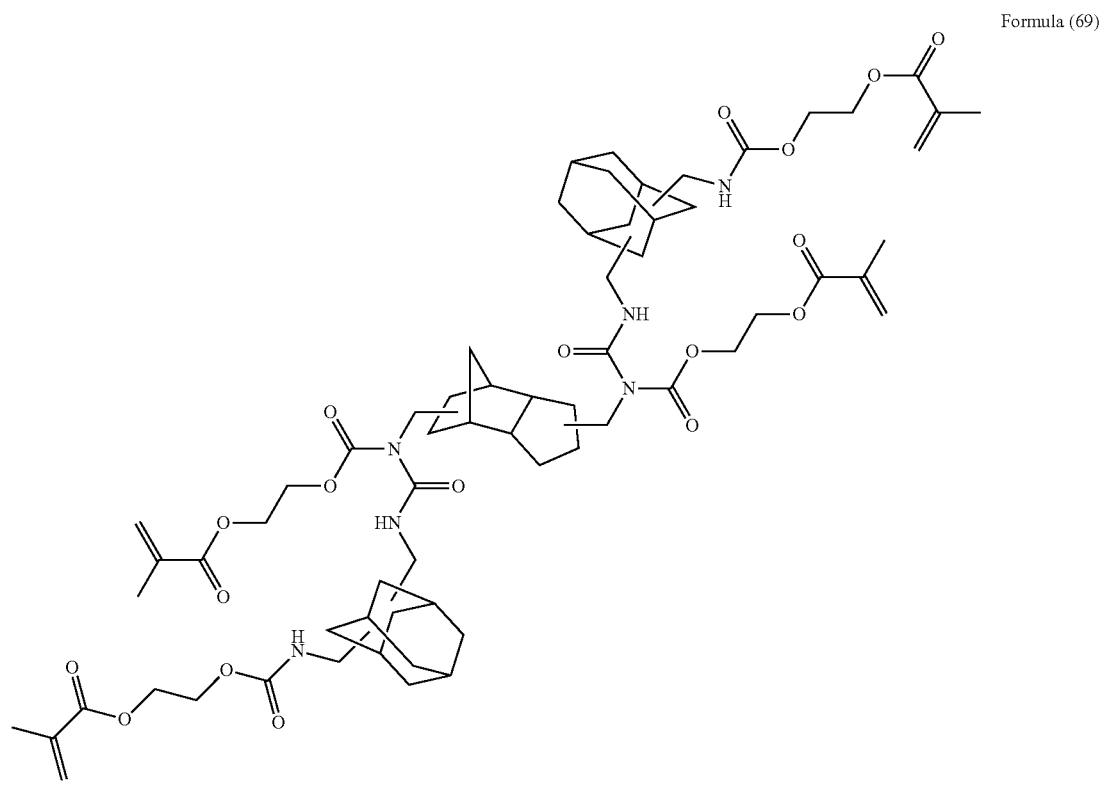

Component (a2): Further Radically Polymerizable Monomers from the Group Consisting of Acrylates and Methacrylates, Preferably from the Group of Methacrylates, The optional constituent, that does not count as a component (a1), of the matrix-forming mixture of monomers is made up of radically polymerizable monomers selected from the group consisting of acrylates and methacrylates.

The radically polymerizable monomers of component (a2) preferably have at least two ethylenic groups.

In a preferred composition according to the invention monomer component (a2) comprises or monomer component (a2) consists of (a2) one or a plurality of polyalkylene glycol di(meth)acrylates, preferably from one or a plurality of polyethylene glycol di(meth)acrylates.

Preference according to the invention is for a composition wherein the monomer component (a2) contains or consists of one or a plurality of polyalkylene glycol di(meth)acrylate(s) with 4 through 10 alkylene oxide units, preferably contains or consists of one or a plurality of polyethylene glycol di(meth) acrylate(s) with 4 through 10 ethylene oxide units.

Preferred polyalkylene glycol di(meth)acrylates correspond to the formula

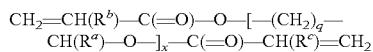

wherein the following applies
$R^a$ is hydrogen or C1-C4-alkyl,
$R^b$ and $R^c$ are hydrogen or methyl, respectively and independently of one another,
the index q is an integer selected from the group of integers from 1 through 5, preferably 1, 3 or 4,
and
the index x is an integer selected from the group of integers from 2 through 18, preferably 3 through 12.

Preferably index q=1.

Further preferred polyalkylene glycol di(meth)acrylates therefore correspond to the formula

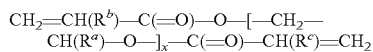

wherein
$R^a$, $R^b$ and $R^c$ as well as x in each case have the meanings given above.

Preferably the index x is an integer selected from the group of integers from 4 through 10.

$R^a$ is preferably hydrogen or methyl.

Particular preference as monomers of component (a2) is for polyethylene glycol di(meth)acrylates with 4 through 10 ethylene oxide units (i.e. monomers of the formula given above, in which $R^a$ is hydrogen and x=4 through 10).

Quite particular preference as monomers of component (a2) is for polyethylene glycol di(meth)acrylates with 4 through 10 ethylene oxide units (i.e. monomers of the formula given above, in which $R^a$, $R^b$ and $R^c$ are in each case hydrogen and x=4 through 10).

In the patent literature a large number of diacrylate and dimethacrylate monomers are mentioned (for example also in DE 3941629 A1, which by way of reference is a constituent of this application, in particular the disclosure between column 6, line 15 to column 8, line 10), which are suitable for use in a composition according to the invention.

Compositions according to the invention can also contain as component (a2) one or a plurality of dimethacrylate monomers, preferably selected from the group consisting of ethylene glycol dimethacrylate (EGDMA), 1,6-hexandiol dimethacrylate (HEDMA), triethylene glycol dimethacrylate (TEDMA), 1,12-dodecandiol dimethacrylate (DODMA), ethoxylated bisphenol A dimethacrylate, polyethylene glycol dimethacrylate (PEGDMA), 7,7,9-trimethyl-4,13-dioxo-5,12-diazahexadecan-1,16-dioxydimethacrylate (UDMA), butane diol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, and glycerin dimethacrylate.

Bisphenol-A-glycidyl-methacrylate (Bis-GMA) can indeed be used. Preferably, however, a composition according to the invention does not contain the compound Bis-GMA. Preferably a composition according to the invention is free from all compounds with a bisphenol-A structure element.

The racially polymerizable monomers of component (a2) which are thus not part of component (a1)) can also be hydroxyl compounds. Here all hydroxyl compounds of acrylates and methacrylates normally used in dental chemistry can be used. Preference is for hydroxyl compounds of methacrylates, and here in turn preference is for 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol dimethacrylate, glycerin dimethacrylate, and 2,2-bis[4-[3-methacryloyloxy-2-hydroxypropoxy]phenyl]propane.

As a further constituent photocurable acrylate or methacrylate monomers based on polysiloxanes, as for example described in DE 19903177 or in DE 4416857, which by way of reference are a constituent of this application, can also be used.

Constituent (b): Initiators and/or Catalysts

A composition according to the invention is preferably photocurable and/or chemically curable. Preference is for a composition according to the invention, wherein constituent (b) comprises or consists of one or a plurality of photocuring initiators and/or one or a plurality of initiators for chemical curing.

The total quantity of constituent (b) is preferably in the range 0.1 through 3 wt. %, preferably in the range 0.2 through 1.5 wt. %, in each case with reference to the total weight of the composition according to the invention.

Preferred compositions according to the invention are chemically curable and comprise one or a plurality of initiators for chemical curing.

Preferred compositions according to the invention are photocurable and comprise one or a plurality of photocuring initiators.

Preferred compositions according to the invention are dual-curing.

Dual-curing compositions according to the invention comprise one or a plurality of photoinitiators (component (b-1)) and one or a plurality of initiators for chemical curing (component (b-2)).

Particularly preferred compositions according to the invention are those wherein component (b) comprises one or a plurality of radical-forming initiators and/or catalysts, preferably selected from the group consisting of photoinitiators, hydroperoxides and thiourea derivatives, here preferably at least one photoinitiator, one hydroperoxide and one thiourea derivative, since with such compositions particularly good results in the context of the present invention can be achieved.

Component (b-1)—Photoinitiators

Examples of a photoinitiator include catalysts which have solely a photo-sensitizing effect and combinations of sensitizers and accelerators.

Examples of photosensitizers are alpha-diketones, benzoin alkyl ethers, thioxanthones, benzophenones, acylphosphinoxides, acetophenones, ketals, titanocenes, sensitizing colorants, etc. The sensitizers can be used alone or in combination. Specific substance examples of the various classes can be found, for example, in DE 10 2006 019 092 A1 or in DE 39 41 629 C2, which by way of reference are a component part of this application.

Examples of accelerators, which are used together with the sensitizers, are tertiary amines, secondary amines, barbituric acids, tin compounds, aldehydes and sulfur compounds. Specific substance examples of the various classes can be found in DE 10 2006 019 092 A1 or in DE 39 41 629 C2, which by way of reference are a constituent of this application.

Further suitable initiators and initiator combinations are described in DE 601 16 142, which by way of reference are a constituent of this application.

The photoinitiators used in connection with the present invention wherein through the absorption of light in the wavelength range 300 nm through 700 nm, preferably 350 nm through 600 nm and particularly preferably 380 nm through 500 nm, optionally in combination with one or a plurality of co-initiators, they can bring about the curing of a mixture that is curable according to the invention.

The absorption maximum of campherquinone (CQ) is approximately 470 nm and thus in the range of blue light. Campherquinone (CQ) is one of the $PI_2$-initiators and is regularly used together with a co-initiator.

Preferably a composition according to the invention contains campherquinone (CQ).

Similarly preferred is a combination of an alpha-diketone and an aromatic tertiary amine, greater preference here being for the combination of campherquinone (CQ) and ethyl-p-N,N-dimethylaminobenzoate (DABE).

Likewise preferred is the further combination of the "alpha-diketone/aromatic tertiary amine" system with a phosphine oxide, in particular with phenyl-bis(2,4,6-trimethylbenzoyl)phosphine oxide and/or 2,4,6-trimethylbenzoyl-diphenyl phosphine oxide. Regarding the structures of suitable phosphine oxides for use in a mixture that can be cured according to the invention reference is made to printed publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which by way of reference are a constituent of this application.

The phosphine oxides indicated in these printed publications are particularly suitable on their own or in combination with the "alpha-diketone/amine" system as a photopolymerization initiator system in the mixtures according to the invention.

Alternatively borate salts, as described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, can be used as photoinitiators, which by way of reference are a constituent of this application.

Further suitable photoinitiators are described in J.-P. Fouassier, Photoinitiation, Photopolymerization and Photocuring, Hanser Publishers, Munich, Vienna, New York 1995 and in J. F. Rabek (publisher), Radiation Curing in Polymer Science and Technology, Vol. II, Elsevier Applied Science, London, New York 1993, which by way of reference are a constituent of this application.

Component (b-2)—Initiators for the Chemical Curing

Various initiators for a chemical curing will be known to a person skilled in the art. In this connection reference is made by way of example to EP 1 720 506.

Preferred initiators for chemical curing are benzoyl peroxide, lauroyl peroxide in particular dibenzoyl peroxide in combination with amines such as N,N-dimethyl-p-toluidine, N,N-dihydroxyethyl-p-toluidine and structurally related amines.

Here the peroxides and the amines are spread across two different components of the dental material. During the mixing of the amine-containing components (so-called base paste) with the peroxide-containing components (so-called initiator or catalyst paste) through the reaction of amine and peroxide (redox reaction) the radical reaction is initiated.

Particularly preferred initiators are hydroperoxides, herein particular cumolhydroperoxide, preferably in combination with thiourea derivatives, in particular allyl thiourea.

Here the hydroperoxides and the thiourea derivatives are divided up into two different components of a composition according to the invention. When mixing the thiourea derivative-containing component with the hydroperoxide-containing component the radical reaction is initiated by redox reaction.

In compositions according to the invention the cumolhydroperoxide/allyl thiourea redox system has proven to be particularly advantageous. This redox system, together with the monomers according to the invention or to be used according to the invention of component (a1), preferably together with the monomer component (a2), resulted in particularly suitable compositions in accordance with the invention which extensively demonstrate the desired characteristics for a root canal filling and/or sealing material.

Dual-curing systems comprise a combination of photoinitiator(s) and initiator(s) for chemical curing.

In a quite particularly preferred configuration a composition according to the invention comprises campherquinone (CQ), ethyl-p-N,N-dimethylaminobenzoate (DABE), cumolhydroperoxide and allyl thiourea.

By way of example, the base paste can also contain a photoinitiator, so that the base paste can be used either on its own as a photo-curing agent or together with the initiator paste as a photo- and self-curing dental material.

Apart from the organic peroxide compounds with an oxidative effect, barbituric acids or barbituric acid derivatives and malonyl sulfamides can also be used as redox systems.

Of the barbituric acid systems the so-called Bredereck systems are of great significance. Examples of suitable Bredereck systems and references to the corresponding patent literature can be found in EP 1 839 640 and in DE 14 95 520, WO 02/092021 or in WO 02/092023, which by way of reference are a constituent of this application.

Suitable malonyl sulfamides are described in EP 0 059 451 which by way of reference is a constituent of this application. Preferred compounds here are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2.6,6-diocytyl-4-isobutylmalonyl sulfamide.

Sulfur compounds in the oxidation stage +2 or +4 such as sodium benzene sulfinate or sodium paratoluene sulfinate can also be used.

In order to accelerate the curing the polymerization can be carried out in the presence of compounds of heavy metals such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethyl hexanoate, copper di(methacrylate) and copper napththenate.

Constituent (c): Filler Component

A composition according to the invention can preferably contain an amount of the filler component (c) of up to 85 wt. %, in relation to the total weight of the composition according to the invention, wherein the filler component can comprise one, two or a plurality of fillers.

The total amount of the filler of component (c) is preferably in the range 35 through 85 wt. %, preferably in the range 50 through 80 wt. %, particularly preferably in the range 60 through 75 wt. %, in each case in relation to the total weight of the composition.

The average particle size $d_{50}$ of the filler particles to be used according to the invention of a composition according to the invention is determined by means of light scattering (laser diffraction), preferably with a Beckman Coulter LS13320 particle size analyzer.

In connection with the present invention, nanoparticles mean particles with an average particle size of less than 200 nm.

A preferred composition according to the invention contains in addition to the component (c1) of the radiopaque filler a component (c2) of the non-radiopaque filler, wherein preferably component (c2) consists of or comprises:

(c2-a) non-radiopaque, non-agglomerated nanoscale fillers with a particle size of less than 200 nm,
and/or
(c2-b) non-radiopaque, agglomerated filler particles, which preferably are organically surface-modified, preferably silanized.

The filler component (c) comprises in a preferred configuration one or a plurality of radiopaque fillers of component (c1), preferably with an average particle size in the range 0.4 µm through 10 µm, and one or a plurality of fillers of component (c2-b).

The filler component (c) comprises in a preferred configuration one or a plurality of radiopaque fillers of component (c1), one or a plurality of fillers of component (c2-b) and one or a plurality of fillers of component (c2-a).

Component (c1): Radiopaque Fillers

As already mentioned above the radiopacity is normally measured in aluminum equivalents and indicated in "mm (Al)".

Here these radiopacity details relate not to the pure radiopaque filler, but to a composite material that contains 75.00 wt. % of the radiopaque filler.

Radiopaque fillers in the context of the present text have a radiopacity—measured in a polymer matrix which has an amount of 75.00 wt. % radiopaque filler—of at least 3 mm aluminum equivalents according to ISO 4049, i.e. at least 3 mm (Al).

Preferably radiopaque fillers have a radiopacity of at least 3.5 mm (Al), preferably of 4 mm (Al), more preferably of at least 5 mm (Al) and particularly preferably of at least 6 mm (Al).

In order to determine the radiopacity of a filler according to ISO 4049, the filler under investigation, together with a quantity of one or a plurality of initiators necessary for the subsequent curing, is incorporated into a monomer matrix. Following curing of the mixture the radiopacity (in aluminum equivalents) of the resultant material, which contains an amount of 75.00 wt. % of the filler under investigation, is determined according to ISO 4049. The monomer or polymer matrix itself make no contribution to the radiopacity.

The radiopacity values indicated here and determined according to ISO 4049 relate in particular to a cured composite material, prepared by photocuring of the following composition:

24.775 g bis(methacryloyloxymethyl)tricyclo[5.2.1.0$^{2,6}$]decane, 0.090 g CC, 0.135 g DABE and 75.00 g of filler under investigation.

The filler component (c) of a composition according to the investigation contains one, two or a plurality of radiopaque fillers as component (c1). The radiopaque filler(s) is/are preferably selected from the group consisting of zinc, ytterbium, yttrium, zirconium, strontium, calcium, titanium, tungsten, tantalum, niobium, barium, bismuth, molybdenum, lanthanum, cerium in the form of powders, alloys, oxides, halogenides, oxohalogenides, sulfates, phosphates, silicates, carbonates, tungstates or glasses and mixtures of these.

Preferred radiopaque fillers are selected from the group consisting of zinc, ytterbium, yttrium, zirconium, strontium, calcium, titanium, tungsten, tantalum, niobium, barium, bismuth, molybdenum in the form of alloys, oxides, fluorides, oxohalogenides, sulfates, phosphates, silicates, carbonates, tungstates or glasses and mixtures of these.

Advantageous radiopaque fillers here are $CaWO_4$, $ZrO_2$, ytterbium fluoride, barium sulfate and/or radiopaque glasses.

The total quantity of the radiopaque fillers of component (c1) is preferably in the range 30 through 75 wt. %, preferably in the range 40 through 70 wt. %, more preferably in the range 50 through 70 wt. %, particularly preferably in the range 55 through 65 wt. %, in each case in relation to the total weight of the composition.

The radiopaque fillers of component (c1) are preferably used in the form of microparticles with an average particle size in the range 0.4 µm through 10 µm.

The radiopaque fillers of component (c1) preferably have an average particle size of 2 µm through 8 µm, preferably an average particle size of 3 µm through 7 µm.

The fillers can have a monomodal or polymodal, for example a bimodal, particle size distribution. Microparticles with a bimodal or multimodal particle size distribution are preferred according to the invention, since with these a more complete volumetric filling can be achieved than with the general use of microparticles with monomodal particle size distribution. In the case of a bi- or multimodal particle size distribution the particles from the fractions with the larger particle sizes bring about a coarse filling of the volume, while the particles from the fraction with the smaller particle sizes where possible fill the cavities between the particles from the fractions with the larger particle sizes.

A composition according to the invention can contain microparticles of various fractions, wherein the average particle sizes of the fractions differ, wherein the average particle sizes of these deviate by at least 0.5 µm, preferably by at least 0.7 µm, from one another.

The microparticles of various fractions can consist of the same or different materials; here a plurality of fractions of microparticles can be present, the average particle sizes of which are approximately the same or are within a certain range, wherein the particle materials differ between the fractions.

For better bonding in the polymer matrix of a composition according to the invention the microparticles can be organically surface-modified. One example of surface treatment of the fillers is the use of a silane, leading to silanized microparticles. Methacryloxypropyltrimethoxysilane is particularly well-suited for surface treatment (as a bonding agent).

In an especially preferred composition according to the invention at least part of the microparticles of the radiopaque fillers is made up of organically surface-modified particles, preferably silanized particles and/or at least part of the microparticles of the radiopaque fillers is made up of dental glass particles; preferably at least part of the microparticles of the radiopaque fillers is organically surface-modified dental glass particles, preferably silanized dental glass particles.

The radiopaque fillers of component (c1) can also be used in the form of radiopaque agglomerates and/or radiopaque non-agglomerated nanoparticles.

Preferably the average particle size of the radiopaque nanoparticles is less than 100 nm and particularly preferably less than 60 nm.

In a preferred configuration the radiopaque nanoparticles are present in non-agglomerated form, for example dispersed in a medium, preferably in monodisperse form.

In one configuration the composition according to the invention can contain one or a plurality of radiopaque fillers of component (c1), wherein part of the radiopaque fillers is used in the form of microparticles (preferably with an average particle size in the abovementioned range) and part of the radiopaque fillers in the form of nanoparticles, preferably in the form of non-agglomerated radiopaque nanoparticles.

The materials for the radiopaque nanoparticles to be used according to the invention are preferably oxides or mixed oxides and preferably selected from the group consisting of oxides and mixed oxides of the elements yttrium, strontium, barium, zirconium, niobium, tantalum, tungsten, bismuth, molybdenum, zinc, ytterbium, lanthanum, cerium, and mixtures thereof. Here, as explained, the preferred oxidic nanoparticles are not agglomerated.

In order to achieve a good bonding of the radiopaque nanoparticles in the polymer matrix of a composition according to the invention, the surfaces of the radiopaque nanoparticles (preferably the preferred radiopaque nanoparticles) are organically modified, i.e. their surfaces have organic structure elements. One example of surface treatment of the fillers is the use of a silane. Methacryloxypropyltrimethoxysilane is particularly well-suited as a bonding agent.

Component (c2): Non-Radiopaque Fillers
Component (c2-a): Non-Radiopaque, Non-Agglomerated Nanoparticles Filler component (c) can preferably comprise a filler (c2-a) in the form of non-radiopaque, non-agglomerated, nanoparticles with an average particle size of less than 200 nm.

Preferably here the average particle size is less than 100 nm and particularly preferably less than 60 nm.

The non-radiopaque, non-agglomerated nanoparticles of component (c2-a) are preferably surface-modified, preferably organically surface-modified, preferably silanized.

If a composition according to the invention, in addition to the radiopaque fillers of component (c1) also contains non-agglomerated nanoparticles as a further filler of component (c2-a), the mechanical characteristics are enhanced—obviously because of better spatial filling by the filler particles overall—while the solubility is significantly reduced.

The filler component (c) of a composition according to the invention can comprise one or a plurality of fillers of component (c2-a) in a quantity in the range 0 through 12 wt. %, preferably in a quantity in the range 0 through 8 wt. %, in each case in relation to the total weight of the composition.

A composition according to the invention comprises preferably component (c2-b) which comprises non-agglomerated silanized silica nanoparticles or consists of these.

A composition according to the invention preferably contains non-agglomerated silanized silica nanoparticles in a quantity in the range 2 through 12 wt. %, more preferably in the range 3 through 10 wt. %, particularly preferably in the range 4 through 8 wt. %, in relation to the total weight of the composition.

Here the silanized silica is preferably used in the form of silanized nanoparticles with an average particle size of less than 100 nm, preferably less than 60 nm.

In a preferred configuration the non-agglomerated nanoscale particles are present for example dispersed in a medium, preferably in monodisperse form.

The materials for the nanoparticles to be used according to the invention are preferably oxides and mixed oxides and preferably selected from the group consisting of oxides and mixed oxides of the elements silicon and/or aluminum. Here, as explained, the preferred oxidic nanoparticles are not agglomerated.

In order to allow the nanoparticles to bond properly in the polymer matrix of a composition according to the invention, the surfaces of the nanoparticles (preferably the preferred oxidic nanoparticles) are organically modified, i.e. their surfaces have organic structure elements. One example of surface treatment of the fillers is the use of a silane. Methacryloxypropyltrimethoxysilane is particularly well-suited as a bonding agent.

Component (c2-b): Non-Radiopaque, Agglomerated Filler Particles

The filler component (c) preferably comprises a filler (c2-a) in the form of non-radiopaque, agglomerated filler particles, preferably in the form of agglomerated nanoparticles.

The non-radiopaque, agglomerated filler particles of component (c2-b) are preferably agglomerated organically surface-modified nanoparticles which are preferably silanized.

The materials for the non-radiopaque nanoparticles of component (c2-b) to be used according to the invention are preferably oxides and mixed oxides and preferably selected from the group consisting of oxides and mixed oxides of the elements silicon and/or aluminum. Here, as explained, the preferred oxidic nanoparticles are agglomerated.

Compositions according to the invention with a filler component (c) comprising a mixture containing component (c1) and one or a plurality of fillers of component (c2-b) demonstrated an improved rheology for use as root canal filling or sealing material.

The filler component (c) of a composition according to the invention can comprise one or a plurality of fillers of component (c2-b) in a quantity in the range 0 through 12 wt. %, preferably in a quantity in the range 0 through 8 wt. %, in each case in relation to the total weight of the composition.

A composition according to the invention comprises preferably agglomerated, silanized silica nanoparticles of component (c2-b), preferably in a quantity in the range 1 through 8 wt. %, more preferably in the range 2 through 6 wt. %, in each case in relation to the total weight of the composition.

Further Optional Fillers of Constituent (c2)

The filler component (c2) of a composition according to the invention can also contain further non-radiopaque fillers, which are not a constituent of the components (c2-a) or (c2-b).

Preferably, these further non-radiopaque fillers are only contained in a composition according to the invention in very small quantities, if at all, preferably in a quantity of 0 through 3 wt. %, preferably in a quantity of 0 through 2 wt. %, more preferably in a quantity of 0 through 1 wt. %, in each case in relation to the total weight of the composition.

Additionally, filler materials with, for example, a strengthening effect such as glass fibers, polyamide or carbon fibers can be used. A composition according to the invention can also contain fine particle splinters or bead polymers, wherein the bead polymers can be homo- or copolymers of organically curable monomers.

Constituent (d): Molecular Weight Regulators

A composition according to the invention can contain one or a plurality of molecular weight regulators.

U.S. Pat. No. 4,490,497 A discloses compositions for surgical cement which can be used in the production of dental prostheses. A liquid component of the composition comprises as a chain stopping agent, for example a double unsaturated monocyclic terpene or a single unsaturated bicyclic terpene. It does not disclose compositions that are suitable for filling and/or sealing a root canal.

If a composition according to the invention also comprises a molecular weight regulator, the polymerization process can be influenced and the chain length, degree of cross-linking of the resultant polymer and the kinetics of the polymerization process can be altered in such a way that the desired characteristics are further improved. Here the mechanical properties are significantly reduced and at the same time the water absorption and the flow are surprisingly improved.

The total quantity of the molecular weight regulator(s) of component (d) of a composition according to the invention is preferably in the range 0.01 through 1 wt. %, preferably in the range 0.025 through 0.75 wt. %, more preferably in the range 0.03 through 0.50 wt. %, in each case in relation to the total weight of the composition.

Suitable molecular weight regulators are for example various terpenes, in particular terpinenes (α-terpinene, β-terpinene, γ-terpinene), phellandrenes (α-phellandrene, β-phellandrene) and terpinols (also known as δ-terpinene), 1,4-cyclohexadiene (optionally substituted), 1,3-cyclohexadiene (optionally substituted), 1,4-dihydronaphthalene, 1,4,5,8-tetrahydronaphthalene, 2,5-dihydrofuran or dimeric systyrene as well as linoleic acid and α-linolenic acid.

Molecular weight regulators preferred according to the invention are compounds with two or a plurality of double bonds, preferably compounds with two or a plurality of double bonds that through abstraction of an allyl H-atom can form a delocalized electron system, extending across 5 or a plurality of C-atoms, preferably dienes that through abstraction of an allyl H-atom can form a delocalized electron system, extending across 5 C-atoms.

Molecular weight regulators preferred according to the invention as a constituent of a root canal sealing and/or filling material are molecular weight regulators selected from the group of monoterpenes, preferably from the group of monoterpene dienes, preferably from the group consisting of α-terpinene, β-terpinene, γ-terpinene, α-phellandrene, β-phellandrene and terpinols or selected from the group consisting of linoleic acid, linolenic acid and other substituted or non-substituted cyclohexadienes.

Molecular weight regulators particularly preferred according to the invention are γ-terpines and α-terpines.

Of course, mixtures of molecular weight regulators can also be used.

Constituent (e): Active Substances

A composition according to the invention can contain one or a plurality of active substances selected from the group consisting of remineralizing, therapeutic, devitalizing, disinfecting, inflammation-inhibiting, antibacterial and cariostatic active substances, The compositions according to the invention can contain therapeutically active and/or disinfecting active substances such as benzalkonium chloride, chlorhexidine, nanosilver, nanocopper and/or devitalizing and/or antibacterial and/or inflammation-inhibiting and/or cariostatic additives.

The compositions according to the invention can further contain bioactive and/or remineralizing additives such as calcium carbonate, calcium hydroxide, calcium oxide, tricalcium fosfate, tetracalcium fosfate, calcium hydroxylapitate, calcium/strontium apatite or fluoroapatite. Here zinc oxide and ion-emitting fillers such as glass ionomer cement glass together with bioactive and/or remineralizing additives can also be used.

Constituent (f): Adhesion-Promoting Additives

A composition according to the invention can contain one or a plurality of additives to improve adhesion (so-called adhesive monomers), in particular to improve adhesion to the dentin.

Although the compositions according to the invention must be easy to remove from the root canal, they need to include a small quantity of an adhesion-promoting additive (so-called adhesive monomers), which further improves the adhesion of a composition according to the invention with a tight seal to the dentin.

In order to improve the adhesion, a composition according to the invention can contain as constituent (f) one or a plurality of acid group—containing acrylate and/or methacrylate monomers. Such acid group-containing monomers can preferably have a carboxylic acid, a polycarboxylic acid, a phosphoric acid, a phosphonic acid, a polyphosphonic acid, a sulfonic acid and/or a thiophosphoric acid function. The monomer can contain one or a large number of acid functions in a molecule.

A preferred composition according to the invention comprises one or a plurality of adhesion-promoting additives, selected from the group consisting of polymerizable or non-polymerizable acids, acid anhydrides and esters, preferably from the group consisting of phosphoric acids, phosphonic acids, carboxylic acids and their salts, carboxylic acid esters and carboxylic acid anhydrides, preferably in a quantity in the range 0.1 through 5 wt. %, more preferably in a quantity in the range 0.5 through 2.5 wt. %, in each case in relation to the total weight of the composition.

Preferably the one or a plurality of adhesion-promoting additives of constituent (f) is/are selected from the group consisting of 10-(meth)acryloyloxydecyl dihydrogen phosphate (10-MDP), 2-(meth)acryloyloxyethyl dihydrogen phosphate, 6-(meth)acryloyloxyhexyl dihydrogen phosphate, 4-(meth)acryloyloxybutyl dihydrogen phosphate, 8-(meth)acryloyloxyoctyl dihydrogen phosphate, 2-(meth)acryloyloxynonyl dihydrogen phosphate, 11-(meth)acryloyloxyun-decyl dihydrogen phosphate, 20-(meth)acryloyloxyeicosyl dihydrogen phosphate, 1,3-di(meth)acyloyloxypropyl-2-dihydrogen phosphate, 2-(meth)acryloyloxyethylphenyl dihydrogen phosphate, di(2-(meth)acryloyloxyethyl)pyrophosphate, di(2-(meth)acyloyloxypropyl)pyrophosphate, di(2-(meth)acyloyloxybutyl)pyrophosphate, di(2-(meth)acyloyloxypentyl)pyrophosphate, the di(2-(meth)acyloyloxyhexyl)pyrophosphate, di(2-(meth)acyloyloxydecyl)pyrophosphate, bis[5-(2-(meth)acryloyloxyethoxycarbonyl)-heptyl]hydrogen phosphate, mono-, di- and/or triesters of phosphoric acid, obtained by reaction of hydroxy-C2-C8-alkyl methacrylate (here preferably hydroxyethyl methacrylate and/or hydroxypropyl methacrylate) or glyceryl dimethacrylate with phosphoroxy chloride, glyceryl dimethacrylate phosphate, pentaerythritol trimethacrylate phosphate, dipentaerythritol pentaacrylate phosphate, tetramethacryloxyethyl pyrophosphate, 4-(methacryloyl-oxyethyl) trimellitic acid, trimellitic acid-4-methacryloyloxy ethyl ester (4-MET), trimellitic acid anhydride-4-methacryloyloxy ethyl ester (4-META), pyromellitic acid dimethacrylate, pyromellitic acid glycerol dimethacrylate, methacryloyloxy ethyl phthalate, methacryloyloxy ethyl maleate, methacryloyloxy ethyl succinate, 1,3-glycerol dimethacrylate maleate and di-oxyethoxy methacrylic acid ethylene diamine tetraacetic acid ester.

The monomers mentioned can be used individually or in mixtures.

Other suitable acid group-containing monomers are mentioned in, for example, EP 0980682 A1 (in particular paragraphs [0059]-[0065]) or EP 0948955 A1 (in particular paragraphs [0031]-[0034]), which by way of reference are a constituent of this application.

Preferred adhesion-promoting additives of component (f) are 10-(meth)acryloyloxydecyl dihydrogen phosphate (10-MDP), glyceryl dimethacrylate phosphate, pentaerythritol trimethacrylate phosphate, dipentaerythritol pentaacrylate phosphate, tetramethacryloxy ethyl pyrophosphate, trimellitic acid-4-methacryloyloxy ethyl ester (4-MET), trimellitic acid anhydride-4-methacryloyloxy ethyl ester (4-META), pyromellitic acid dimethacrylate, pyromellitic acid glycerol dimethacrylate.

Similarly preferred are further phosphoric acid esters, in particular the phosphoric acid esters of hydroxyethyl(meth)acrylate (here preferably mono- or diesters), hydroxypropyl(meth)acrylate (here preferably mono- or diesters) and bisphenol-A-glycidyl-(meth)acrylate.

An especially effective adhesion-promoting additive in the context of the invention is the condensation product of bis(hydroxymethyl)tricyclo[$5.2.1.0.^{2,6}$]decane and maleic acid, in which the two tricycles are linked via ester bonds. Of the two hydroxyl groups that now result, one can then be esterified with adipinic acid. The compound provides a composition according to the invention with a high force of adhesion to dentin. This compound is known by the name "Adhesion Resin BL 215 C". A preferred composition according to the invention contains this adhesion-promoting additive.

Instead of maleic acid, other $\alpha,\beta$-unsaturated dicarboxylic acids such as citraconic, fumaric, itaconic or mesaconic acid can be used.

Preferred compositions according to the invention comprise one or a plurality of adhesion-promoting additives of component (f) selected from the group consisting of
  10-(meth)acryloyloxydecyl dihydrogen phosphate (10-MDP), glyceryl dimethacrylate phosphate, pentaerythritol trimethacrylate phosphate, dipentaerythritol pentaacrylate phosphate, tetramethacryloxy ethyl pyrophosphate, trimellitic acid-4-methacryloyloxy ethyl ester (4-MET), trimellitic acid anhydride-4-methacryloyloxy ethyl ester (4-META), pyromellitic acid dimethacrylate, pyromellitic acid glycerol dimethacrylate,
  further phosphoric acid esters, here preferably the phosphoric acid esters of hydroxyethyl(meth)acrylate (here preferably mono- or diesters), hydroxypropyl(meth)acrylate (here preferably mono- or diesters) and bisphenol-A-glycidyl-(meth)acrylate,
  polymerizable carboxylic acids, which are based on an unsaturated polyester resin preparable by the following steps:
    (i) esterification of dihydroxymethyltricyclo[$5.2.1.0.^{2,6}$]decane with an unsaturated $\alpha,\beta$-unsaturated dicarboxylic acid in a molar ratio of 2:1, and
    (ii) reaction of the hydroxyl groups of the polyester formed in step (i) with a saturated dicarboxylic acid, here preferably adipinic acid.

Optional Further Additives

A composition according to the invention in many cases comprises one or a plurality of further additives.

These additives can have various functions. Normal additives for use in dental compositions are known to a person skilled in the art who will select the appropriate additive(s) according to the desired function. In the following examples of typical additives and their functions are provided.

Photocurable dental compositions, as preferred according to the invention, preferably contain one or a plurality of inhibitors, also referred to as stabilizers. These are normally added in order to prevent spontaneous polymerization. They react with prematurely forming radicals, which are intercepted, prevent premature polymerization and increase the storage stability of the dental composition. Common inhibitors are phenol derivates such as hydroquinone monomethylether (HQME) or 2,6-di-tert.butyl-4-methylphenol (BHT). Further inhibitors such as tert.-butylhydroxy anisol (BHA), 2,2 diphenyl-1-picrylhydrazyl, galvinoxyl, triphenylmethyl radicals, 2,3,6,6,-tetramethylpiperidinyl-1-oxyl radicals (TEMPO) and derivatives of TEMPO or phenothiazine and derivatives of this compound are described in EP 0783880 B1 which by way of reference are a constituent of this application. Alternative inhibitors are indicated in DE 10119831 A1 or in EP 1563821 A1, which by way of reference are a constituent of this application.

A dental composition preferred according to the invention thus comprises as an additive one or a plurality of polymerization inhibitors to increase the storage stability of the composition, preferably selected from the group consisting of hydroquinone monomethylether (HQME), phenols, here preferably 2,6-di-tert.butyl-4-methyl phenol (BHT) and tert.-butylhydroxy anisol (BHA), 2,2-diphenyl-1-picrylhydrazyl radicals, galvinoxyl radicals, triphenylmethyl radicals, 2,3,6,6,-tetramethylpiperidinyl-1-oxyl radicals (TEMPO) and derivatives thereof and phenothiazine and derivatives thereof.

A dental composition preferred according to the invention comprises as an additive one or a plurality of fluoride releasing substances, here preferably sodium fluoride and/or aminofluoride.

Additionally, one or a plurality of surfactants can be a constituent of a composition according to the invention.

UV absorbers, which for example as a result of their conjugated double bonding systems and aromatic rings are capable of absorbing UV radiation, are in many cases a constituent of a composition according to the invention. Examples of UV absorbers are 2-hydroxy-4-methoxybenzophenone, salicylic acid phenyl ester, 3-(2'-hydroxy-5'-methylphenyl)-benzotriazole, or diethyl-2,5-dihydroxy-terephthalate.

Further optional additives are aromatic substances.

The invention also relates to a process for preparation of a composition according to the invention, preferably in one of the configurations identified as preferred or particularly preferred, with the following steps:
  mixing of constituents (a), (b) and (c), optionally (d), (e) and/or (f) and optionally further additives.
or
  preparing a multi-component, preferably two-component, system comprising all constituents (a), (b), (c), optionally (d), (e) and (f), and optionally further additives,
  wherein the initiators and/or catalysts of the constituent (b) are distributed over separate components of the dental composition so that a chemical initiation is triggered through the mixing of said components.

A multi-component, for example a two-component, system will be understood by a person skilled in the art to be a composition with a plurality of, for example two, spatially separate components. One of the (for example two) components here contains one or a plurality of monomers, while an- (or the) other component contains one or a plurality of curing agent(s). In most cases the various (or both) components must be intensively mixed together prior to application.

The present invention also relates to a product, obtainable by curing of a composition according to the invention, particularly in one of the configurations identified as particularly preferred.

The present invention further relates to a composition according to the invention, in particular in one of the configurations identified as preferred or particularly preferred, as a dental filling and/or sealing material or for use as a dental filling and/or sealing material, in particular as a dental filling and/or sealing material for a root canal.

The compositions according to the invention can be used as permanent or as temporary root canal sealing and/or filling materials.

Therefore the present invention also relates to the use of a composition according to the invention, in particular in one of the configurations identified as preferred or particularly preferred, for the temporary or permanent filling and/or sealing of a root canal.

The present invention also relates to a composition according to the invention, in particular in one of the configurations identified as preferred or particularly preferred, for use in a therapeutic method as a dental filling and/or sealing material for a root canal, in particular for use in a therapeutic method for temporary or permanent filling and/or sealing of a root canal.

The present invention also relates to a method for treating a dental condition, characterized in that a composition according to the invention, preferably in one of the configurations indicated as preferred, is used as a dental filling and/or sealing material for a root canal, in particular for use in a therapeutic method for temporary or permanent filling and/or sealing of a root canal. The method can include providing the composition as described herein and applying the composition to tissue of a patient as part of a medical procedure, e.g., a dental procedure, such as a root canal. The method can include applying the composition as a dental filling and/or sealing material for a root canal, in particular as a temporary or permanent filling and/or sealing of a root canal. The method can further include curing the composition. As used herein, "tissue" is intended to have its conventional meaning and include all features of teeth.

Compositions according to the invention, in particular as root canal filling and sealing materials, can for example be applied in application capsules. Then the components are mixed in a capsule mixing device and introduced directly into the root canal via an applicator device.

The compositions according to the invention can also be applied with the help of double syringe or double-chamber cartridges with a suitable mixing tip.

In a preferred configuration the present invention relates to in a further aspect therefore a multi-component syringe, preferably a 2-component application syringe, containing a composition according to the invention, preferably in one of the configurations identified as preferred.

A typical example of a multi-component syringe, which can be used as a root canal syringe and which in the context of the present invention is preferably used, is a 2-component application syringe in the form of a double-chamber syringe with a mixing tip, wherein the mixing tip preferably has 6 through 16 mixing spirals. Preferably a root canal syringe to be used in the context of the present invention, here preferably a 2-component application syringe, comprises an application attachment adapted or which can be adapted to the tooth root geometry, with an external diameter of 0.3 through 0.9 mm and a length of 15 through 50 mm.

The compositions according to the invention are preferably marketed in kits for sealing and filling of a root canal. A typical kit then contains for example a multi-component syringe, preferably a 2-component application syringe, and optionally application attachments, paper tips, root canal filling pencils, which optionally are surface-coated, as well as one or a plurality of paste carriers.

In a further aspect the present invention therefore relates a kit for sealing and/or filling root canals, containing
   a composition according to the invention, preferably in one of the configurations identified as preferred, in multi-component form, preferably in two-component form, preferably in the form of a multi-component syringe, preferably a 2-component application syringe,
and
   optionally one, two or a plurality of or all the components of application attachments, paper tips, root canal filling pencils and paste carriers.

Examples

The invention is further explained using the following examples. Unless otherwise indicated all data relate to the weight.

The following designations or abbreviations are used here:
CQ=campherquinone
DABE=ethyl-p-N,N-dimethylaminobenzoate
PEG400DMA=polyethylene glycol-400-dimethacrylate
TCD monomer=bis(methacryloyloxymethyl)tricyclo[$5.2.1.0^{2,6}$]decane
Nano-SiO$_2$=silanized SiO$_2$ particles (40 nm)
Cumolhydroperoxide (88%)=a mixture of 88% cumolhydroperoxide and 12% cumol
GK=highly radiopaque, Zr-containing glass ($d_{50}$=5 μm; BET surface: 0.5 m$^2$/g)
Silanized silica=organically surface-modified agglomerated silica particles (BET-surface): 160 m$^2$/g t 25 m$^2$/g)
Adhesive monomers=Adhesion Resin BL 215 C The two respective pastes had good flow and were easily miscible with one another.

The compositions of the two respective pastes (in parts by weight) are listed in the following two tables).

Example 1 is a comparative example. Examples 2-10 are examples according to the invention.

TABLE 1

Paste A

| | Example 1 | Example 2 | Example 3 | Example 4 | Example 5 | Example 6 | Example 7 | Example 8 | Example 9 | Example 10 |
|---|---|---|---|---|---|---|---|---|---|---|
| Nano-SiO$_2$ | 0.00 | 0.00 | 0.00 | 0.00 | 6.15 | 6.16 | 0.00 | 6.16 | 0.00 | 0.00 |
| TCD monomer | 0.00 | 30.34 | 15.17 | 15.14 | 12.32 | 12.30 | 15.17 | 0.00 | 15.17 | 15.17 |
| Compound of Formula (2) | 0.00 | 0.00 | 0.00 | 0.00 | 0.00 | 0.00 | 0.00 | 12.30 | 0.00 | 0.00 |
| PEG400DMA | 30.34 | 0.00 | 15.17 | 15.14 | 12.32 | 12.30 | 14.17 | 12.30 | 0.00 | 0.00 |

TABLE 1-continued

Paste A

| | Example 1 | Example 2 | Example 3 | Example 4 | Example 5 | Example 6 | Example 7 | Example 8 | Example 9 | Example 10 |
|---|---|---|---|---|---|---|---|---|---|---|
| Triethylene glycol-DMA | 0.00 | 0.00 | 0.00 | 0.00 | 0.00 | 0.00 | 0.00 | 0.00 | 15.17 | 0.00 |
| Tetraethylene glycol-DMA | 0.00 | 0.00 | 0.00 | 0.00 | 0.00 | 0.00 | 0.00 | 0.00 | 0.00 | 15.17 |
| GK | 63.70 | 63.70 | 63.70 | 63.60 | 64.70 | 64.57 | 63.70 | 64.57 | 63.70 | 63.70 |
| Silanized silica | 5.56 | 5.56 | 5.56 | 5.56 | 4.11 | 4.11 | 5.56 | 4.11 | 5.56 | 5.56 |
| Allyl thiourea | 0.28 | 0.28 | 0.28 | 0.28 | 0.28 | 0.28 | 0.28 | 0.28 | 0.28 | 0.28 |
| CQ | 0.05 | 0.05 | 0.05 | 0.05 | 0.05 | 0.05 | 0.05 | 0.05 | 0.05 | 0.05 |
| DABE | 0.07 | 0.07 | 0.07 | 0.07 | 0.07 | 0.07 | 0.07 | 0.07 | 0.07 | 0.07 |
| Gamma-terpinene | 0.00 | 0.00 | 0.00 | 0.16 | 0.00 | 0.16 | 0.00 | 0.16 | 0.00 | 0.00 |
| Adhesive monomer | 0.00 | 0.00 | 0.00 | 0.00 | 0.00 | 0.00 | 0.00 | 1.00 | 0.00 | 0.00 |

TABLE 2

Paste B

| | Example 1 | Example 2 | Example 3 | Example 4 | Example 5 | Example 6 | Example 7 | Example 8 | Example 9 | Example 10 |
|---|---|---|---|---|---|---|---|---|---|---|
| Nano-SiO$_2$ | 0.00 | 0.00 | 0.00 | 0.00 | 6.15 | 6.16 | 0.00 | 6.16 | 0.00 | 0.00 |
| TCD monomer | 0.00 | 30.34 | 15.17 | 15.17 | 12.32 | 12.32 | 15.17 | 0.00 | 15.17 | 15.17 |
| Compound of Formula (2) | 0.00 | 0.00 | 0.00 | 0.00 | 0.00 | 0.00 | 0.00 | 12.32 | 0.00 | 0.00 |
| PEG400DMA | 30.34 | 0.00 | 15.17 | 15.17 | 12.32 | 12.32 | 15.17 | 12.32 | 0.00 | 0.00 |
| Triethylene glycol-DMA | 0.00 | 0.00 | 0.00 | 0.00 | 0.00 | 0.00 | 0.00 | 0.00 | 15.17 | 0.00 |
| Tetraethylene glycol-DMA | 0.00 | 0.00 | 0.00 | 0.00 | 0.00 | 0.00 | 0.00 | 0.00 | 0.00 | 15.17 |
| GK | 63.70 | 63.70 | 63.70 | 63.70 | 64.70 | 64.69 | 63.70 | 64.69 | 63.70 | 63.70 |
| Silanized silica | 5.56 | 5.56 | 5.56 | 5.56 | 4.11 | 4.11 | 5.56 | 4.11 | 5.56 | 5.56 |
| Cumolhydroperoxide (88%) | 0.40 | 0.40 | 0.40 | 0.40 | 0.40 | 0.40 | 0.40 | 0.40 | 0.40 | 0.40 |

The results of the measurements for the respective root canal sealing materials are listed in the table below.

In the following the root canal sealing materials (root canal sealers) refer to the mixtures existing immediately after mixing of the respective paste A and paste B. The two pastes were mixed together in the same parts by volume (1:1 (v/v)).

TABLE 3

Measurement results

| | Example 1 | Example 2 | Example 3 | Example 4 | Example 5 | Example 6 | Example 7 | Example 8 | Bsp.9 | Bsp.10 |
|---|---|---|---|---|---|---|---|---|---|---|
| Flexural strength [MPa] | 3.6 | 12.7 | 5.7 | 1.1 | 26.4 | 6.5 | 5.6 | 7.1 | | |
| Modulus of elasticity [MPa] | 93 | 255 | 117 | 15 | 600 | 102 | 123 | 105 | | |
| Water absorption [µg/mm$^3$] | 227 | 4 | 23 | 15 | 25 | 16 | 25 | 14 | | |
| Water absorption | 9.85% | 0.18% | 1.01% | 0.66% | 1.01% | 0.65% | 1.10% | 0.57% | | |
| Solubility [µg/mm$^3$] | 8 | 2 | 5 | 4 | 2 | 2 | 5 | 2 | | |
| Solubility | 0.35% | 0.09% | 0.24% | 0.19% | 0.07% | 0.07% | 0.24% | 0.07% | | |
| Flow (ISO 6876) | 17 mm | 32 mm | 27 mm | 30 mm | 30 mm | 30 mm | 28 mm | 29 mm | | |
| Radiopacity (Al) | 6.20 mm | 6.30 mm | 6.25 mm | 6.20 mm | 6.35 mm | 6.35 mm | 6.25 mm | 6.35 mm | | |
| Setting time | 21 min | 19 min | 20 min | 22 min | 21 min | 23 min | 19 min | 22 min | | |
| Processing time | 42 min | 39 min | 40 min | 42 min | 40 min | 44 min | 39 min | 43 min | | |
| Adhesion to dentin | | | 1.4 MPa | | | | 3.3 MPa | | 4.0 MPa | 3.6 MPa |

Results

Example 1, not according to the invention, exhibits very high values for the water absorption and solubility and is therefore unsuitable for use in the sealing and filling of a root canal.

For Example 2, however, the results surprisingly exhibit an unusually low water absorption and an unusually low solubility. Furthermore, the flow of the material is quite exceptional and the mechanical properties acceptable.

Regarding the composition according to the invention of Example 3, it can be stated that through the combination of the monomers of components (a1) and (a2) the value for water absorption in particular is drastically improved compared to comparative example 1.

In the composition according to the invention of Example 4, through the addition of a molecular weight regulator (γ-terpinene), the polymerization process was influenced and the chain length, degree of cross-linking of the resulting polymer and the kinetics of the polymerization process altered in such a way that the particular characteristics are further improved. The results show that the mechanical properties are clearly reduced. The water absorption and flow are surprisingly improved.

In Example 5 the composition according to the invention also contained non-agglomerated, nanoscale particles as a further filler (component (c1)). Obviously because of a better spatial filling of the filler particles the mechanical values are increased while the solubility is considerably reduced.

The composition according to the invention according to Example 6 comprises both a molecular weight regulator (component (d), here: gamma-terpinene) and a nanoscale filler (component (c1)). The mechanical values could thus be even further optimized. The value of the solubility could be set extremely low and the water absorption was likewise very low but with good flow.

The composition according to the invention of Example 8 further shows that through the use of the monomers according to the invention as component (a1) the characteristics can be improved further still.

A composition according to the invention, such as for example the Examples 2, 3, 6 and 8 according to the invention, has in the cured state a sufficient strength but is able to be removed without major effort with a dental instrument, such as a file, from the root canal. The radiopacity with a value of 6.25 through 6.35 mm aluminum is exceptional for diagnosis in the root canal.

Following storage in water of the specimens according to the invention under microscopic examination no marginal gaps between the root canal filling and the root canal wall were observed.

A comparison of the published values of a root canal sealing and/or filling material with a methacrylate resin basis for water absorption and solubility ("Water sorption and solubility of Methacrylate resin based root canal sealers", Journal of Endodontics, 33, 8, 990-994, 2007) with those of the compositions according to the invention, allows the following to be established:

Epiphany® (Pentron) has a water absorption of 8% and EndoREZ® (Ultradent) a water absorption of 3%.

Epiphany® (Pentron) and EndoREZ® (Ultradent) in each case have a solubility of 3.5%.

The compositions according to the invention, on the other hand, have much lower, that is to say much better, values for water absorption and solubility.

Here it is stressed that the determination of the values for water absorption of the compositions according to the invention also took place under more demanding conditions than for the published data from the prior art (7 days versus 24 hours storage in water).

The dentin adhesion was determined in particular for Examples 3, 9 and 10 according to the invention. The compositions according to these examples differ merely by the type of polyethylene glycol dimethacrylate used in each case. The research confirmed that when polyethylene glycol dimethacrylates with 4 ethylene oxide units (tetraethylene glycol—DMA) or approximately 9 ethylene oxide units (PEG-400-DMA) are used dentin adhesion values are achieved which for use of the respective composition as a root canal filling material are preferred.

Measurement Methods:

In order to determine the mechanical properties (flexural strength and modulus of elasticity) the material under investigation was cured exclusively chemically.

Flexural Strength

The flexural strength was determined according to ISO 4049. For this purpose the respective root canal sealing materials (root canal sealers) were filled free from air bubbles in appropriate Teflon moulds, and then covered with film and glass plate and the excesses pressed out by means of a screw clamp. The test specimens were cured for 24 hours at 37° C. in the water bath.

The size of the test specimen (2 mm×2 mm) was measured in the centre with a measuring accuracy of 0.01 mm. Then the test specimens were stressed in a Zwick Z005 universal testing machine (Zwick GmbH, Ulm, Deutschland) at a feed rate of 0.75 mm/min until rupture.

The flexural strength, σ, is calculated in megapascals according to the following equation:

$$\sigma = \frac{3 \cdot F \cdot l}{2 \cdot b \cdot h^2}$$

Where:
F is the maximum force exerted on the test specimen, in Newton;
l is the distance between the supports (20 mm);
b is the width at the centre of the test specimen measured directly before the test, in millimeters;
h is the height at the centre of the test specimen measured directly before the test, in millimeters.

Modulus of Elasticity

The modulus of elasticity was determined from flexural strength measurements by calculating the slope in the linear area.

Water Absorption and Solubility

Water absorption and solubility were determined analogous to ISO 4049. For this purpose the root canal sealers were filled free from air bubbles in appropriate Teflon moulds, and then covered with film and glass plate and the excesses pressed out by means of a screw clamp. The test specimens with a diameter of 15.0±0.1 mm and a height of 1.0±0.1 mm were photocured in segments. Then the test specimens were stored in a desiccator at 37° C. After 22 hours the test specimens were removed, placed in a second desiccator at 23° C. and then weighed to an accuracy of 0.1 mg. This cycle was repeated until a constant weight $m_1$, had been achieved.

Following complete drying two measurements of the diameter were taken at right angles to each other with a measuring accuracy of 0.01 mm and from these the average diameter was calculated. The thickness of the test specimen was measured at the centre and at four evenly spaced points on the circumference to an accuracy of 0.01 mm. The average diameter and the average thickness were used to calculate the volume V.

Then the test specimens were stored for 7 days in water at 37° C., after which they were removed, rinsed with water and dabbed off until no further moisture could be seen on the surface. The test specimens were waved back and forth for 15 seconds in the air and 1 minute after removal from the water they were weighed. The weight is given as $m_2$.

Then the test specimens were again stored in a desiccator at 37° C. After 22 hours the test specimens were removed, placed in a second desiccator at 23° C. for 2 hours and then weighed to an accuracy of 0.1 mg. This cycle was repeated until a constant weight $m_3$, had been achieved.

The water absorption, $W_{sp}$, was calculated according to the following equation:

$$W_{sp} = \frac{m_2 - m_3}{V}$$

Where:
$m_2$ is the weight of the test specimen following storage in water for 7 days in µg;
$m_3$ is the weight of the re-dried test specimen in µg;
V is the volume of the test specimen in mm³.

The solubility, $W_{sl}$, was calculated according to the following equation:

$$W_{sl} = \frac{m_1 - m_3}{V}$$

Where:
$m_1$ the weight of the dried test specimen prior to storage in water in µg;
$m_3$ is the weight of the re-dried test specimen in µg;
V is the volume of the test specimen in mm³.

Flow

The flow was determined according to ISO 6876. 0.05 ml of the mixed root canal sealer was applied to a glass plate (40 mm×40 mm). 3 minutes after mixing began a second glass plate (40 mm×40 mm; 20 g) and a weight (100 g) were applied. 10 minutes after mixing began the weight was removed and the smallest and the largest diameter measured and from these the average diameter calculated.

The flow F is the mean of the average diameters of the three respective individual determinations.

Radiopacity

In order to determine the radiopacity test specimens with a diameter of 15 mm and a height of 2 mm of the root canal sealer were prepared. X-rays were taken of the test specimens in each case along with a staircase-shaped aluminum body (7 mA; 60 kV; 0.04 s).

For the determination the heights of the aluminum stairs and the thickness of the test specimens were determined to an accuracy of 0.01 mm and the gray values for the steps of the aluminum stairs and the test specimens were determined. From these values, by linear regression, the radiopacity in aluminum equivalents was calculated.

Processing Time

The processing time was determined using a Physica MCR 301 rheometer (Anton Paar GmbH, Graz, Austria). For this purpose the viscosity was recorded over time at 23° C. in an oscillation measurement (y=1%, f=4 Hz). The root canal sealer was mixed and applied to the measurement plate of a plate/plate system (d=12 mm, gap=1 mm). The time was started from when mixing began. The processing time was taken from the intersection of the curve of the material not yet cured and the tangent at the steepest point of the curing reaction.

Setting Time

The setting time was determined using a Physica MCR 301 rheometer (Anton Paar GmbH, Graz, Austria). For this purpose the viscosity was recorded as a function of time at 37° C. in an oscillation measurement (y=1%, f=4 Hz). The root canal sealer was mixed and applied to the measurement plate of a plate/plate system (D=12 mm, gap=1 mm). The time was started from when mixing began. The setting time was assessed as the time from when mixing began until a viscosity of $10^4$ Pa·s was reached.

Adhesion to Dentin

The adhesion to dentin was determined in the shear test on bovine dentin. For this purpose the dentin surface was initially ground with 180 grade SiC grinding paper with 180 grit and then ground smooth with 1000 grade SiC grinding paper. The surface was dabbed off until no moisture whatsoever could be seen on it. Then the root canal sealer was applied in a silicon ring (d=5 mm) to the surface and cured for 24 hours at 37° C. in the water bath. Prior to the test the silicon rings were carefully removed. The test specimens were stressed in a Zwick Z005 universal testing machine (Zwick GmbH, Ulm, Germany) at a feed rate of 1 mm/min until rupture. Then the two measurements were taken of the diameter of the adhesive surface of the test specimen at right angles to one another and to an accuracy of 0.01 mm and from this the average diameter was calculated.

The adhesion, $\tau_{Dentin}$, is calculated in megapascals according to the following equation:

$$\tau_{Dentin} = \frac{F}{\pi \cdot \left(\frac{d_1 + d_2}{d}\right)^2}$$

Where:
F is the maximum force exerted on the test specimen, in Newton;
$d_1$ and $d_2$, are the diameters of the test specimen measured at right angles to one another, in millimeters.

Synthesis of the Compound of Formula (2)

0.95 g (4.84 mmol) of 3(4),8(9)-bis(hydroxymethyl)tricyclo[5.2.1.0$^{2,6}$]decane were dissolved in 10 ml of toluene and 0.04 g of BHT and 0.103 g of the catalyst solution (0.50 g dibutyltin(II)dilaurate dissolved in 9.50 g toluene) were added. Under agitation 3.00 g (19.34 mmol, 4 equivalents) of isocyanatoethyl methacrylate dissolved in 10 ml of toluene were dropped in. Once addition was complete the dropping funnel was replaced by a reflux condenser and the reaction mixture heated to 120° C. with the continuation of the reaction being monitored by IR spectroscopy. After 72 hours a further 0.102 g of catalyst solution was added and heating continued until no further isocyanate bands were detected. The solvent was removed using the rotary evaporator. The allophanate of formula (2) was obtained in a yield of 3.83 g (4.69 mmol, 97%) as a light yellowy oil.

Examples 2-7 were repeated exchanging the TCD monomers used there for the compound of formula (2); these further examples are referred to as Examples S2-S7. All parameters determined in Examples 2-7 were also determined for Examples S2-S7. The values of the parameters determined for Examples S2-S7 are similar to those from Examples 2-7 and to some extent surpass these. This shows in addition to Example 8, that the compound of Formula (2), which is representative of the compounds according to the invention, is eminently suitable for use in composite materials according to the invention.

The invention claimed is:

1. A method of performing a dental procedure, comprising: applying a curable dental composition to tissue of a patient for sealing a root canal, wherein said curable dental composition comprises:
   (a) a monomer component comprising
       (a1) one, two or a plurality of polymerizable monomers with a molar mass of less than 4,000 g/mol selected from the group consisting of compounds (monomers) with the structure $Q(Y_xZ_e)_b$, wherein the following applies:
           Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups, alkoxy groups, halogen atoms or trifluoromethyl groups,
           b is an integer selected from the group of integers 2, 3 and 4,
           each Z represents a structure element, which independently of any other structure elements Z is selected from the group consisting of
               —O—(C=O)—CH=CH$_2$, —O—(C=O)—C(CH$_3$)=CH$_2$,
               —(C=O)—CH=CH$_2$, —(C=O)—C(CH$_3$)=CH$_2$,
               —CH=CH$_2$, —C(CH$_3$)=CH$_2$ and
               —O—CH=CH$_2$,
           each index e is an integer, which independently of any further indices e is selected from the group of integers 1, 2, 3 and 4,
           each index x independently of any further indices x represents 0 or 1,
           each Y in the structure $Q(Y_xZ_e)_b$ where x=1 represents a structure element, which bonds the polyalicyclic structure element Q with e structure elements Z, wherein each Y is selected independently of any further structure elements Y,
           wherein at least one x=1 and at least one Y comprises a structure element selected from the group consisting of amine, N-acyl urea, allophanate, biuret, and amide, wherein the amide function is not directly linked with an N atom, an O atom or a carbonyl group, and
       (a2) one, two or a plurality of further polymerizable monomers from the group consisting of acrylates and methacrylates with a polyether structure element, wherein none of these further polymerizable monomers is one of those with the structure $Q(Y_xZ_e)_b$ according to the definition (a1),
       wherein the ratio of the total weight of the (a1) polymerizable monomers to the total weight of the (a2) one, two or a plurality of further polymerizable monomers from the group consisting of acrylates and methacrylates with a polyether structure element is in the range of 1:3 through 3:1,
   (b) one or a plurality of initiators and/or catalysts, and
   (c) a filler component comprising
       (c1) one, two or a plurality of radiopaque fillers,
   and optionally one or a plurality of further additives.

2. The method as claimed in claim 1, wherein the monomer component (a1) contains two or a plurality of the polymerizable monomers as defined in claim 1 under (a1).

3. The method as claimed in claim 1, wherein the monomer component (a2) comprises one or a plurality of polyalkylene glycol di(meth)acrylate(s) with 4 through 10 alkylene oxide units.

4. The method as claimed in claim 3, wherein said one or a plurality of polyalkylene glycol di(meth)acrylate(s) comprises one or a plurality of polyethylene glycol di(meth)acrylate(s) with 4 through 10 ethylene oxide units.

5. The method as claimed in claim 1, wherein the monomer component (a) comprises
   5 to 48.5 wt-% of component (a1),
   or
   5 to 48.5 wt-% of component (a2),
   or both,
   in each case in relation to the total weight of the composition.

6. The method as claimed in claim 1, wherein the monomer component (a) comprises
   8 to 30 wt-% of component (a1),
   or
   8 to 30 wt-% of component (a2),
   or both, in each case in relation to the total weight of the composition.

7. The method as claimed in claim 1, composing as component (c) a total amount of the filler of components in the range 35 through 85 wt. % in relation to the total weight of the composition.

8. The method as claimed in claim 1, comprising as component (c) a total amount of the filler of components in the range 50 through 85 wt. % in relation to the total weight of the composition.

9. The method as claimed in claim 1, wherein one, two or a plurality of compounds of structure $Q(Y_xZ_e)_b$, have a tricyclo[5.2.1.0$^{2,6}$]-decane radical or a tricyclo[3.3.1.1$^{3,7}$]decane radical and Z is selected from the group consisting of —O—(C=O)—CH=CH$_2$ and —O—(C=O)—C(CH$_3$)=CH$_2$.

10. The method as claimed in claim 1, comprising as an additive one or a plurality of molecular weight regulators as component (d).

11. The method as claimed in claim 10, wherein said one or a plurality of molecular weight regulators as component (d) are selected from the group consisting of dienes, which through abstraction of an allyl H-atom can form a delocalized electron system, extending across 5 or more C-atoms.

12. The method as claimed in claim 1, wherein the filler component (c) also comprises
   (c2) one or a plurality of non-radiopaque fillers.

13. The method as claimed in claim 1, further comprising one or a plurality of adhesion-promoting additives as component (f).

14. The method as claimed in claim 13, wherein said one or a plurality of adhesion-promoting additives is selected from the group consisting of polymerizable or non-polymerizable acids, acid anhydrides and esters.

15. The method as claimed in claim 1, further comprising:
   mixing constituents (a), (b) and (c), and optionally further additives,
   or
   preparing a multi-component system comprising all constituents (a), (b), (c), and optionally further additives,
   wherein the initiators and/or catalysts of the constituent (b) are distributed over separate components of the dental composition so that a chemical initiation is triggered through the mixing of said components.

16. The method of claim 15, wherein said constituents (a), (b) and (c), and optionally further additives comprise a bi-component system.

17. The method as claimed in claim 1, wherein said tissue comprises one or more teeth of a patient.

18. The method as claimed in claim 1, wherein at least one x=1 and at least two Y in the structure $Q(Y_xZ_e)_b$ comprises a structure element selected from the group consisting of N-acyl urea, allophanate, biuret, and amide, wherein the amide function is not directly linked with an N atom, an O atom or a carbonyl group.

19. The method as claimed in claim 1, wherein at least one Y in the structure $Q(Y_xZ_e)_b$ comprises a structure element selected from the group consisting of

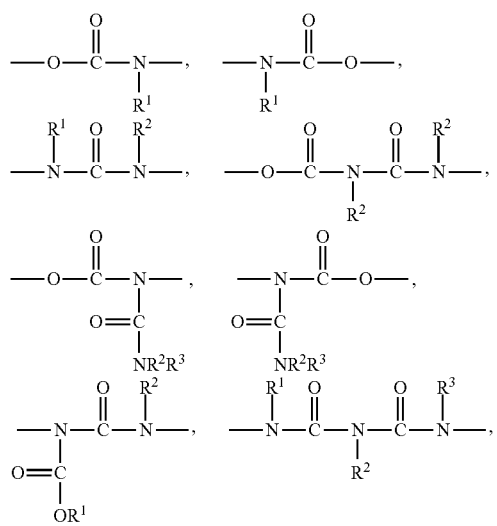

-continued

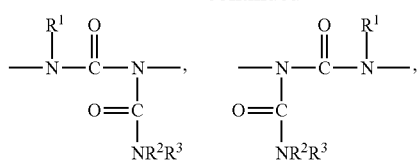

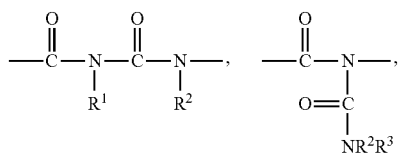

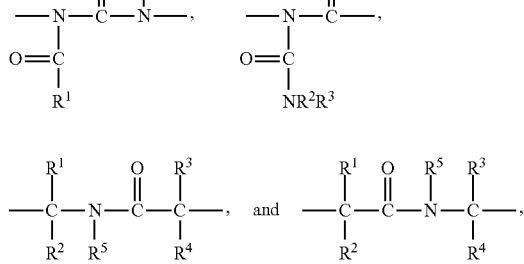

wherein $R^1$, $R^2$, $R^3$ R4 and $R^5$ represent other radicals of the compound, wherein in each case the bond arranged to the left of the graphic formula is closer to the structure element Q and the bond arranged on the right is closer to the structure element Z.

* * * * *

UNITED STATES PATENT AND TRADEMARK OFFICE
CERTIFICATE OF CORRECTION

PATENT NO. : 8,915,736 B2
APPLICATION NO. : 13/248951
DATED : December 23, 2014
INVENTOR(S) : Tobias Blömker et al.

Page 1 of 1

It is certified that error appears in the above-identified patent and that said Letters Patent is hereby corrected as shown below:

Claims

In Column 69, line 24 of Claim 19 structure elements show:

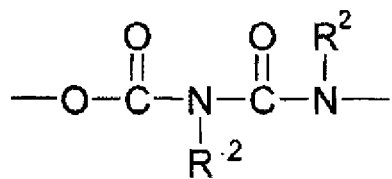

but should show:

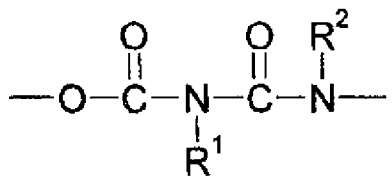

Signed and Sealed this
Sixth Day of October, 2015

Michelle K. Lee
*Director of the United States Patent and Trademark Office*